(12) United States Patent
Shi et al.

(10) Patent No.: US 10,537,882 B2
(45) Date of Patent: Jan. 21, 2020

(54) HETEROATOM-CONTAINING NANOCARBON MATERIAL, PREPARATION METHOD AND USE THEREOF, AND METHOD FOR DEHYDROGENATION REACTION OF HYDROCARBONS

(71) Applicants: CHINA PETROLEUM & CHEMICAL CORPORATION, Beijing (CN); RESEARCH INSTITUTE OF PETROLEUM PROCESSING, Beijing (CN)

(72) Inventors: Chunfeng Shi, Beijing (CN); Junfeng Rong, Beijing (CN); Peng Yu, Beijing (CN); Jingxin Xie, Beijing (CN); Mingsheng Zong, Beijing (CN); Weiguo Lin, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 41 days.

(21) Appl. No.: 15/546,791

(22) PCT Filed: Jan. 27, 2016

(86) PCT No.: PCT/CN2016/000059
§ 371 (c)(1),
(2) Date: Jul. 27, 2017

(87) PCT Pub. No.: WO2016/119568
PCT Pub. Date: Aug. 4, 2016

(65) Prior Publication Data
US 2018/0015445 A1    Jan. 18, 2018

(30) Foreign Application Priority Data

Jan. 27, 2015 (CN) .......................... 2015 1 0040980
Jan. 27, 2015 (CN) .......................... 2015 1 0041118
(Continued)

(51) Int. Cl.
*C01B 32/15* (2017.01)
*C01B 32/18* (2017.01)
(Continued)

(52) U.S. Cl.
CPC .......... *B01J 27/24* (2013.01); *B01J 35/1014* (2013.01); *B01J 35/1019* (2013.01); *B01J 37/08* (2013.01); *C07C 5/48* (2013.01); *C07C 2527/24* (2013.01)

(58) Field of Classification Search
CPC ........ C01B 32/15; C01B 32/18; C01B 32/182
(Continued)

(56) References Cited

U.S. PATENT DOCUMENTS

2013/0048919 A1    2/2013   Chung et al.

FOREIGN PATENT DOCUMENTS

CN    1911502 A     2/2007
CN    101014412 A   8/2007
(Continued)

OTHER PUBLICATIONS

Maksimova et al. "Nanocarbons in selective oxidative dehydrogenation reaction" Mar. 2005 ; Science Direct; Catalysis Today; pp. 110-114.*
(Continued)

*Primary Examiner* — Thuan D Dang
(74) *Attorney, Agent, or Firm* — Novick, Kim & Lee, PLLC; Allen Xue

(57) ABSTRACT

A heteroatom-containing nano-carbon material, based on the total weight of said heteroatom-containing nano-carbon
(Continued)

material and calculated as the elements, has an oxygen content of 1-6 wt %, a nitrogen content of 0-2 wt %, a carbon content of 92-99 wt %. In its XPS, the ratio of the oxygen content as determined with the peak(s) in the range of 531.0-532.5 eV to the oxygen content as determined with the peak(s) in the range of 532.6-533.5 eV is 0.2-0.8; the ratio of the carbon content as determined with the peak(s) in the range of 288.6-288.8 eV to the carbon content as determined with the peak(s) in the range of 286.0-286.2 eV is 0.2-1; the ratio of the nitrogen content as determined with the peak(s) in the range of 398.5-400.1 eV to the total nitrogen content is 0.7-1. The heteroatom-containing nano-carbon material shows a good catalytic capability in dehydrogenation of hydrocarbons.

35 Claims, 2 Drawing Sheets

(30) Foreign Application Priority Data

Oct. 26, 2015 (CN) .......................... 2015 1 0702816
Oct. 26, 2015 (CN) .......................... 2015 1 0703329

(51) Int. Cl.
  *C01B 32/182* (2017.01)
  *B01J 27/24* (2006.01)
  *C07C 5/48* (2006.01)
  *B01J 35/10* (2006.01)
  *B01J 37/08* (2006.01)

(58) Field of Classification Search
  USPC .... 423/447.1, 447.2, 447.3, 445 B; 977/742, 977/734, 741, 749
  See application file for complete search history.

(56) References Cited

FOREIGN PATENT DOCUMENTS

| CN | 101718011 A | 6/2010 |
| CN | 101863463 A | 10/2010 |
| CN | 102489283 A | 6/2012 |
| CN | 103706388 A | 4/2014 |
| JP | 2008506514 A | 3/2008 |
| KR | 20100046697 A | 5/2010 |
| KR | 101473752 B1 | 12/2014 |
| WO | 0151201 A1 | 7/2001 |
| WO | 2010100941 A1 | 9/2010 |

OTHER PUBLICATIONS

Ishizaki et al. "Electrocatalytic activity for the oxygen reduction reaction of oxygen-containing nanocarbon synthesized by solution plasma"; Apr. 2014 ; The Royal Society of Chemistry; Journal of Materials Chemistry; pp. 10589-10598.*
European Patent Office, "Supplementary European Search Report" for counterpart application EP 16742630, dated Jul. 24, 2018.
Zhang, L. et al., Mild hydrothermal treatment to prepare highly dispersed multi-walled carbon nanotubes, Applied Surface Science, vol. 257, Issue 6, pp. 1845-1849, Sep. 9, 2019.
Duesberg, G. S. et al., Hydrothermal functionalisation of single-walled carbon nanotubes, Synthetic Metals, Apr. 13, 2004, vol. 142, pp. 263-266.
Chen, L. et al., One-Step Hydrothermal Synthesis of Nitrogen-Doped Carbon Nanotubes as an Efficient Electrocatalyst for Oxygen Reduction Reactions. Chem. Asian J., Oct. 2014, vol. 9, No. 10, pp. 2915-2920.
Zhang, J. et al., Surface-Modified Carbon Nanotubes Catalyze Oxidative Dehydrogenation of n-Butane, Science, Oct. 3, 2008, vol. 322, pp. 73-77.
Japanese Patent Office, office action for JP Application No. 2017-539317, dated Oct. 23, 2019.

* cited by examiner

HETEROATOM-CONTAINING NANOCARBON MATERIAL, PREPARATION METHOD AND USE THEREOF, AND METHOD FOR DEHYDROGENATION REACTION OF HYDROCARBONS

TECHNICAL FIELD

The present invention relates to a heteroatom-containing nano-carbon material and a preparation process thereof. The present invention also relates to the use of said heteroatom-containing nano-carbon material as a catalyst in the dehydrogenation of hydrocarbons, and a process for dehydrogenating hydrocarbons.

BACKGROUND

The dehydrogenation of hydrocarbons is an important reaction. For example, most of lower olefins are obtained through the dehydrogenation of lower alkanes. The dehydrogenation can be classified into two types, direct dehydrogenation (not involving oxygen) or oxidation dehydrogenation (involving oxygen).

It has been proved that several types of nano-carbon materials have catalytic effects on the direct dehydrogenation and the oxidation dehydrogenation of hydrocarbons. Incorporation of oxygen and/or nitrogen atoms into the nano-carbon material can improve its catalytic effect.

Incorporation of oxygen atoms into the nano-carbon material can form oxygen-containing functional groups such as hydroxyl, carbonyl, carboxyl, ester and anhydride groups on the surface of the nano-carbon material.

The nano-carbon material can be oxidized to introduce the oxygen atom into the nano-carbon material and increase the amount of the oxygen-containing functional groups in the nano-carbon material. For example, the nano-carbon material can be treated in a reflux condition of a strong acid (e.g. $HNO_3$, $H_2SO_4$) and/or a strong oxidative solution (e.g. $H_2O_2$, $KMnO_4$) optionally in the help of the microwave heating or the ultrasonic oscillation to enhance the oxidation effect. However, the reflux treatment in the strong acid and/or the strong oxidative solution will have a negative effect on the framework structure of the nano-carbon material, and even destroy the framework structure of the nano-carbon material. For example, the reflux treatment of the nano-carbon material in a nitric acid solution can introduce a large amount of oxygen-containing functional groups to the surface of the nano-carbon material, but said treatment will be apt to cut off the nano-carbon material and/or remarkably increase the defect sites in the graphite network structure, and therefore reduce the properties of the nano-carbon material, e.g. thermostability. In addition, the amount of the oxygen atoms introduced by the reflux treatment in the strong acid and/or the strong oxidative solution has a high dependency on the reaction conditions, and will fluctuate widely.

For the introduction of the nitrogen atom into the nano-carbon material, according to the chemical environment in which the nitrogen atoms in the nano-carbon material exist, the nitrogen atoms can be divided into the chemical nitrogens and the structural nitrogens. The chemical nitrogens are mainly present on the material surface in form of the surface functional groups, e.g. the surface nitrogen-containing functional groups such as amino or nitrosyl. The structural nitrogen means the nitrogen atom is present in the framework structure of the nano-carbon material and bonded to the carbon atom(s). The structural nitrogen mainly comprises the graphite-type nitrogen (i.e., 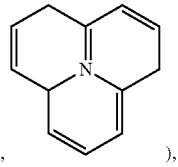), the pyridine-type nitrogen (i.e., 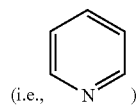)

and the pyrrole-type nitrogen (i.e., 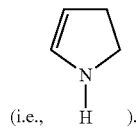).

The graphite-type nitrogen directly replaces the carbon atom in the lattice of the graphite to form a saturated nitrogen atom; the pyridine-type nitrogen and the pyrrole-type nitrogen are unsaturated nitrogen atoms, and will usually cause the deficiency of the adjacent carbon atoms upon replacing the carbon atom to form defect sites.

The nitrogen element can be introduced to the framework structure and/or the surface of the nano-carbon material with the high temperature and/or the high pressure in the synthesis process of the nano-carbon material by introducing a nitrogen-containing functional atmosphere (e.g. ammonia, nitrogen, urea, and melamine) in the synthesis process of the nano-carbon material; or the nitrogen element can be introduced to the surface of the nano-carbon material with the high temperature and/or the high pressure by placing the nano-carbon material in a nitrogen-containing functional atmosphere (e.g. ammonia, nitrogen, urea, and melamine). The high temperature and/or the high pressure can form the structural nitrogen of the nano-carbon material; however the type of the nitrogen-containing species depends on the reaction conditions and is not easily controllable. Moreover, different types of the formed nitrogen-containing species are not evenly distributed on the surface of the nano-carbon material, leading to the instability of the properties of the nitrogen-containing nano-carbon material. The nano-carbon material can be also oxidized and then reacted with an amine to introduce the nitrogen atom to the surface of the nano-carbon material. The introduced nitrogen atom is substantially the chemical nitrogen.

Although there are some processes in the investigations on the doping-modified nano-carbon material and the catalytic capability thereof, however the scientists and reservations have not reached the consensus for some basic core issues, and there is still a need to further investigate the doping-modified nano-carbon material, the preparation process thereof and the catalytic capability thereof.

SUMMARY OF THE INVENTION

An object of the present invention is to provide a process for preparing a heteroatom-containing nano-carbon material. The process can not only introduce heteroatoms on/into the surface of the nano-carbon material, but also have little impact on the structure of the nano-carbon material itself. Another object of the present invention is to provide a heteroatom-containing nano-carbon material. When said heteroatom-containing nano-carbon material is used in the dehydrogenation of hydrocarbons, not only relatively high reactant conversion can be achieved, but also relatively high product selectivity can be accomplished.

Yet another object of the present invention is to provide a process for dehydrogenating hydrocarbons, which can achieve both relatively high reactant conversion and relatively high product selectivity. According to the first aspect of the present invention, the present invention provides a heteroatom-containing nano-carbon material, said heteroatom-containing nano-carbon material contains a carbon element, an oxygen element, and an optional nitrogen element, based on the total weight of said heteroatom-containing nano-carbon material and calculated as the elements, the content of the oxygen element is 1-6 wt %, the content of the nitrogen element is 0-2 wt %, the content of the carbon element is 92-99 wt %;

In said heteroatom-containing nano-carbon material, the amount of the oxygen element as determined with the peak(s) in the range of 531.0-532.5 eV in the X-ray photoelectron spectroscopy is $I_O^c$, the amount of the oxygen element as determined with the peak(s) in the range of 532.6-533.5 eV in the X-ray photoelectron spectroscopy is $I_O^e$, $I_O^c/I_O^e$ is 0.2-0.8; In said heteroatom-containing nano-carbon material, the content of the carbon element as determined with the peak(s) in the range of 288.6-288.8 eV in the X-ray photoelectron spectroscopy is $I_C^c$, the content of the carbon element as determined with the peak(s) in the range of 286.0-286.2 eV in the X-ray photoelectron spectroscopy is $I_C^e$, $I_C^c/I_C^e$ is 0.2-1;

When the content of the nitrogen element in said heteroatom-containing nano-carbon material is 0.1 wt % or higher, the total content of the nitrogen element of said heteroatom-containing nano-carbon material as determined with the X-ray photoelectron spectroscopy is $I_N^t$, the content of the nitrogen element as determined with the peak(s) in the range of 398.5-400.1 eV in the X-ray photoelectron spectroscopy is $I_N^c$, $I_N^c/I_N^t$ is 0.7-1.

The heteroatom-containing nano-carbon material according to the first aspect of the present invention is a calcined one or a non-calcined one.

According to the second aspect of the present invention, the present invention provides a process for preparing the heteroatom-containing nano-carbon material, the process comprises reacting an aqueous dispersion, in which the nano-carbon material as starting material is dispersed, in a close vessel. Said aqueous dispersion optionally contains an organic base. Said organic base is an amine and/or a quaternary ammonium base. Said aqueous dispersion is kept at a temperature in a range of 80-220° C. during the reaction.

According to the third aspect of the present invention, the present invention provides a heteroatom-containing nano-carbon material prepared with the process according to the second aspect of the present invention. The heteroatom-containing nano-carbon material according to the third aspect of the present invention is a calcined one or a non-calcined one.

According to the fourth aspect of the present invention, the present invention provides a heteroatom-containing nano-carbon material, wherein said heteroatom-containing nano-carbon material is produced by calcining the heteroatom-containing nano-carbon material (for example, which is not calcined) according to the first or third aspect of the present invention.

According to the fifth aspect of the present invention, the present invention provides use of the heteroatom-containing nano-carbon material according to the first aspect of the present invention, the heteroatom-containing nano-carbon material according to the third aspect of the present invention, or the heteroatom-containing nano-carbon material according to the fourth aspect of the present invention as a catalyst in the dehydrogenation of hydrocarbons.

According to the sixth aspect of the present invention, the present invention provides a process for dehydrogenation of hydrocarbons, which process comprises contacting in presence or absence of oxygen, in a hydrocarbon dehydrogenation condition, contacting the hydrocarbons with the heteroatom-containing nano-carbon material according to the first aspect of the present invention, the heteroatom-containing nano-carbon material according to the third aspect of the present invention, or the heteroatom-containing nano-carbon material according to the fourth aspect of the present invention.

The process for preparing the heteroatom-containing nano-carbon material according to the present invention can not only stably adjust/control and/or increase the heteroatom content in the nano-carbon material, but also has little influence on the structure of the nano-carbon material itself. The prepared heteroatom-containing nano-carbon material has stable properties.

The heteroatom-containing nano-carbon material according to the present invention has a good catalytic performance in the dehydrogenation of hydrocarbons, and remarkably increases the reactant conversion and the product selectivity.

BRIEF DESCRIPTION OF THE DRAWINGS

The drawings are provided for the better understanding of the present invention and constitute a part of the specification. The drawings are provided for explaining the present invention together with the following detailed description, but have no limitation to the present invention in any way.

DETAILED DESCRIPTION

Figure 1:
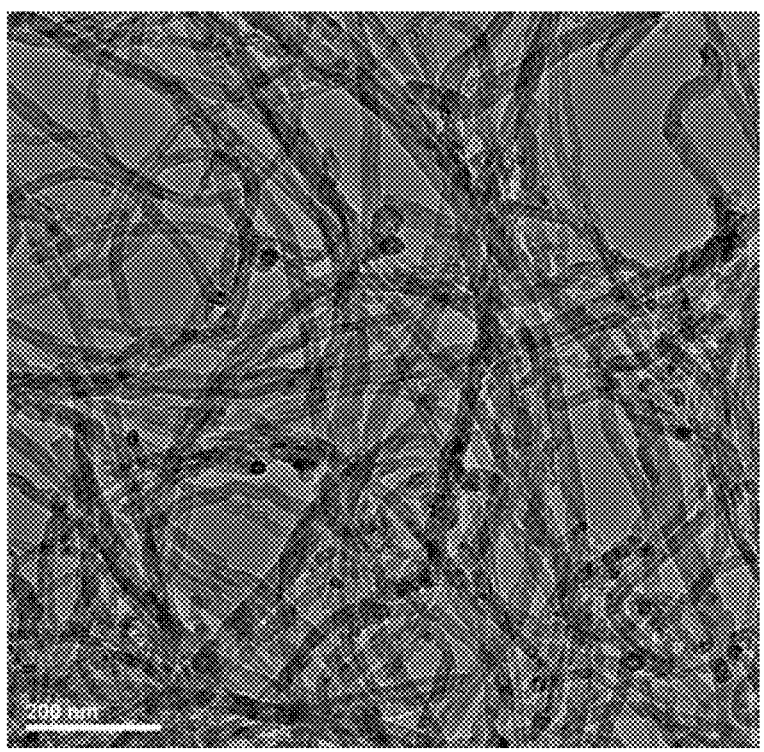
FIG. 1 shows a transmission electron microscope photo of the heteroatom-containing nano-carbon material prepared according to Preparation Example 1.

Hereinafter, with respect to the numerical range, the combination of two end-points of any two disclosed ranges, or the combination of any one end-point of any disclosed range with any one specifically disclosed point, or the combination of any two specifically disclosed points can form a new range. All of these newly formed ranges are considered as being specifically disclosed in the present invention. Hereinafter, in principle, the disclosed technical solutions can be combined with each other to form a new technical solution. All of these newly formed technical solutions are considered as being specifically disclosed in the present invention.

In the present invention, the nano-carbon material means a carbonaceous material having a disperse phase size in at least one dimension of less than 100 nm.

According to the first aspect of the present invention, the present invention provides a heteroatom-containing nano-carbon material, and said heteroatom-containing nano-carbon material contains a carbon element, an oxygen element, an oxygen element and an optional nitrogen element. In the present invention, the term "optional" represents the presence or the absence. Based on the total weight of the heteroatom-containing nano-carbon material and calculated as element, the content of the oxygen element is 1-6 wt %, the content of the nitrogen element is 0-2 wt %, and the content of the carbon element is 92-99 wt %.

In an embodiment, the sum of the contents of every components of the heteroatom-containing nano-carbon material is 100 wt %.

In an embodiment, in said heteroatom-containing nano-carbon material, when the content of the nitrogen element is lower than 0.1 wt %, based on the total weight of said heteroatom-containing nano-carbon material and calculated as the elements, the content of the oxygen element can be 2.5-5.8 wt %, preferably 3-5.6 wt %, more preferably 4.5-5.5 wt %; the content of the carbon element can be 94.2-97.5 wt %, preferably 94.4-97 wt %, more preferably 94.5-95.5 wt %. When the heteroatom-containing nano-carbon material according to said embodiment is used as a catalyst for the dehydrogenation of alkanes, in particular, butane (e.g. n-butane), not only relatively high reactant conversion can be achieved, but also relatively high 1-alkene (e.g. 1-butene) selectivity can be accomplished.

In a preferable embodiment, the heteroatom-containing nano-carbon material preferably contains the N element, in order to further improve the catalytic performance upon being used as the catalyst in the dehydrogenation of hydrocarbons. More preferably, based on the total weight of said heteroatom-containing nano-carbon material and calculated as the elements, the content of the oxygen element is 2-6 wt %, preferably 3.5-5.5 wt %; the content of the nitrogen element is 0.2-1.8 wt %, preferably 0.5-1.8 wt %; and the content of the carbon element is 92.2-97.8 wt %, preferably 92.7-96 wt %.

In an embodiment, in said heteroatom-containing nano-carbon material, the contents of C, N and O elements can be:

In an embodiment, in said heteroatom-containing nano-carbon material, the sum of the contents of the carbon element, the nitrogen element and the oxygen element is higher than 99.9 wt %.

In an embodiment, in said heteroatom-containing nano-carbon material, the sum of the contents of the carbon element, the nitrogen element and the oxygen element is 100%.

In the present invention, the element contents of every components of the heteroatom-containing nano-carbon material can be measured with the X-ray photoelectron spectroscopy (XPS) method, wherein the element contents are determined with the area of 1s electron peaks; the samples are dried for 3 hours at 150° C. and 1 atm in a helium atmosphere before the test. When an element is measured as having a content of lower than 0.1 wt %, the content of said element is determined to be 0.

In the present invention, the X-ray photoelectron spectroscopy analysis is carried out with an ESCALab250 type X-ray photoelectron spectroscoper equipped with Thermo Advantage V5.926 software (Thermo Scientific Company), wherein the excitation source is a monochromatic Al Kα X-ray, the energy is 1486.6 eV, the power is 150 W, and the pass energy for narrow scan is 30 eV. The basis vacuum for analysis and test is $6.5 \times 10^{-10}$ mbar. The electron binding energy is corrected with the C1s peak (284.0 eV) of the simple substance of carbon. The data is treated with the Thermo Advantage software. The quantitative analysis is carried out in the analysis module with the sensitivity factor method.

The analysis of the element content of the heteroatom-containing nano-carbon material of the present invention with the XPS analysis is a conventional means in the art and can quantitatively determine the surface element composition. The analyzed surface range (depth) of the nano-carbon material depends on the used XPS analysis device. In the present invention, the analyzed surface range (depth) can generally be 0-20 nm (a range from the surface to the 20 nm depth), preferably 0-10 nm (a range from the surface to the 10 nm depth).

In said heteroatom-containing nano-carbon material, the amount of the oxygen element (i.e., C=O) determined with the peak(s) in the range of 531.0-532.5 eV in the X-ray photoelectron spectroscopy is $I_O^c$, the amount of the oxygen element (i.e., C—O) determined with the peak(s) in the range of 532.6-533.5 eV in the X-ray photoelectron spec-

| C (wt %) | 80-96 | 92-96 | 90-95 | 94.1 | 93.2 | 93 | 93.8 | 93.6 | 93.1 | 94.1 |
| N (wt %) | 0.5-5 | 0.5-2 | 0.8-2 | 1.8 | 4.7 | 1.5 | 1.4 | 1.7 | 1.5 | 1.6 |
| O (wt %) | 2-15 | 2-6 | 4-10 | 4.1 | 2.1 | 5.5 | 4.8 | 4.7 | 5.4 | 4.3 | and the sum of the contents of every components of the heteroatom-containing nano-carbon material is 100 wt %.

In an embodiment, in said heteroatom-containing nano-carbon material, the sum of the contents of the carbon element, the nitrogen element and the oxygen element is higher than 98 wt %.

In an embodiment, in said heteroatom-containing nano-carbon material, the sum of the contents of the carbon element, the nitrogen element and the oxygen element is higher than 99 wt %.

In an embodiment, in said heteroatom-containing nano-carbon material, the sum of the contents of the carbon element, the nitrogen element and the oxygen element is higher than 99.5 wt %.

troscopy is $I_O^e$, $I_O^c/I_O^e$ is 0.2-0.8, for example, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80 or a numerical range formed with any two of the above values. In said heteroatom-containing nano-carbon material, if the content of the nitrogen element is lower than 0.1 wt %, $I_O^c/I_O^e$ is preferably 0.4-0.7, more preferably 0.55-0.65. In said heteroatom-containing nano-carbon material, if the content of the nitrogen element is 0.1 wt % or higher, $I_O^c/I_O^e$ is preferably 0.35-0.85, more preferably 0.45-0.8. In the present invention, the numerical range includes two end-points unless indicated to the contrary.

According to the present invention, $I_O^e$ represents the relative mole content of C—O groups in the carbonaceous material; $I_O^c$ represents the relative mole content of C=O groups in the carbonaceous material; $I_O^e$ and $I_O^c$ can be respectively determined with a certain range of the peaks in the X-ray photoelectron spectroscopy. For example, $I_O^e$ can be determined with an integral area of the peak(s) in the range of 532.6-533.5 eV in the X-ray photoelectron spectroscopy; $I_O^c$ can be determined with an integral area of the peak(s) in the range of 531.0-532.5 eV in the X-ray photoelectron spectroscopy. Again for example, $I_O^e$ can be determined with an integral area of the peak(s) in the range of 533.1-533.5 eV in the X-ray photoelectron spectroscopy; $I_O^c$ can be determined with an integral area of the peak(s) in the range of 531.8-532.2 eV in the X-ray photoelectron spectroscopy. Again for example, $I_O^e$ can be determined with an integral area of the peak(s) in the range of 533.13-533.53 eV in the X-ray photoelectron spectroscopy; $I_O^c$ can be determined with an integral area of the peak(s) in the range of 531.76-532.16 eV in the X-ray photoelectron spectroscopy. Again for example, $I_O^e$ can be determined with an integral area of the peak(s) in the range of 533.16-533.56 eV in the X-ray photoelectron spectroscopy; $I_O^c$ can be determined with an integral area of the peak(s) in the range of 531.85-532.25 eV in the X-ray photoelectron spectroscopy.

In an embodiment of the heteroatom-containing nano-carbon material according to the present invention, the ratio of the amount of the oxygen element determined with the peak(s) in the range of 531.85-532.25 eV in the X-ray photoelectron spectroscopy (i.e., C=O) to the amount of the oxygen element determined with the peak(s) in the range of 533.16-533.56 eV in the X-ray photoelectron spectroscopy (i.e., C—O) canbel:(0.2-5) or 1:(1.25-5); for example 1:5, 1:2.3, 1:1.8, 1:1.7, 1:1.6, 1:1.5, 1:1.4, 1:1.25 and a numerical range formed by combining any two of the above point values.

In the present invention, the total amount of the oxygen element is determined with the area of O1s peaks in the X-ray photoelectron spectroscopy $A_O^1$. The O1s peaks in the X-ray photoelectron spectroscopy are divided into two groups, i.e., the peak(s) in the range of 531.0-532.5 eV (corresponding to C=O substances) and the peak(s) in the range of 532.6-533.5 eV (corresponding to C—O substances). The area of the peak(s) in the range of 531.0-532.5 eV is named as $A_O^2$, and the area of the peak(s) in the range of 532.6-533.5 eV is named as $A_O^3$. $I_O^c/I_O^e=A_{O2}/A_O^3$. In said heteroatom-containing nano-carbon material, based on the total amount of the carbon element determined with the X-ray photoelectron spectroscopy, the content of the carbon element determined with the peak(s) in the range of 284.7-284.9 eV in the X-ray photoelectron spectroscopy (i.e., graphite-type carbon) can be 20 wt % or higher, preferably 40 wt % or higher, more preferably 50 wt % or higher, further preferably 70 wt % or higher, for example, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 3 wt % or higher, 32 wt % or higher, 33 wt % or higher, 34 wt % or higher, 35 wt % or higher, 36 wt % or higher, 37 wt % or higher, 38 wt % or higher, 39 wt % or higher, 40 wt % or higher, 41 wt % or higher, 42 wt % or higher, 43 wt % or higher, 44 wt % or higher, 45 wt % or higher, 46 wt % or higher, 47 wt % or higher, 48 wt % or higher, 49 wt % or higher, 50 wt % or higher, 51 wt % or higher, 52 wt % or higher, 53 wt % or higher, 54 wt % or higher, 55 wt % or higher, 56 wt % or higher, 57 wt % or higher, 58 wt % or higher, 59 wt % or higher, 60 wt % or higher, 61 wt % or higher, 62 wt % or higher, 63 wt % or higher, 64 wt % or higher, 65 wt % or higher, 66 wt % or higher, 67 wt % or higher, 68 wt % or higher, 69 wt % or higher, 70 wt % or higher, 71 wt % or higher, 72 wt % or higher, 73 wt % or higher, 74 wt % or higher, 75 wt % or higher, 76 wt % or higher, 77 wt % or higher, 78 wt % or higher, 79 wt % or higher, 80 wt % or higher, 81 wt % or higher, 82 wt % or higher, 83 wt % or higher, 84 wt % or higher, 85 wt % or higher, 86 wt % or higher, 87 wt % or higher, 88 wt % or higher, 89 wt % or higher, 90 wt % or higher, 91 wt % or higher, 92 wt % or higher, 93 wt % or higher, 94 wt % or higher, 95 wt % or higher, 96 wt % or higher, 97 wt % or higher, 98 wt % or higher, 99 wt % or higher. The content of the carbon element determined with the peak(s) in the range of 284.7-284.9 eV in the X-ray photoelectron spectroscopy (i.e., graphite-type carbon) can be 95 wt % or lower, preferably 90 wt % or lower, e.g., 20 wt % or lower, 21 wt % or lower, 22 wt % or lower, 23 wt % or lower, 24 wt % or lower, 25 wt % or lower, 26 wt % or lower, 27 wt % or lower, 28 wt % or lower, 29 wt % or lower, 30 wt % or lower, 31 wt % or lower, 32 wt % or lower, 33 wt % or lower, 34 wt % or lower, 35 wt % or lower, 36 wt % or lower, 37 wt % or lower, 38 wt % or lower, 39 wt % or lower, 40 wt % or lower, 41 wt % or lower, 42 wt % or lower, 43 wt % or lower, 44 wt % or lower, 45 wt % or lower, 46 wt % or lower, 47 wt % or lower, 48 wt % or lower, 49 wt % or lower, 50 wt % or lower, 5 wt % or lower, 52 wt % or lower, 53 wt % or lower, 54 wt % or lower, 55 wt % or lower, 56 wt % or lower, 57 wt % or lower, 58 wt % or lower, 59 wt % or lower, 60 wt % or lower, 61 wt % or lower, 62 wt % or lower, 63 wt % or lower, 64 wt % or lower, 65 wt % or lower, 66 wt % or lower, 67 wt % or lower, 68 wt % or lower, 69 wt % or lower, 70 wt % or lower, 71 wt % or lower, 72 wt % or lower, 73 wt % or lower, 74 wt % or lower, 75 wt % or lower, 76 wt % or lower, 77 wt % or lower, 78 wt % or lower, 79 wt % or lower, 80 wt % or lower, 81 wt % or lower, 82 wt % or lower, 83 wt % or lower, 84 wt % or lower, 85 wt % or lower, 86 wt % or lower, 87 wt % or lower, 88 wt % or lower, 89 wt % or lower, 90 wt % or lower, 91 wt % or lower, 92 wt % or lower, 93 wt % or lower, 94 wt % or lower, 95 wt % or lower.

The total content of the carbon element, as determined with the peak(s) in the range of 286.0-288.8 eV in the X-ray photoelectron spectroscopy, can be 5 wt % or higher, preferably 10 wt % or higher, for example, 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher, 39 wt % or higher, 40 wt % or higher, 41 wt % or higher, 42 wt % or higher, 43 wt % or higher, 44 wt % or higher, 45 wt % or higher, 46 wt % or higher, 47 wt % or higher, 48 wt % or higher, 49 wt % or higher, 50 wt % or higher, 51 wt % or higher, 52 wt % or higher, 53 wt % or higher, 54 wt % or higher, 55 wt % or higher, 56 wt % or higher, 57 wt % or higher, 58 wt % or higher, 59 wt % or higher, 60 wt % or higher, 61 wt % or higher, 62 wt % or higher, 63 wt % or higher, 64 wt % or higher, 65 wt % or higher, 66 wt % or higher, 67 wt % or higher, 68 wt % or higher, 69 wt % or higher, 70 wt % or higher, 71 wt % or higher, 72 wt % or higher, 73 wt % or higher, 74 wt % or higher, 75 wt % or higher, 76 wt % or higher, 77 wt % or higher, 78 wt % or higher, 79 wt % or higher, 80 wt % or higher, 81 wt % or higher, 82 wt % or higher, 83 wt % or higher, 84 wt % or higher, 85 wt % or higher, 86 wt % or higher, 87 wt % or higher, 88 wt % or higher, 89 wt % or higher, 90 wt % or higher, 91 wt % or higher, 92 wt % or higher, 93 wt % or higher, 94 wt % or higher, 95 wt % or higher, 96 wt % or higher, 97 wt % or higher, 98 wt % or higher, 99 wt % or higher. The total content of the carbon element, as determined with the peak(s) in the range of 286.0-288.8 eV in the X-ray photoelectron spectroscopy, can be 80 wt % or lower, preferably 60 wt % or lower, more preferably 50 wt % or lower, further preferably 30 wt % or lower, for example, 5 wt % or lower, 6 wt % or lower, 7 wt % or lower, 8 wt % or lower, 9 wt % or lower, 10 wt % or lower, 11 wt % or lower, 12 wt % or lower, 13 wt % or lower, 14 wt % or lower, 15 wt % or lower, 16 wt % or lower, 17 wt % or lower, 18 wt % or lower, 19 wt % or lower, 20 wt % or lower, 21 wt % or lower, 22 wt % or lower, 23 wt % or lower, 24 wt % or lower, 25 wt % or lower, 26 wt % or lower, 27 wt % or lower, 28 wt % or lower, 29 wt % or lower, 30 wt % or lower, 3 wt % or lower, 32 wt % or lower, 33 wt % or lower, 34 wt % or lower, 35 wt % or lower, 36 wt % or lower, 37 wt % or lower, 38 wt % or lower, 39 wt % or lower, 40 wt % or lower, 41 wt % or lower, 42 wt % or lower, 43 wt % or lower, 44 wt % or lower, 45 wt % or lower, 46 wt % or lower, 47 wt % or lower, 48 wt % or lower, 49 wt % or lower, 50 wt % or lower, 51 wt % or lower, 52 wt % or lower, 53 wt % or lower, 54 wt % or lower, 55 wt % or lower, 56 wt % or lower, 57 wt % or lower, 58 wt % or lower, 59 wt % or lower, 60 wt % or lower, 61 wt % or lower, 62 wt % or lower, 63 wt % or lower, 64 wt % or lower, 65 wt % or lower, 66 wt % or lower, 67 wt % or lower, 68 wt % or lower, 69 wt % or lower, 70 wt % or lower, 71 wt % or lower, 72 wt % or lower, 73 wt % or lower, 74 wt % or lower, 75 wt % or lower, 76 wt % or lower, 77 wt % or lower, 78 wt % or lower, 79 wt % or lower, 80 wt % or lower.

In the present invention, the total amount of the carbon element is determined with the area of C1s peaks in the X-ray photoelectron spectroscopy $A_C^1$. The C1s peaks in the X-ray photoelectron spectroscopy are divided into two groups, i.e., the peak(s) in the range of 284.7-284.9 eV (corresponding to the graphite-type carbon substances) and the peak(s) in the range of 286.0-288.8 eV (corresponding to the non-graphite-type carbon substances). The area of the peak(s) in the range of 284.7-284.9 eV is named as $A_C^2$, and the area of the peak(s) in the range of 286.0-288.8 eV is named as $A_C^3$. The content of the carbon element determined with the peak(s) in the range of 284.7-284.9 eV in the X-ray photoelectron spectroscopy is $A_C^2/A_C^1$; and the total content of the carbon element, as determined with the peak(s) in the range of 286.0-288.8 eV in the X-ray photoelectron spectroscopy, is $A_C^3/A_C^1$.

In said heteroatom-containing nano-carbon material, the content of the carbon element as determined with the peak(s) in the range of 288.6-288.8 eV in the X-ray photoelectron spectroscopy is $I_C^c$, the content of the carbon element as determined with the peak(s) in the range of 286.0-286.2 eV in the X-ray photoelectron spectroscopy is $I_C^e$, $I_C^c/I_C^e$ is 0.2-1.

According to the present invention, the peaks corresponding to the carbon substances in the X-ray photoelectron spectroscopy are divided into two groups: the peaks corresponding to the graphite-type carbon substances and the peaks corresponding to the non-graphite-type carbon substances. For example, the peaks corresponding to the graphite-type carbon substances are in the range of 284.7-284.9 eV, the peaks corresponding to the non-graphite-type carbon substances are in the range of 286.0-288.8 eV.

According to the present invention, the peaks corresponding to non-graphite-type substances in the X-ray photoelectron spectroscopy are further divided into two groups, i.e., the peaks corresponding to hydroxy and ether-type carbon substances (i.e., the C—O containing groups) ($I_C^e$), and the peaks corresponding to carboxyl, anhydride and ester-type carbon substances (i.e., the C═O containing groups) ($I_C^c$).

For example, the peaks corresponding to hydroxy and ether-type carbon substances can be in the range of 286.0-286.2 eV, the peaks corresponding to carboxyl, anhydride and ester-type carbon substances can be in the range of 288.6-288.8 eV.

Again for example, the peaks corresponding to hydroxy and ether-type carbon substances can be in the range of 286.2-286.6 eV; the peaks corresponding to carboxyl, anhydride and ester-type carbon substances can be in the range of 288.6-289.0 eV.

Again for example, the peaks corresponding to hydroxy and ether-type carbon substances can be in the range of 286.21-286.61 eV; the peaks corresponding to carboxyl, anhydride and ester-type carbon substances can be in the range of 288.59-288.99 eV.

In an embodiment of the heteroatom-containing nano-carbon material according to the present invention, the ratio of the amount by mole of the carbon element corresponding to carboxyl, anhydride and ester-type carbon substances (i.e., the C═O containing groups) to the amount by mole of the carbon element corresponding to hydroxy and ether-type carbon substances (i.e., the C—O containing groups) is 1:(0.5-2), e.g. 1:0.5, 1:0.6, 1:0.9, 1:1, 1:1.1, 1:1.2, 1:1.3, 1:1.4, 1:1.5, 1:1.9, 1:2 and a numerical range formed by combining any two of the above point values. The amount by mole of the carbon element corresponding to carboxyl, anhydride and ester-type carbon substances (i.e., the C═O containing groups) and the amount by mole of the carbon element corresponding to hydroxy and ether-type carbon substances (i.e., the C—O containing groups) can be represented with the above peak ranges in the X-ray photoelectron spectroscopy of the heteroatom-containing nano-carbon material. For example, in the X-ray photoelectron spectroscopy of the heteroatom-containing nano-carbon material according to the present invention, the ratio of the signal value of the carbon in the range of 288.59-288.99 eV to the signal value of the carbon in the range of 286.21-286.61 eV is 1:(0.5-2) or 1:(1-2), for example 1:0.5, 1:0.6, 1:0.9, 1:1, 1:1.1, 1:1.2, 1:1.3, 1:1.4, 1:1.5, 1:1.9, 1:2 and a numerical range formed by combining any two of the above point values.

In said heteroatom-containing nano-carbon material, if the content of the nitrogen element is lower than 0.1 wt %, $I_C^c/I_C^e$ is preferably 0.3-0.9, more preferably 0.35-0.8, further preferably 0.5-0.7. In said heteroatom-containing nano-carbon material, if the content of the nitrogen element is 0.1 wt % or higher, $I_C^c/I_C^e$ is preferably 0.3-0.98, more preferably 0.45-0.95.

In the present invention, the peak(s) in the range of 286.0-288.8 eV in the X-ray photoelectron spectroscopy (corresponding to non-graphite carbon substances) are further divided into two groups, i.e., the peak(s) in the range of 286.0-286.2 eV (corresponding to hydroxy and ether-type carbon substances) and the peak(s) in the range of 288.6-

288.8 eV (corresponding to carboxyl, anhydride and ester-type carbon substances). The area of the peak(s) in the range of 286.0-286.2 eV is named as $A_C^4$, and the area of the peak(s) in the range of 288.6-288.8 eV is named as $A_C^5$. $I_C^c/I_C^e = A_C^5/A_C^4$.

If said heteroatom-containing nano-carbon material further contains a nitrogen element, the total content of the nitrogen element of said heteroatom-containing nano-carbon material as determined with the X-ray photoelectron spectroscopy is $I_N^t$, the content of the nitrogen element as determined with the peak(s) in the range of 398.5-400.1 eV in the X-ray photoelectron spectroscopy is $I_N^c$, $I_N^c/I_N^t$ is 0.7-1, preferably 0.8-0.95. According to the present invention, the heteroatom-containing nano-carbon material has a lower content of or even is free of the nitrogen element as determined with the peak(s) in the range of 400.6-401.5 eV in the X-ray photoelectron spectroscopy (i.e., graphite-type nitrogen). Generally, in the heteroatom-containing nano-carbon material according to the present invention, the content of the nitrogen element as determined with the peak(s) in the range of 400.6-401.5 eV in the X-ray photoelectron spectroscopy is $I_N^g$, and $I_N^g/I_N^t$ is lower than 0.3, and generally 0.05-0.2.

In the present invention, the total amount of the nitrogen element as determined with the area of the N1s peaks in the X-ray photoelectron spectroscopy is $A_N^1$. The N1s peaks in the X-ray photoelectron spectroscopy are divided into two groups, i.e., the peak(s) in the range of 400.6-401.5 eV (corresponding to graphite-type nitrogen substances) and the peak(s) in the range of 398.5-400.1 eV (corresponding to the nitrogen substances except the graphite-type nitrogen), and the areas for the two groups of peaks are determined. The area of the peak(s) in the range of 400.6-401.5 eV is named as $A_N^2$, and the area of the peak(s) in the range of 398.5-400.1 eV is named as $A_N^3$. $I_N^c/I_N^t = A_N^3/A_N^1$, $I_N^g/I_N^t = A_N^2/A_N^1$. If the resulting ratio is below 0.01, it is considered that said substance is absent, and the content of said substance is determined to be 0.

In the present invention, the location of each peak is determined with the binding energy that the peak top corresponds to. The peaks determined by the ranges as described hereinabove refer to those having binding energies that the peak tops correspond to being in said ranges. There may be only one peak or two or more peaks within said range. For example, the peak(s) in the range of 398.5-400.1 eV refer to all peaks having binding energies that the peak tops correspond to being in the range of 398.5-400.1 eV.

In a preferable embodiment of the present invention, based on the total weight of said heteroatom-containing nano-carbon material, the content of the oxygen element is 2-6 wt %, preferably 4-5.8 wt %, more preferably 4.5-5.5 wt %; the content of the nitrogen element is 0.2-1.8 wt %, preferably 0.8-1.6 wt %, more preferably 1-1.5 wt %; the content of the carbon element is 92.2-97.8 wt %, preferably 92.6-95.2 wt %, more preferably 93-94.5 wt %. $I_O^c/I_O^e$ is preferably 0.3-0.8, more preferably 0.35-0.8, further preferably 0.55-0.78. The content of the carbon element determined with the peak(s) in the range of 284.7-284.9 eV in the X-ray photoelectron spectroscopy is preferably 70-90 wt %, more preferably 75-85 wt %. $I_C^c/I_C^e$ is preferably 0.3-0.9, more preferably 0.4-0.7, further preferably 0.45-0.6. $I_N^c/I_N^t$ is preferably 0.7-0.98, more preferably 0.75-0.96, further preferably 0.8-0.95. The heteroatom-containing nano-carbon material according to the preferable embodiment is particularly suitable as the catalyst for dehydrogenation of butane (such as n-butane), which in particular has a relatively high selectivity for olefins, particularly butadiene.

In another preferable embodiment of the present invention, based on the total weight of said heteroatom-containing nano-carbon material, the content of the oxygen element is 2-6 wt %, preferably 3-5.5 wt %, more preferably 3.5-5 wt %; the content of the nitrogen element is 0.3-2 wt %, preferably 0.4-1.8 wt %, more preferably 0.5-1.5 wt %; the content of the carbon element is 92-97.7 wt %, preferably 92.7-96.6 wt %, more preferably 93.5-96 wt %. $I_O^c/I_O^e$ is preferably 0.3-0.8, more preferably 0.4-0.78, further preferably 0.45-0.75. The content of the carbon element determined with the peak(s) in the range of 284.7-284.9 eV in the X-ray photoelectron spectroscopy is preferably 70-90 wt %, more preferably 70-85 wt %. $I_C^c/I_C^e$ is preferably 0.3-0.9, more preferably 0.4-0.8, further preferably 0.45-0.6. $I_N^c/I_N^t$ is preferably 0.7-0.95, more preferably 0.7-0.9, further preferably 0.8-0.9. The heteroatom-containing nano-carbon material according to the preferable embodiment is particularly suitable as the catalyst for dehydrogenation of propane (such as n-propane), which in particular has a relatively high selectivity for C3-olefins.

In yet another preferable embodiment of the present invention, based on the total weight of said heteroatom-containing nano-carbon material, the content of the oxygen element is 3-6 wt %, preferably 4-5.8 wt %, more preferably 4.5-5.5 wt %; the content of the nitrogen element is 0.5-2 wt %, preferably 1-2 wt %, more preferably 1.2-1.8 wt %; the content of the carbon element is 92-96.5 wt %, preferably 92.2-95 wt %, more preferably 92.7-94.3 wt %. $I_O^c/I_O^e$ is preferably 0.3-0.8, more preferably 0.4-0.75, further preferably 0.6-0.7. The content of the carbon element determined with the peak(s) in the range of 284.7-284.9 eV in the X-ray photoelectron spectroscopy is preferably 70-80 wt %, more preferably 75-80 wt %. $I_C^c/I_C^e$ is preferably 0.4-0.98, more preferably 0.7-0.98, further preferably 0.85-0.95. $I_N^c/I_N^t$ is preferably 0.7-0.95, more preferably 0.75-0.9, further preferably 0.8-0.85. The heteroatom-containing nano-carbon material according to the preferable embodiment is particularly suitable as the catalyst for dehydrogenation of phenylethane, which in particular has a relatively high selectivity for phenylethene.

The heteroatom-containing nano-carbon material can be present in various common configurations, and can specifically include but is not limited to, a heteroatom-containing carbon nanotube, a heteroatom-containing graphene, a heteroatom-containing thin-layer graphite, a heteroatom-containing nano-carbon particle, a heteroatom-containing nano-carbon fiber, a heteroatom-containing nano-adamas, a heteroatom-containing fullerene and a combination thereof. Said heteroatom-containing carbon nanotube can be a heteroatom-containing single-walled carbon nanotube, a heteroatom-containing double-walled carbon nanotube, heteroatom-containing multi-walled carbon nanotube and a combination thereof. According to the present invention, the heteroatom-containing nano-carbon material is preferably a heteroatom-containing multi-walled carbon nanotube.

From the viewpoint of further improving the conversion of the starting material and the selectivity for the product, the heteroatom-containing multi-walled carbon nanotube preferably has a specific surface area of 50-500 m²/g, more preferably 80-300 m²/g, further preferably 100-200 m²/g. In the present invention, the specific surface area is determined with the nitrogen adsorption BET method. The heteroatom-containing multi-walled carbon nanotube has a weight loss difference $w_{800}$ in a temperature range of 400-800° C. and a weight loss difference $w_{500}$ in a temperature range of 400-500° C., $w_{500}/w_{800}$ is preferably 0.01-0.5, so that a better catalytic effect can be produced. More preferably, the heteroatom-containing multi-walled carbon nanotube has a weight loss difference $w_{800}$ in a temperature range of 400-800° C. and a weight loss difference $w_{500}$ in a temperature range of 400-500° C., $w_{500}/w_{800}$ is more preferably 0.02-0.2. In the present invention, $w_{800}=W_{800}-W_{400}$, $w_{500}=W_{500}-W_{400}$, $W_{400}$ is the weight loss measured at 400° C., $W_{800}$ is the weight loss measured at 800° C., $W_{500}$ is the weight loss measured at 500° C.; said weight loss is measured with a thermogravimetric analysis instrument in an air atmosphere, wherein the test initial temperature is 25° C., the temperature rise rate is 10° C./min; before the measurement, the sample is dried at 150° C. under 1 atm in a helium atmosphere for 3 hours.

In a preferable embodiment of the present invention, said heteroatom-containing nano-carbon material is preferably a heteroatom-containing multi-walled carbon nanotube, said heteroatom-containing multi-walled carbon nanotube preferably has a specific surface area of 50-500 m²/g, more preferably 80-300 m²/g, further preferably 100-200 m²/g; and $w_{500}/w_{800}$ is preferably 0.01-0.5, more preferably 0.02-0.2.

In said heteroatom-containing nano-carbon material, the contents of other non-metal heteroatoms, such as sulfur atom and phosphorus atom except for oxygen atom and nitrogen atom, can be conventional. Generally, in the heteroatom-containing nano-carbon material according to the present invention, the total amount of other non-metal heteroatoms (such as sulfur atom and phosphorus atom) except for oxygen atom and nitrogen atom can be 0.5 wt % or lower, preferably 0.2 wt % or lower, e.g. less than 0.1 wt %, less than 0.01 wt %, or less than 0.001 wt %. The heteroatom-containing nano-carbon material according to the present invention, except for the above metal elements, can further contain other metal atoms, said other metal atoms for example are derived from the catalyst for preparing the nano-carbon material. The content of said other metal atoms is generally 0.5 wt % or lower, preferably 0.2 wt % or lower, further preferably 0.1 wt % or lower, e.g. less than 0.05 wt %, less than 0.01 wt %, or less than 0.001 wt %.

According to the second aspect of the present invention, the present invention provides a process for preparing the heteroatom-containing nano-carbon material: placing a starting nano-carbon material dispersed in an aqueous dispersion in a close vessel to conduct a reaction, said aqueous dispersion optionally contains an organic base.

The dispersion medium in said aqueous dispersion can be water, or can be an aqueous solution containing at least one organic base.

According to the present invention, said aqueous dispersion is substantially free of an organic solvent. "Substantially free of an organic solvent" means being free of an organic solvent or the content of the organic solvent in the aqueous dispersion being less than 10 wt %, less than 9 wt %, less than 8 wt %, less than 7 wt %, less than 6 wt %, less than 5 wt %, less than 4 wt %, less than 3 wt %, less than 2 wt %, less than 1 wt %, less than 0.5 wt %, less than 0.1 wt %, less than 0.05 wt %, or less than 0.01 wt %. They organic solvent comprises aromatic hydrocarbons such as benzene, methylbenzene, and dimethylbenzene; aliphatic hydrocarbons such as pentane, hexane, and octane; alicyclic hydrocarbons such as cyclohexane, cyclohexanone, and methylbenzene-cyclohexanone; halogenated hydrocarbons such as chlorobenzene, dichlorobenzene, and dichloromethane; alcohols such as methanol, ethanol, and isopropanol; ethers such as diethylether, and propylene oxide; esters such as methyl acetate, ethyl acetate, and propyl acetate; ketones such as propanone, methylbutyl ketone, and methylisobutyl ketone; diol derivatives such as ethylene glycol monomethyl ether, ethylene glycol monoethyl ether, and ethylene glycol monobutyl ether; aldehydes such as formaldehyde; carbonitriles such as acetonitrile. According to the present invention, the organic solvent does not comprise said organic base according to the present invention.

In case that water is used as the dispersion medium of said aqueous dispersion, which can effectively control and/or increase the oxygen atom content of the starting nano-carbon material, the prepared heteroatom-containing nano-carbon material as the catalyst for dehydrogenation of hydrocarbons such as butane can effectively improve the catalytic capability. From the viewpoint of further improving the catalytic capability of the prepared heteroatom-containing nano-carbon material as the catalyst of the dehydrogenation of hydrocarbons, the weight ratio of the starting nano-carbon material to water is preferably 1:2-200, more preferably 1:5-100, further preferably 1:10-50. In addition, the amount of water can be adjusted based on the used organic base so that said organic base can be evenly dispersed in water.

In case the dispersion medium of said aqueous dispersion contains water and the organic base dissolved therein, the prepared heteroatom-containing nano-carbon material as the catalyst for dehydrogenation of hydrocarbons such as butane can produce a further improved catalytic capability. From the viewpoint of further improving the catalytic capability of the prepared heteroatom-containing nano-carbon material as the catalyst of the dehydrogenation of hydrocarbons, the weight ratio of the starting nano-carbon material to the organic base is preferably 1:0.05-20, more preferably 1:0.1-10, further preferably 0.5-5.

Said organic base is selected from the group consisting of an amine and a quaternary ammonium base.

Said quaternary ammonium base can particularly be a compound represented by formula I:

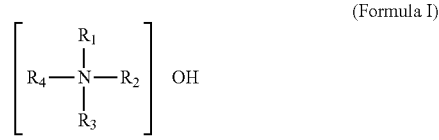

(Formula I)

In formula I, $R_1$, $R_2$, $R_3$ and $R_4$ can be each $C_1$-$C_{20}$alkyl (including linear $C_1$-$C_{20}$alkyl and branched $C_3$-$C_{20}$alkyl) or $C_6$-$C_{12}$aryl. The specific example for $C_1$-$C_{20}$alkyl may include but is not limited to at least one of methyl, ethyl, n-propyl, iso-propyl, n-butyl, sec-butyl, iso-butyl, tert-butyl, n-pentyl, neo-pentyl, iso-pentyl, tert-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-octadecyl and n-eicosyl. The specific example for $C_6$-$C_{12}$aryl can include but is not limited to phenyl, naphthyl, methylphenyl and ethylphenyl. Preferably, $R_1$, $R_2$, $R_3$ and $R_4$ are each $C_1$-$C_6$alkyl (including linear C1-C10alkyl and branched $C_3$-$C_{10}$alkyl). Further preferably, $R_1$, $R_2$, $R_3$ and $R_4$ are each $C_1$-$C_6$alkyl (including linear $C_1$-$C_6$alkyl and branched $C_3$-$C_6$alkyl).

Said amine can be a substance formed by replacing one, two or three hydrogens in an ammonia molecule with the corresponding number of organic group(s). Said organic group can be bonded to the nitrogen atom to form a cyclic group. Said organic group can be a substituted (e.g. with OH) or non-substituted aliphatic hydrocarbyl and/or a substituted (e.g. with OH) or non-substituted aromatic hydrocarbyl. Said aliphatic hydrocarbyl can be one, two or more of a substituted (e.g. with OH) or non-substituted saturated aliphatic chain hydrocarbyl, a substituted (e.g. with OH) or non-substituted unsaturated aliphatic chain hydrocarbyl, a substituted (e.g. with OH) or non-substituted saturated alicyclic hydrocarbyl, and a substituted (e.g. with OH) or non-substituted unsaturated alicyclic hydrocarbyl. Specifically, said amine can be one or two or more of a substituted (e.g. with OH) or non-substituted saturated aliphatic amine, a substituted (e.g. with OH) or non-substituted unsaturated aliphatic amine, a substituted (e.g. with OH) or non-substituted saturated alicyclic amine, a substituted (e.g. with OH) or non-substituted unsaturated alicyclic amine, a substituted (e.g. with OH) or non-substituted heterocyclic amine and a substituted (e.g. with OH) or non-substituted aromatic amine.

Said unsaturated aliphatic amine refers to an aliphatic chain amine containing an unsaturated group in the molecule structure. Said unsaturated group is preferably an alkenyl (i.e., —C═C—). The number of said unsaturated group and the amino group can be one or two or more respectively without a particular limitation.

According to the process of the present invention, the specific example foresaid organic base can include, but is not limited to one or more of methylamine, dimethylamine, trimethylamine, ethylamine, diethylamine, triethylamine, n-propylamine, di-n-propylamine, tri-n-propylamine, iso-propylamine, di-iso-propylamine, n-butylamine, di-n-butylamine, tri-n-butylamine, sec-butylamine, di-isobutylamine, tri-isobutylamine, tert-butylamine, n-pentylamine, di-n-pentylamine, tri-n-pentylamine, neo-pentylamine, iso-pentylamine, di-iso-pentylamine, tri-iso-pentylamine, tert-pentylamine, n-hexylamine, n-heptylamine, n-octylamine, n-nonylamine, n-decylamine, n-undecylamine, n-dodecylamine, dodecyldimethylamine, n-tridecylamine, n-tetradecylamine, n-pentadecylamine, n-hexadecylamine, monoethanolamine, triethanolamine, tri-isopropanolamine, diethanolamine, di-n-propanolamine, tri-n-propanolamine, di-n-butanolamine, tri-n-butanolamine, dodecyl-dimethylamine, tetradecyl-dimethylamine, hexadecyl-dimethylamine, ethylene diamine, propylene diamine, butylene diamine, pentylene diamine, hexylene diamine, a substituted or unsubstituted pyrrole, a substituted or unsubstituted tetrahydropyrrole, a substituted or unsubstituted pyridine, a substituted or unsubstituted hexahydropyridine, a substituted or unsubstituted imidazole, a substituted or unsubstituted pyrazole, a substituted or unsubstituted quinoline, a substituted or unsubstituted dihydroquinoline, a substituted or unsubstituted tetrahydroquinoline, a substituted or unsubstituted decahydroquinoline, a substituted or unsubstituted isoquinoline, a substituted or unsubstituted pyrimidine, aniline, diphenylamine, biphenylamine, o-phenylene diamine, m-phenylene diamine, p-phenylene diamine, o-methylaniline, m-methylaniline, p-methylaniline, 2,3-dimethylaniline, 2,4-dimethylaniline, 2,5-dimethylaniline, 2,6-dimethylaniline, 3,4-dimethylaniline, 3,5-dimethylaniline, 2,4,6-trimethylaniline, o-ethylaniline, N-butylaniline, 2,6-diethylaniline, cyclohexylamine, cyclopentylamine, hexamethylenetetramine, dietheylene triamine, triethylene tetraamine, tetramethylammonium hydroxide, tetra-ethylammonium hydroxide, tetrapropyl ammonium hydroxide (including various isomers thereof, e.g. tetra-n-propylammonium hydroxide and tetra-isopropylammonium hydroxide), tetrabutylammonium hydroxide (including its isomers, e.g. tetra-n-butylammonium hydroxide, tetra-sec-butylammonium hydroxide, tetra-isobutylammonium hydroxide and tetra-tert-butylammonium hydroxide) and tetra-pentylammonium hydroxide (including various isomers thereof).

According to the process of the present invention, said amine is preferably one or more of a compound represented by formula II, a compound represented by formula III, and a substance represented by general formula $R_{12}(NH_2)_2$,

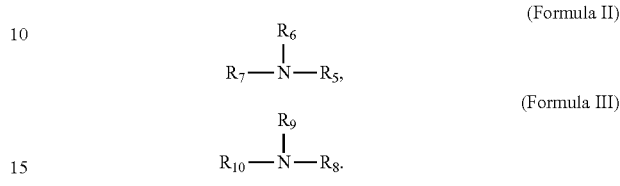

(Formula II)

(Formula III)

In the formula II, $R_5$, $R_6$ and $R_7$ are each H, $C_1$-$C_6$alkyl or $C_6$-$C_{12}$aryl, and $R_5$, $R_6$ and $R_7$ are not H at the same time. In the present invention, the specific example for $C_1$-$C_6$alkyl may include but is not limited to: methyl, ethyl, n-propyl, iso-propyl, n-butyl, sec-butyl, iso-butyl, tert-butyl, n-pentyl, iso-pentyl, tert-pentyl, neo-pentyl and n-hexyl. In the present invention, the specific example for $C_6$-$C_{12}$aryl includes but is not limited to phenyl, naphthyl, methylphenyl and ethylphenyl.

In the formula III, $R_8$, $R_9$ and $R_{10}$ are each —$R_{11}$OH or hydrogen, and at least one of $R_8$, $R_9$ and $R_{10}$ is —$R_{11}$OH, $R_{11}$ is $C_1$-$C_4$alkylene. In the present invention, $C_1$-$C_4$alkylene includes linear C1-C4alkylene and branched C3-C4alkylene, and its specific example may include but is not limited to: methylene, ethylene, n-propylene, iso-propylene, n-butylene, iso-butylene and tert-butylene.

In the formula $R_{12}(NH_2)_2$, $R_{12}$ can be $C_1$-$C_6$alkylene or $C_6$-$C_{12}$arylene. In the present invention, C1-C6alkylene includes linear $C_1$-$C_6$alkylene and branched $C_3$-$C_6$alkylene, and its specific example may include but is not limited to: methylene, ethylene, n-propylene, iso-propylene, n-butylene, iso-butylene, tert-butylene, n-pentylene and n-hexylene. In the present invention, the specific example for $C_6$-$C_{12}$arylene includes but is not limited to phenylene and naphthalene.

The reaction condition is configured so as to sufficiently increase the contents of the oxygen atom and the nitrogen atom for the starting nano-carbon material. Preferably, said aqueous dispersion is maintained at 80-220° C. in the reaction. If the temperature of said aqueous dispersion is within the above range, not only the contents of the contents of the oxygen atom and/or the nitrogen atom can be effectively increased, but also the structural form of the starting nano-carbon material will not be remarkably effected. More preferably, said aqueous dispersion is maintained at 120-180° C. in the reaction.

Said reaction can be maintained for a period depending on the reaction temperature so that a sufficient amount of the oxygen atom and/or the nitrogen atom can be introduced to the starting nano-carbon material. Generally, said reaction can be maintained for a period of 0.5-96 hours, preferably 2-72 hours, more preferably 20-50 hours.

In a preferable embodiment, said organic base is a quaternary ammonium base represented by formula I, preferably one or more of tetramethylammonium hydroxide, tetraethylammonium hydroxide, tetrapropyl ammonium hydroxide, tetrabutylammonium hydroxide and tetrapentylammonium hydroxide. The prepared heteroatom-containing nano-carbon material is particularly suitable as the catalyst for dehydrogenation of butane, and a relatively high butadiene selectivity can be obtained. In this preferable embodiment, the weight ratio of the starting nano-carbon material to the organic base is preferably 1:0.1-10, more preferably 0.5-5. In this preferable embodiment, the temperature of the aqueous dispersion is maintained at 90-210° C., more preferably 140-180° C. in the reaction.

In another preferable embodiment, said organic base is an ethanolamine represented by formula III, preferably one or more of monoethanolamine, diethanolamine and triethanolamine, the prepared heteroatom-containing nano-carbon material is particularly suitable as the catalyst for dehydrogenation of propane, and a relatively high propylene selectivity can be obtained. In this preferable embodiment, the weight ratio of the starting nano-carbon material to the organic base is preferably 1:0.2-10, more preferably 1:1-5. The temperature of the aqueous dispersion is maintained at 90-160° C., more preferably 120-150° C. in the reaction.

In yet another preferable embodiment, said organic base is a substance represented by general formula $R_{12}(NH_2)_2$, preferably one or more of ethylene diamine, propylene diamine, butylene diamine, pentylene diamine and hexylene diamine, the prepared heteroatom-containing nano-carbon material is particularly suitable as the catalyst for dehydrogenation of phenylethane, and a relatively high phenylethene selectivity can be obtained. In this preferable embodiment, the weight ratio of the starting nano-carbon material to the organic base is preferably 1:0.2-10, more preferably 1:1-5. The temperature of the aqueous dispersion is preferably 100-200° C., more preferably 120-150° C. in the reaction.

Said aqueous dispersion can be formed by various conventional methods. For Example, the starting nano-carbon material can be dispersed in water (preferably deionized water), and then said organic base can be optionally added to obtain said aqueous dispersion. In order to further improve the dispersion effect of the starting nano-carbon material and reduce the dispersing time, the ultrasonic oscillation can be used to disperse the starting nano-carbon material in water. The condition of said ultrasonic oscillation can be conventionally selected. Generally, the frequency for said ultrasonic oscillation can be 10-100 kHz, preferably 40-80 kHz, the period for said ultrasonic oscillation can be 0.1-6 hours, preferably 0.5-2 hours. According to the process of the present invention, said organic base preferably is provided in form of a solution (preferably an aqueous solution).

The contents of the oxygen element and the nitrogen element in said starting nano-carbon material are not particularly limited, and can be conventionally selected. Generally, in said starting nano-carbon material, the content of the oxygen element is lower than 1.2 wt %, preferably lower than 0.5 wt %; the content of the nitrogen element is lower than 0.1 wt %, preferably lower than 0.08 wt %, more preferably lower than 0.05 wt %. In said starting nano-carbon material, the total amount of other non-metal heteroatoms except for the oxygen atom and the nitrogen atom (such as the phosphorus atom and the sulfur atom)(calculated as element) can be the conventional contents. Generally, in said starting nano-carbon material, the total amount of other non-metal heteroatoms except for the oxygen atom and the nitrogen atom is lower than 0.5 wt %, preferably lower than 0.2 wt %, more preferably lower than 0.1 wt %, further preferably lower than 0.05 wt %. Said starting nano-carbon material, depending on the sources, can further contain some metal elements, for example, those from the metal elements present in the catalyst that is used in the preparation of the starting nano-carbon material. In said starting nano-carbon material, the contents of metal elements (calculated as element) are generally 2.5 wt % or lower, preferably 2 wt % or lower, more preferably 1 wt % or lower, further preferably 0.5 wt % or lower.

According to the process of the present invention, the starting nano-carbon material, before use, can be pre-treated in a conventional manner (e.g. washing), to remove some impurities on the surface of the starting nano-carbon material; or can be directly used without the pretreatment. In the examples disclosed in the present invention, the used starting nano-carbon materials are directly used without any pretreatment.

According to the process for preparing the heteroatom-containing nano-carbon material of the present invention, various forms of nano-carbon materials can be treated to increase the contents of the oxygen atom and/or the nitrogen atom in the nano-carbon material. Said starting nano-carbon material can include but is not limited to carbon nanotube, graphene, nano-adamas, thin-layer graphite, nano-carbon particle, nano-carbon fiber, fullerene and a combination thereof. Said carbon nanotube can be a single-walled carbon nanotube, a double-walled carbon nanotube, a multi-walled carbon nanotube and a combination thereof. Preferably, said starting nano-carbon material is a carbon nanotube, more preferably a multi-walled carbon nanotube.

According to the process for preparing the heteroatom-containing nano-carbon material of the present invention, in a preferable embodiment, said starting nano-carbon material is a multi-walled carbon nanotube, said multi-walled carbon nanotube has a specific surface area of 20-500 $m^2/g$, preferably 50-400 $m^2/g$, more preferably 90-300 $m^2/g$, further preferably 100-200 $m^2/g$. If the specific surface area of said multi-walled nano-carbon material is within the above range, the prepared heteroatom-containing nano-carbon material has a better catalytic activity.

According to the process for preparing the heteroatom-containing nano-carbon material of the present invention, in case that said starting nano-carbon material is a multi-walled carbon nanotube, said multi-walled carbon nanotube has a weight loss difference $w_{800}$ in a temperature range of 400-800° C. and a weight loss difference $w_{800}$ in a temperature range of 400-500° C., $w_{500}/w_{800}$ is preferably 0.01-0.5, more preferably 0.02-0.2. The prepared heteroatom-containing nano-carbon material shows a better catalytic effect.

In a further preferable embodiment of the present invention, said starting nano-carbon material is a multi-walled carbon nanotube, said multi-walled carbon nanotube has a specific surface area of 20-500 $m^2/g$, preferably 50-400 $m^2/g$, more preferably 90-300 $m^2/g$, further preferably 100-200 $m^2/g$; said multi-walled carbon nanotube has a weight loss difference $w_{800}$ in a temperature range of 400-800° C. and a weight loss difference $w_{800}$ in a temperature range of 400-500° C., $w_{500}/w_{800}$ is preferably 0.01-0.5, more preferably 0.02-0.2.

Said reaction is conducted in a close vessel. Said reaction can be conducted under an autogenous pressure (i.e., an extra pressure is unnecessary), or under a pressurized condition. Preferably, said reaction is conducted under an autogenous pressure. Said close vessel can be a common reactor that can accomplish the sealing and the heating, such as a high pressure reaction vessel.

The process for preparing the heteroatom-containing nano-carbon material according to the present invention can further comprise separating a solid substance from the mixture obtained from the reaction, and drying and optionally calcining the separated solid substance, to produce said heteroatom-containing nano-carbon material.

A conventional solid-liquid separation method can be used to separate a solid substance from the mixture obtained from the reaction, e.g. centrifugation, filtration, decantation and a combination thereof.

The drying condition can be conventionally selected, so that the volatile substances can be removed from the separated solid substance. Generally, said drying can be conducted at 50-200° C., preferably 80-180° C., more preferably 100-150° C. Said drying can be conducted for a period, depending on the drying temperature and the drying manner. Generally, said drying can be conducted for a period of 0.5-48 hours, preferably 3-24 hours, more preferably 5-12 hours. Said drying can be conducted under a normal pressure (1 atm), or a reduced pressure. From the viewpoint of further improving the drying efficiency, said drying is preferably conducted under a reduced pressure.

The process for preparing the heteroatom-containing nano-carbon material according to the present invention can effectively increase the contents of the oxygen atom and/or the nitrogen atom in the starting nano-carbon material, and will not have a remarkable influence on the structural form of the starting nano-carbon material.

According to the third aspect of the present invention, the present invention provides a heteroatom-containing nano-carbon material prepared with the process of the present invention.

According to the fourth aspect of the present invention, the present invention provides a heteroatom-containing nano-carbon material, wherein said heteroatom-containing nano-carbon material is produced by calcining the heteroatom-containing nano-carbon material according to the first aspect of the present invention or the heteroatom-containing nano-carbon material according to the present invention (e.g. uncalcined).

Said calcination can be conducted in a conventional condition. Generally, said calcination can be conducted at 250-500° C., preferably at 300-480° C., more preferably 350-450° C. Said calcination can be conducted for a period, depending on the calcination temperature. Generally, said calcination can be conducted for a period of 1-24 hours, preferably 2-12 hours, more preferably 2-8 hours. Said calcination can be conducted in an oxygen-containing atmosphere or in an inert atmosphere. Said oxygen-containing atmosphere can be an air atmosphere; or can be a mixed atmosphere consisting of oxygen and an inert gas. In said mixed atmosphere, the content of oxygen can be 0.1-22 vol %. Said inert atmosphere can be an atmosphere formed from a noble gas (such as argon and/or helium). From the viewpoint of convenience and cost, said calcination is preferably conducted in an oxygen-containing atmosphere (e.g. an air atmosphere).

The heteroatom-containing nano-carbon material according to the present invention or the heteroatom-containing nano-carbon material prepared with the present preparation method has a good catalytic capability, and particularly shows a relatively high catalytic activity in the dehydrogenation of hydrocarbons.

The heteroatom-containing nano-carbon material according to the present invention or the heteroatom-containing nano-carbon material prepared with the present preparation method can be directly used as the catalyst, or can be used in form of a shaped catalyst. Said shaped catalyst can contain the heteroatom-containing nano-carbon material according to the present invention or the heteroatom-containing nano-carbon material prepared with the present preparation method and a binder. Said binder can be selected based on the specific environments in which the shaped catalyst is used, in order to satisfy the use requirement. For example, the binder can be an organic binder and/or an inorganic binder. Said organic binder can be various common polymer-type binders. Said inorganic binder can be various common thermostable inorganic oxides, such as alumina and/or silica. In case that said shaped catalyst is a shaped catalyst that has a catalytic capability in the dehydrogenation, e.g. the direct dehydrogenation and the oxidation dehydrogenation, in particular the oxidation dehydrogenation of hydrocarbons, said binder is preferably an inorganic binder. In said shaped catalyst, the content of the heteroatom-containing nano-carbon material can be selected based on the specific use requirements, and is not particularly limited. Generally, based on the total amount of said shaped catalyst, the content of said heteroatom-containing nano-carbon material can be 5-95 wt %.

According to the fifth aspect of the present invention, the present invention provides use of the heteroatom-containing nano-carbon material according to the first aspect of the present invention, the heteroatom-containing nano-carbon material according to the third aspect of the present invention, or the heteroatom-containing nano-carbon material according to the fourth aspect of the present invention as the catalyst of the dehydrogenation of hydrocarbons.

According to the use of the present invention, said heteroatom-containing nano-carbon material can be directly used in the dehydrogenation of hydrocarbons, or can be used in the dehydrogenation of hydrocarbons after shaping. Said dehydrogenation can be conducted in the presence or absence of oxygen. Preferably, said dehydrogenation is conducted in the presence of oxygen gas, in order to produce a better catalytic effect.

According to the sixth aspect of the present invention, the present invention provides a process for dehydrogenation of hydrocarbons, which process comprises, in presence or absence of oxygen, in the condition for dehydrogenation of hydrocarbons, contacting the hydrocarbons with the heteroatom-containing nano-carbon material according to the first aspect of the present invention, the heteroatom-containing nano-carbon material according to the third aspect of the present invention, or the heteroatom-containing nano-carbon material according to the fourth aspect of the present invention.

In the process for dehydrogenating the hydrocarbon according to the present invention, said heteroatom-containing nano-carbon material can be directly used as the catalyst, or can be used in form of a shaped catalyst. Said shaped catalyst can contain the heteroatom-containing nano-carbon material according to the present invention or the heteroatom-containing nano-carbon material prepared with the present preparation method and a binder. Said binder can be selected based on the specific environments in which the shaped catalyst is used, in order to satisfy the use requirement. For example, the binder can be an organic binder and/or an inorganic binder. Said organic binder can be various common polymer-type binders. Said inorganic binder can be various common thermostable inorganic oxides, such as alumina and/or silica. In case that said shaped catalyst is a shaped catalyst that has a catalytic capability in the dehydrogenation, e.g. the direct dehydrogenation and the oxidation dehydrogenation, in particular the oxidation dehydrogenation of hydrocarbons, said binder is preferably an inorganic binder. In said shaped catalyst, the content of the heteroatom-containing nano-carbon material can be selected based on the specific use requirements, and is not particularly limited. Generally, based on the total amount of said shaped catalyst, the content of said heteroatom-containing nano-carbon material can be 5-95 wt %.

According to the process for dehydrogenating the hydrocarbon of the present invention, various types of hydrocarbons can be dehydrogenated to produce unsaturated hydrocarbons, such as olefins. The process according to the present invention is particularly suitable for the dehydrogenation of alkanes to produce olefins. Preferably, said hydrocarbon is an alkane such as $C_2$-$C_{12}$ alkanes. Specifically, said hydrocarbon can include but is not limited to one or more of ethane, propane, n-butane, iso-butane, n-pentane, iso-pentane, neo-pentane, cyclopentane, n-hexane, 2-methylpentane, 3-methylpentane, 2,3-dimethylbutane, cyclohexane, methylcyclopentane, n-heptane, 2-methylhexane, 3-methylhexane, 2-ethylpentane, 3-ethylpentane, 2,3-dimethylpentane, 2,4-dimethylpentane, n-octane, 2-methylheptane, 3-methylheptane, 4-methylheptane, 2,3-dimethylhexane, 2,4-dimethylhexane, 2,5-dimethylhexane, 3-ethylhexane, 2,2,3-trimethylpentane, 2,3,3-trimethylpentane, 2,4,4-trimethylpentane, 2-methyl-3-ethylpentane, n-nonane, 2-methyloctane, 3-methyloctane, 4-methyloctane, 2,3-dimethylheptane, 2,4-dimethylheptane, 3-ethylheptane, 4-ethylheptane, 2,3,4-trimethylhexane, 2,3,5-trimethylhexane, 2,4,5-trimethylhexane, 2,2,3-trimethylhexane, 2,2,4-trimethylhexane, 2,2,5-trimethylhexane, 2,3,3-trimethylhexane, 2,4,4-trimethylhexane, 2-methyl-3-ethylhexane, 2-methyl-4-ethylhexane, 3-methyl-3-ethylhexane, 3-methyl-4-ethylhexane, 3,3-diethylpentane, 1-methyl-2-ethylcyclohexane, 1-methyl-3-ethylcyclohexane, 1-methyl-4-ethylcyclohexane, n-propylcyclohexane, iso-propylcyclohexane, trimethylcyclohexane (including the isomers of trimethylcyclohexane, such as 1,2,3-trimethylcyclohexane, 1,2,4-trimethylcyclohexane, 1,2,5-trimethylcyclohexane, and 1,3,5-trimethylcyclohexane), n-decane, 2-methylnonane, 3-methylnonane, 4-methylnonane, 5-methylnonane, 2,3-dimethyloctane, 2,4-dimethyloctane, 3-ethyloctane, 4-ethyloctane, 2,3,4-trimethylheptane, 2,3,5-trimethylheptane, 2,3,6-trimethylheptane, 2,4,5-trimethylheptane, 2,4,6-trimethylheptane, 2,2,3-trimethylheptane, 2,2,4-trimethylheptane, 2,2,5-trimethylheptane, 2,2,6-trimethylheptane, 2,3,3-trimethylheptane, 2,4,4-trimethylheptane, 2-methyl-3-ethylheptane, 2-methyl-4-ethylheptane, 2-methyl-5-ethylheptane, 3-methyl-3-ethylheptane, 4-methyl-3-ethylheptane, 5-methyl-3-ethylheptane, 4-methyl-4-ethylheptane, 4-propylheptane, 3,3-diethylhexane, 3,4-diethylhexane, 2-methyl-3,3-diethylpentane, phenylethane, 1-phenylpropane, 2-phenylpropane, 1-phenylbutane, 2-phenylbutane, 1-phenylpentane, 2-phenylpentane and 3-phenylpentane. More preferably, said hydrocarbon is one or more of propane, n-butane, iso-butane and phenylethane.

According to the process for dehydrogenating the hydrocarbon of the present invention, said reaction can be conducted in the presence of oxygen gas (i.e., the starting material containing hydrocarbons further contains oxygen gas), or in the absence of oxygen gas (i.e., the starting material containing hydrocarbons does not contain oxygen gas). Preferably, the process for dehydrogenating the hydrocarbon according to the present invention is conducted in the presence of oxygen gas. In case that the process of the present invention is conducted in the presence of oxygen gas, the used amount of oxygen gas can be conventionally selected. Generally, the mole ratio of hydrocarbon to oxygen can be 0.01-100:1, preferably 0.1-10:1, more preferably 0.2-5:1, most preferably 0.3-2:1.

According to the process for dehydrogenating the hydrocarbon of the present invention, hydrocarbons and oxygen gas can be fed to the reactor with a carrier gas to contact with the heteroatom-containing nano-carbon material to conduct the reaction. In this case, the starting material containing hydrocarbons can further contain the carrier gas. Said carrier gas can be such a gas that will not react with the reactant and the product in the reaction condition and will not decompose in the reaction condition, e.g. nitrogen, $CO_2$, a noble gas, water vapor and a combination thereof. The used amount of said carrier gas can be conventionally selected. Generally, based on the total weight of the starting material, the content of the carrier gas can be 30-99.5 vol %, preferably 50-99 vol %, more preferably 70-98 vol %.

According to the process for dehydrogenating the hydrocarbon of the present invention, the contacting of the starting material containing hydrocarbons and optionally oxygen gas with the heteroatom-containing nano-carbon material can be conducted in a fixed bed reactor or in a fluidized bed reactor without a particular limitation. Preferably, said contacting is conducted in a fixed bed reactor.

According to the process for dehydrogenating the hydrocarbon of the present invention, the contacting of the starting material containing hydrocarbons and optionally oxygen gas with the heteroatom-containing nano-carbon material can be conducted at a conventional temperature so that the dehydrogenation of hydrocarbons occurs. Generally, said contacting can be conducted at 200-650° C., preferably 300-600° C., more preferably 350-500° C. Said contacting can be conducted under 0-10 MPa, preferably 0.01-6 MPa, more preferably 0.02-3 MPa, further preferably 0.05-1.5 MPa. In the present invention, the pressure is the gauge pressure.

Said contacting can be conducted for a period, depending on the contacting temperature. Specifically, in case that the dehydrogenation is conducted in the fixed bed reactor, the contacting time can be represented by the gas hourly space velocity by volume of the starting material. Generally, the gas hourly space velocity by volume of the starting material can be 0.1-10000 $h^{-1}$, preferably 1-6000 $h^{-1}$, more preferably 5-4000 $h^{-1}$, further preferably 10-1000 $h^{-1}$, e.g. 100-500 $h^{-1}$.

The dehydrogenation process according to the present invention can be optimized for the reaction conditions according to the hydrocarbons to be dehydrogenated so as to accomplish a better reaction effect.

The present invention will be further illustrated with the examples, which is not intended to limit the scope of the present invention in any way.

In the following Examples and Comparative Examples, the X-ray photoelectron spectroscopy analysis was carried out with an ESCALab250 type X-ray photoelectron spectroscoper equipped with Thermo Advantage V5.926 software (Thermo Scientific Company), wherein the excitation source was a monochromatic Al Kα X-ray, the energy was 1486.6 eV, the power was 150 W, and the pass energy for narrow scan was 30 eV. The basis vacuum for analysis and test was $6.5 \times 10^{-10}$ mbar. The electron binding energy was corrected with the C1s peak (284.0 eV) of the simple substance of carbon. The data was treated with the Thermo Advantage software. The quantitative analysis was carried out in the analysis module with the sensitivity factor method. The samples were dried for 3 hours at 150° C. and 1 atm in a helium atmosphere before the test.

In the following Examples and Comparative Examples, the thermogravimetric analysis was conducted with the TA5000 thermal analyzer. The test conditions included an air atmosphere, a temperature rising speed of 10° C./min, and a temperature range of room temperature (25° C.) to 1000° C. The samples were dried for 3 hours at 150° C. and 1 atm in a helium atmosphere before the test. The specific surface area was measured with ASAP 2000-type N2 physical adsorption analyzer (Micromertrics Company, USA). The microstructures of the starting nano-carbon material and the heteroatom-containing nano-carbon material were observed with a high resolution transmission electron microscopy (FEI Company, USA).

Preparation Examples 1-47 are provided to illustrate the preparation of the heteroatom-containing nano-carbon material.

Preparation Example 1

(1) 20 g of a multi-walled carbon nanotube (it had a specific surface area of 136 m$^2$/g, an oxygen atom content of 0.3 wt %, a nitrogen atom content of 0.02 wt %, a total content of other non-metal heteroatoms except the nitrogen atom and the oxygen atom (phosphorus atom and sulfur atom) of 0.01 wt %, a total content of metal atoms of 0.2 wt %; the weight loss difference in a temperature range of 400-800° C. was $w_{800}$, the weight loss difference in a temperature range of 400-500° C. was $w_{500}$, and $w_{500}/w_{800}$ was 0.12; and it was commercially available from Chengdu Organic Chemicals Co. Ltd., Chinese Academy of Sciences), used as the starting nano-carbon material, was dispersed in 300 g deionized water to obtain an aqueous dispersion, wherein the dispersing was conducted in an ultrasonic oscillation condition, the ultrasonic oscillation condition included: 40 kHz (frequency) and 2 hours (time).

(2) The obtained aqueous dispersion was placed in a high-pressure reaction vessel having an inner lining of polytetrafluoroethylene, and reacted at a temperature of 140° C. under an autogenous pressure for 48 hours. After the completion of reaction, the temperature of the high pressure reaction vessel dropped to room temperature, the reaction vessel was opened, the reaction mixture was filtered and washed, and the solid substance was collected. The collected solid substance was dried under the normal pressure (1 atm, the same below) at 120° C. for 12 hours to produce the heteroatom-containing nano-carbon material. The composition, the specific surface area and w500/w800 of said heteroatom-containing nano-carbon material were listed in Table 1.

Figure 2:
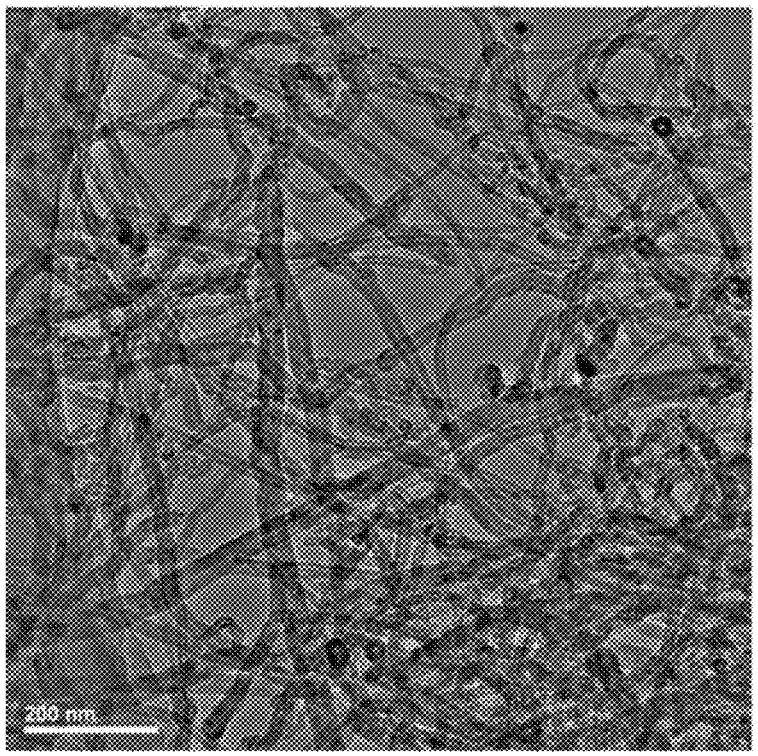
FIG. 2 shows a transmission electron microscope photo of the nano-carbon material used as the starting material in Preparation Example 1.

FIG. 1 was the transmission electron microscope photo of the prepared heteroatom-containing nano-carbon material, and FIG. 2 was the transmission electron microscope photo of the multi-walled carbon nanotube as the starting material. It could be seen from FIG. 1 and FIG. 2 that the heteroatom-containing nano-carbon material had a good microstructure, indicating that the reaction process had little effect on the structure of the nano-carbon material.

Comparative Preparation Example 1

The same aqueous dispersion as that of Preparation Example 1 was placed in a three-neck flask equipped with a condenser pipe. The three-neck flask was placed in an oil bath of 140° C. The reaction was conducted at normal pressure under reflux for 48 hours. After the completion of reaction, the contents in the three-neck flask were cooled to room temperature, the reaction mixture was filtered and washed, and the solid substance was collected. The collected solid substance was dried under the normal pressure at 120° C. for 6 hours to produce the heteroatom-containing nano-carbon material. The composition and the properties of the prepared heteroatom-containing nano-carbon material were listed in Table 1.

Preparation Example 2

The heteroatom-containing nano-carbon material was prepared by using the same process as that of Preparation Example 1 except that in Step (1), the multi-walled carbon nanotube as the starting nano-carbon material (commercially available from Shandong Dazhan Nano Material Co. Ltd.) had a specific surface area of 251 m$^2$/g, the weight loss difference in a temperature range of 400-800° C. was $w_{800}$, the weight loss difference in a temperature range of 400-500° C. was $w_{500}$, and $w_{500}/w_{800}$ was 0.33, the oxygen atom content was 0.62 wt %, the nitrogen atom content was 0.01 wt %, the total content of other non-metal heteroatoms except the nitrogen atom and the oxygen atom (phosphorus atom and sulfur atom) was 0.01 wt %, and the total content of metal atoms was 0.08 wt %. The composition and the properties of the prepared heteroatom-containing nano-carbon material were listed in Table 1.

Preparation Example 3

The heteroatom-containing nano-carbon material was prepared by using the same process as that of Preparation Example 1 except that, in Step (2), the obtained aqueous dispersion was placed in a high-pressure reaction vessel having an inner lining of polytetrafluoroethylene, and reacted at a temperature of 90° C. under an autogenous pressure for 48 hours. The composition and the properties of the prepared heteroatom-containing nano-carbon material were listed in Table 1.

Preparation Example 4

(1) 20 g of a multi-walled carbon nanotube (it had a specific surface area of 183 m$^2$/g, an oxygen atom content of 0.2 wt %, a nitrogen atom of was 0.01 wt %, a total content of other non-metal heteroatoms except the nitrogen atom and the oxygen atom (phosphorus atom and sulfur atom) of 0.04 wt %, a total content of metal atoms of 0.03 wt %; the weight loss difference in a temperature range of 400-800° C. was $w_{800}$, the weight loss difference in a temperature range of 400-500° C. was $w_{500}$, and $w_{500}/w_{800}$ was 0.07; and it was commercially available from Chengdu Organic Chemicals Co. Ltd., Chinese Academy of Sciences), used as the starting nano-carbon material, was dispersed in 500 g deionized water to obtain an aqueous dispersion, wherein the dispersing was conducted in an ultrasonic oscillation condition, the ultrasonic oscillation condition included: 80 kHz (frequency) and 0.5 hours (time).

(2) The obtained aqueous dispersion was placed in a high-pressure reaction vessel having an inner lining of polytetrafluoroethylene, and reacted at a temperature of 180° C. under an autogenous pressure for 24 hours. After the completion of reaction, the temperature of the high pressure reaction vessel dropped to room temperature, the reaction vessel was opened, the reaction mixture was filtered and washed, and the solid substance was collected. The collected solid substance was dried under the normal pressure at 120° C. for 12 hours to produce the heteroatom-containing nano-carbon material. The composition and the properties of said heteroatom-containing nano-carbon material were listed in Table 1.

Comparative Preparation Example 2

The same aqueous dispersion as that of Preparation Example 4 was placed in a three-neck flask equipped with a condenser pipe. The three-neck flask was placed in an oil bath of 100° C. The reaction was conducted at normal pressure under reflux for 24 hours. After the completion of reaction, the contents in the three-neck flask were cooled to room temperature, the reaction mixture was filtered and washed, and the solid substance was collected. The collected solid substance was dried under the normal pressure at 120° C. for 6 hours to produce the heteroatom-containing nano-carbon material. The composition and the properties of the prepared heteroatom-containing nano-carbon material were listed in Table 1.

Preparation Example 5

The heteroatom-containing nano-carbon material was prepared by using the same process as that of Preparation Example 4 except that in Step (1), the multi-walled carbon nanotube as the starting nano-carbon material (commercially available from Shandong Dazhan Nano Material Co. Ltd.) had a specific surface area of 103 m$^2$/g, $w_{500}/w_{800}$ was 0.23, the oxygen atom content was 1.1 wt %, the nitrogen atom content was 0.03 wt %, the total content of other non-metal heteroatoms (P and S) except N and O was 0.01 wt %, and the total content of metal atoms was 1.6 wt %. The composition and the properties of the prepared heteroatom-containing nano-carbon material were listed in Table 1.

Preparation Example 6

The heteroatom-containing nano-carbon material was prepared by using the same process as that of Preparation Example 4 except that, in Step (2), the obtained aqueous dispersion was placed in a high-pressure reaction vessel having an inner lining of polytetrafluoroethylene, and reacted under an autogenous pressure at 210° C. for 24 hours. The composition and the properties of the prepared heteroatom-containing nano-carbon material were listed in Table 1.

Preparation Example 7

Figure 3:
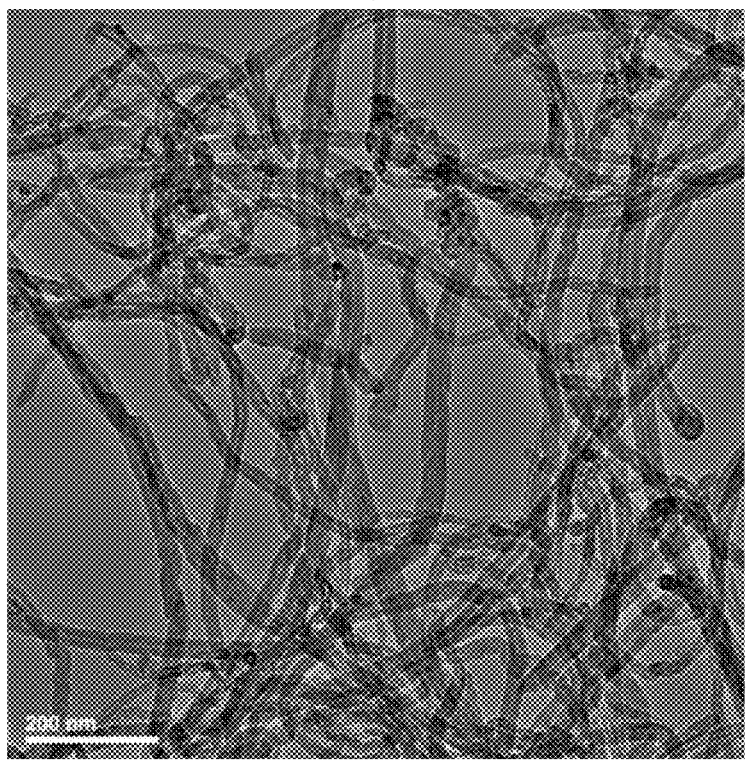
FIG. 3 shows a transmission electron microscope photo of the heteroatom-containing nano-carbon material prepared according to Preparation Example 7.

The heteroatom-containing nano-carbon material was prepared by using the same process as that of Preparation Example 1 except that in Step (1), the starting nano-carbon material was dispersed in deionized water, and then added tetrapropyl ammonium hydroxide (as a 25 wt % aqueous solution), wherein the weight ratio of the starting nano-carbon material to tetrapropyl ammonium hydroxide was 1:0.75. The composition and the properties of the prepared heteroatom-containing nano-carbon material were listed in Table 2. FIG. 3 was the transmission electron microscope photo of the prepared heteroatom-containing nano-carbon material. It could be seen from FIG. 3 that the heteroatom-containing nano-carbon material had a good microstructure, indicating that the reaction process had little effect on the structure of the nano-carbon material.

Comparative Preparation Example 3

The same aqueous dispersion as that in Preparation Example 7 was placed in a three-neck flask equipped with a condenser pipe. The three-neck flask was placed in an oil bath of 140° C. The reaction was conducted at normal pressure under reflux for 48 hours. After the completion of reaction, the contents in the three-neck flask were cooled to room temperature, the reaction mixture was filtered and washed, and the solid substance was collected. The collected solid substance was dried under the normal pressure at 120° C. for 6 hours to produce the heteroatom-containing nano-carbon material. The composition and the properties of the prepared heteroatom-containing nano-carbon material were listed in Table 2.

Comparative Preparation Example 4

The heteroatom-containing nano-carbon material was prepared by using the same process as that of Preparation Example 7 except that in Step (1), tetrapropyl ammonium hydroxide was replaced with the same mole amount of HCl. The composition and the properties of the prepared heteroatom-containing nano-carbon material were listed in Table 2.

Comparative Preparation Example 5

The heteroatom-containing nano-carbon material was prepared by using the same process as that of Preparation Example 7 except that in Step (1), tetrapropyl ammonium hydroxide was replaced with the same mole amount of NH$_4$Cl. The composition and the properties of the prepared heteroatom-containing nano-carbon material were listed in Table 2.

Comparative Preparation Example 6

The heteroatom-containing nano-carbon material was prepared by using the same process as that of Preparation Example 7 except that in Step (1), tetrapropyl ammonium hydroxide was replaced with the same mole amount of tetrapropylammonium chloride. The composition and the properties of the prepared heteroatom-containing nano-carbon material were listed in Table 2.

Preparation Example 8

The heteroatom-containing nano-carbon material was prepared by using the same process as that of Preparation Example 7 except that in Step (1), tetrapropyl ammonium hydroxide was replaced with the same mole amount of n-propylamine. The composition and the properties of the prepared heteroatom-containing nano-carbon material were listed in Table 2.

Preparation Example 9

The heteroatom-containing nano-carbon material was prepared by using the same process as that of Preparation Example 7 except that in Step (1), tetrapropyl ammonium hydroxide was replaced with the same mole amount of pyridine. The composition and the properties of the prepared heteroatom-containing nano-carbon material were listed in Table 2.

Preparation Example 10

The heteroatom-containing nano-carbon material was prepared by using the same process as that of Preparation Example 7 except that in Step (1), tetrapropyl ammonium hydroxide was replaced with the same mole amount of cyclohexylamine. The composition and the properties of the prepared heteroatom-containing nano-carbon material were listed in Table 2.

Preparation Example 11

The heteroatom-containing nano-carbon material was prepared by using the same process as that of Preparation Example 7 except that in Step (1), tetrapropyl ammonium hydroxide was replaced with ethylene diamine, wherein the mole amount of ethylene diamine was a half of the mole amount of the tetrapropyl ammonium hydroxide. The composition and the properties of the prepared heteroatom-containing nano-carbon material were listed in Table 2.

Preparation Example 12

The heteroatom-containing nano-carbon material was prepared by using the same process as that of Preparation Example 7 except that in Step (1), tetrapropyl ammonium hydroxide was replaced with the same mole amount of diethanolamine. The composition and the properties of the prepared heteroatom-containing nano-carbon material were listed in Table 2.

Preparation Example 13

The heteroatom-containing nano-carbon material was prepared by using the same process as that of Preparation Example 7 except that in Step (1), tetrapropyl ammonium hydroxide was replaced with hexamethylenetetramine, and the mole amount of hexamethylenetetramine was 0.25-fold of the mole amount of tetrapropyl ammonium hydroxide. The composition and the properties of the prepared heteroatom-containing nano-carbon material were listed in Table 2.

Preparation Example 14

The heteroatom-containing nano-carbon material was prepared by using the same process as that of Preparation Example 7 except that in Step (1), tetrapropyl ammonium hydroxide was replaced with dietheylene triamine, and the mole amount of dietheylene triamine was 0.3-fold of the mole amount of tetrapropyl ammonium hydroxide. The composition and the properties of the prepared heteroatom-containing nano-carbon material were listed in Table 2.

Preparation Example 15

The heteroatom-containing nano-carbon material was prepared by using the same process as that of Preparation Example 7 except that in Step (1), the starting nano-carbon material was identical to the starting nano-carbon material of Preparation Example 2. The composition and the properties of the prepared heteroatom-containing nano-carbon material were listed in Table 2.

Preparation Example 16

The heteroatom-containing nano-carbon material was prepared by using the same process as that of Preparation Example 7 except that, in Step (2), the obtained aqueous dispersion was placed in a high-pressure reaction vessel having an inner lining of polytetrafluoroethylene, and reacted at 80° C. under an autogenous pressure for 48 hours. The composition and the properties of the prepared heteroatom-containing nano-carbon material were listed in Table 2.

Preparation Example 17

The heteroatom-containing nano-carbon material was prepared by using the same process as that of Preparation Example 7 except that in Step (1), the weight ratio of the starting nano-carbon material to tetrapropyl ammonium hydroxide was 1:0.4. The composition and the properties of the prepared heteroatom-containing nano-carbon material were listed in Table 2.

Preparation Example 18

The heteroatom-containing nano-carbon material was prepared by using the same process as that of Preparation Example 4 except that in Step (1), the starting nano-carbon material was dispersed in deionized water, and then added tetraethylammonium hydroxide (as a 20 wt % aqueous dispersion) to obtain an aqueous dispersion, wherein the weight ratio of the starting nano-carbon material to tetraethylammonium hydroxide was 1:5. The composition and the properties of the prepared heteroatom-containing nano-carbon material were listed in Table 2.

Comparative Preparation Example 7

The same aqueous dispersion as that in Preparation Example 18 was placed in a three-neck flask equipped with a condenser pipe. The three-neck flask was placed in an oil bath of 180° C. The reaction was conducted at normal pressure under reflux for 24 hours. After the completion of reaction, the contents in the three-neck flask were cooled to room temperature, the reaction mixture was filtered and washed, and the solid substance was collected. The collected solid substance was dried under the normal pressure at 120° C. for 6 hours to produce the heteroatom-containing nano-carbon material. The composition and the properties of the prepared heteroatom-containing nano-carbon material were listed in Table 2.

Preparation Example 19

The heteroatom-containing nano-carbon material was prepared by using the same process as that of Preparation Example 18 except that in Step (1), the starting nano-carbon material was identical to the starting nano-carbon material in Preparation Example 5. The composition and the properties of the prepared heteroatom-containing nano-carbon material were listed in Table 2.

Preparation Example 20

The heteroatom-containing nano-carbon material was prepared by using the same process as that of Preparation Example 18 except that, in Step (2), the obtained aqueous dispersion was placed in a high-pressure reaction vessel having an inner lining of polytetrafluoroethylene, and reacted under an autogenous pressure at 200° C. for 48 hours. The composition and the properties of the prepared heteroatom-containing nano-carbon material were listed in Table 2.

Preparation Example 21

The heteroatom-containing nano-carbon material was prepared by using the same process as that of Preparation Example 18 except that in Step (1), the weight ratio of the starting nano-carbon material to tetraethylammonium hydroxide was 1:8. The composition and the properties of the prepared heteroatom-containing nano-carbon material were listed in Table 2.

Preparation Example 22

(1) 20 g of the multi-walled carbon nanotube (identical to the starting nano-carbon material of Preparation Example 1), used as the starting nano-carbon material, was dispersed in 200 g deionized water, wherein the dispersing was conducted in an ultrasonic oscillation condition, the ultrasonic oscillation condition included 40 kHz (frequency) and 0.5 hour (time). Then diethanolamine as the organic base was added to obtain an aqueous dispersion, wherein the weight ratio of the starting nano-carbon material to the organic base was 1:1.

(2) The obtained aqueous dispersion was placed in a high-pressure reaction vessel having an inner lining of polytetrafluoroethylene, and reacted under an autogenous pressure at 120° C. for 24 hours. After the completion of reaction, the temperature of the high pressure reaction vessel dropped to room temperature, the reaction vessel was opened, the reaction mixture was filtered and washed, and the solid substance was collected. The collected solid substance was dried under the normal pressure at 120° C. for 12 hours to produce the heteroatom-containing nano-carbon material. The composition and the properties of said heteroatom-containing nano-carbon material were listed in Table 3.

Comparative Preparation Example 8

The same aqueous dispersion as that in Preparation Example 22 was placed in a three-neck flask equipped with a condenser pipe. The three-neck flask was placed in an oil bath of 120° C. The reaction was conducted at normal pressure under reflux for 24 hours. After the completion of reaction, the contents in the three-neck flask were cooled to room temperature, the reaction mixture was filtered and washed, and the solid substance was collected. The collected solid substance was dried under the normal pressure at 120° C. for 6 hours to produce the heteroatom-containing nano-carbon material. The composition and the properties of the prepared heteroatom-containing nano-carbon material were listed in Table 3.

Preparation Example 23

(1) 20 g of the multi-walled carbon nanotube (identical to the starting nano-carbon material of Preparation Example 4), used as the starting nano-carbon material, was dispersed in 500 g deionized water, wherein the dispersing was conducted in an ultrasonic oscillation condition, the ultrasonic oscillation condition included 40 kHz (frequency) and 0.5 hour (time). Then triethanolamine as the organic base was added to obtain an aqueous dispersion, wherein the weight ratio of the starting nano-carbon material to the organic base was 1:5.

(2) The obtained aqueous dispersion was placed in a high-pressure reaction vessel having an inner lining of polytetrafluoroethylene, and reacted under an autogenous pressure at 150° C. for 36 hours. After the completion of reaction, the temperature of the high pressure reaction vessel dropped to room temperature, the reaction vessel was opened, the reaction mixture was filtered and washed, and the solid substance was collected. The collected solid substance was dried under the normal pressure at 140° C. for 8 hours to produce the heteroatom-containing nano-carbon material. The composition and the properties of said heteroatom-containing nano-carbon material were listed in Table 3.

Preparation Example 24

The heteroatom-containing nano-carbon material was prepared by using the same process as that of Preparation Example 22 except that in Step (2), the obtained aqueous dispersion was placed in a high-pressure reaction vessel having an inner lining of polytetrafluoroethylene, and reacted at 90° C. under an autogenous pressure for 24 hours. The composition and the properties of the prepared heteroatom-containing nano-carbon material were listed in Table 3.

Preparation Example 25

The heteroatom-containing nano-carbon material was prepared by using the same process as that of Preparation Example 22 except that in Step (1), the multi-walled carbon nanotube as the starting nano-carbon material was identical to the starting nano-carbon material of Preparation Example 2. The composition and the properties of the prepared heteroatom-containing nano-carbon material were listed in Table 3.

Preparation Example 26

The heteroatom-containing nano-carbon material was prepared by using the same process as that of Preparation Example 22 except that in Step (1), the weight ratio of the starting nano-carbon material to the organic base was 1:0.2. The composition and the properties of the prepared heteroatom-containing nano-carbon material were listed in Table 3.

Preparation Example 27

The heteroatom-containing nano-carbon material was prepared by using the same process as that of Preparation Example 22 except that in Step (1), diethanolamine was replaced with the same mole amount of n-butylamine. The composition and the properties of the prepared heteroatom-containing nano-carbon material were listed in Table 3.

Preparation Example 28

The heteroatom-containing nano-carbon material was prepared by using the same process as that of Preparation Example 23 except that in Step (1), triethanolamine was replaced with the same mole amount of aniline. The composition and the properties of the prepared heteroatom-containing nano-carbon material were listed in Table 3.

Preparation Example 29

(1) 20 g of the multi-walled carbon nanotube (identical to the starting nano-carbon material of Preparation Example 1), used as the starting nano-carbon material, was dispersed in 250 g deionized water, wherein the dispersing was conducted in an ultrasonic oscillation condition, the ultrasonic oscillation condition included 40 kHz (frequency) and 0.5 hour (time). Then ethylene diamine as the organic base was added to obtain an aqueous dispersion, wherein the weight ratio of the starting nano-carbon material to the organic base was 1:1.25.

(2) The obtained aqueous dispersion was placed in a high-pressure reaction vessel having an inner lining of polytetrafluoroethylene, and reacted under an autogenous pressure at 150° C. for 48 hours. After the completion of reaction, the temperature of the high pressure reaction vessel dropped to room temperature, the reaction vessel was opened, the reaction mixture was filtered and washed, and the solid substance was collected. The collected solid substance was dried under the normal pressure at 150° C. for 5 hours to produce the heteroatom-containing nano-carbon material. The composition and the properties of said heteroatom-containing nano-carbon material were listed in Table 3.

Comparative Preparation Example 9

The same aqueous dispersion as that in Preparation Example 29 was placed in a three-neck flask equipped with a condenser pipe. The three-neck flask was placed in an oil bath of 150° C. The reaction was conducted at normal pressure under reflux for 48 hours. After the completion of reaction, the contents in the three-neck flask were cooled to room temperature, the reaction mixture was filtered and washed, and the solid substance was collected. The collected solid substance was dried under the normal pressure at 120° C. for 6 hours to produce the heteroatom-containing nano-carbon material. The composition and the properties of the prepared heteroatom-containing nano-carbon material were listed in Table 3.

Preparation Example 30

(1) 20 g of the multi-walled carbon nanotube (identical to the starting nano-carbon material of Preparation Example 4), used as the starting nano-carbon material, was dispersed in 800 g deionized water, wherein the dispersing was conducted in an ultrasonic oscillation condition. The ultrasonic oscillation condition included 60 kHz (frequency) and 1.5 hours (time). Then hexylene diamine as the organic base was added to obtain an aqueous dispersion, wherein the weight ratio of the starting nano-carbon material to hexylene diamine was 1:4.

(2) The obtained aqueous dispersion was placed in a high-pressure reaction vessel having an inner lining of polytetrafluoroethylene, and reacted under an autogenous pressure at 120° C. for 24 hours. After the completion of reaction, the temperature of the high pressure reaction vessel dropped to room temperature, the reaction vessel was opened, the reaction mixture was filtered and washed, and the solid substance was collected. The collected solid substance was dried under the normal pressure at 120° C. for 12 hours to produce the heteroatom-containing nano-carbon material. The composition and the properties of said heteroatom-containing nano-carbon material were listed in Table 3.

Preparation Example 31

The heteroatom-containing nano-carbon material was prepared by using the same process as that of Preparation Example 29 except that in Step (1), the multi-walled carbon nanotube as the starting nano-carbon material was identical to that of Preparation Example 2. The composition and the properties of the prepared heteroatom-containing nano-carbon material were listed in Table 3.

Preparation Example 32

The heteroatom-containing nano-carbon material was prepared by using the same process as that of Preparation Example 29 except that, in Step (2), the obtained aqueous dispersion was placed in a high-pressure reaction vessel having an inner lining of polytetrafluoroethylene, and reacted under an autogenous pressure at 200° C. for 24 hours. The composition and the properties of the prepared heteroatom-containing nano-carbon material were listed in Table 3.

Preparation Example 33

The heteroatom-containing nano-carbon material was prepared by using the same process as that of Preparation Example 29 except that in Step (1), the weight ratio of the starting nano-carbon material to the organic base was 1:0.25. The composition and the properties of the prepared heteroatom-containing nano-carbon material were listed in Table 3.

Preparation Example 34

The heteroatom-containing nano-carbon material was prepared by using the same process as that of Preparation Example 29 except that in Step (1), ethylene diamine was replaced with ethylamine, the mole amount of ethylamine was twice the mole amount of ethylene diamine. The composition and the properties of the prepared heteroatom-containing nano-carbon material were listed in Table 3.

Preparation Example 35

The heteroatom-containing nano-carbon material was prepared by using the same process as that of Preparation Example 30 except that in Step (1), hexylene diamine was replaced with triethanolamine, the mole amount of triethanolamine was twice the mole amount of hexylene diamine. The composition and the properties of the prepared heteroatom-containing nano-carbon material were listed in Table 3.

Preparation Example 36

The heteroatom-containing nano-carbon material obtained in Preparation Example 1 was calcined at 350° C. in an air atmosphere for 4 hours. The composition and the properties of the prepared heteroatom-containing nano-carbon material were listed in Table 4.

Comparative Preparation Example 10

The heteroatom-containing nano-carbon material obtained in Comparative Preparation Example 1 was calcined at 350° C. in an air atmosphere for 4 hours. The composition and the properties of the prepared heteroatom-containing nano-carbon material were listed in Table 4.

Preparation Example 37

The heteroatom-containing nano-carbon material obtained in Preparation Example 7 was calcined at 350° C. in an air atmosphere for 4 hours. The composition and the properties of the prepared heteroatom-containing nano-carbon material were listed in Table 4.

Comparative Preparation Example 11

The heteroatom-containing nano-carbon material obtained in Comparative Preparation Example 3 was calcined at 350° C. in an air atmosphere for 4 hours. The composition and the properties of the prepared heteroatom-containing nano-carbon material were listed in Table 4.

Comparative Preparation Example 12

The heteroatom-containing nano-carbon material obtained in Comparative Preparation Example 4 was calcined at 350° C. in an air atmosphere for 4 hours. The composition and the properties of the prepared heteroatom-containing nano-carbon material were listed in Table 4.

Comparative Preparation Example 13

The heteroatom-containing nano-carbon material obtained in Comparative Preparation Example 5 was calcined at 350° C. in an air atmosphere for 4 hours. The composition and the properties of the prepared heteroatom-containing nano-carbon material were listed in Table 4.

Comparative Preparation Example 14

The heteroatom-containing nano-carbon material obtained in Comparative Preparation Example 6 was calcined at 350° C. in an air atmosphere for 4 hours. The composition and the properties of the prepared heteroatom-containing nano-carbon material were listed in Table 4.

Preparation Example 38

The heteroatom-containing nano-carbon material obtained in Preparation Example 18 was calcined at 450° C. in an air atmosphere for 2 hours. The composition and the properties of the prepared heteroatom-containing nano-carbon material were listed in Table 4.

Preparation Example 39

The heteroatom-containing nano-carbon material obtained in Preparation Example 19 was calcined at 450° C. in an air atmosphere for 2 hours. The composition and the properties of the prepared heteroatom-containing nano-carbon material were listed in Table 4.

Preparation Example 40

The heteroatom-containing nano-carbon material obtained in Preparation Example 22 was calcined at 400° C. in an air atmosphere for 4 hours. The composition and the properties of the prepared heteroatom-containing nano-carbon material were listed in Table 4.

Comparative Preparation Example 15

The heteroatom-containing nano-carbon material obtained in Comparative Preparation Example 8 was calcined at 400° C. in an air atmosphere for 4 hours. The composition and the properties of the prepared heteroatom-containing nano-carbon material were listed in Table 4.

Preparation Example 41

The heteroatom-containing nano-carbon material obtained in Preparation Example 23 was calcined at 380° C. in an air atmosphere for 6 hours. The composition and the properties of the prepared heteroatom-containing nano-carbon material were listed in Table 4.

Preparation Example 42

The heteroatom-containing nano-carbon material obtained in Preparation Example 26 was calcined at 400° C. in an air atmosphere for 5 hours. The composition and the properties of the prepared heteroatom-containing nano-carbon material were listed in Table 4.

Preparation Example 43

The heteroatom-containing nano-carbon material obtained in Preparation Example 28 was calcined at 380° C. in an air atmosphere for 6 hours. The composition and the properties of the prepared heteroatom-containing nano-carbon material were listed in Table 4.

Preparation Example 44

The heteroatom-containing nano-carbon material obtained in Preparation Example 29 was calcined at 410° C. in an air atmosphere for 5 hours. The composition and the properties of the prepared heteroatom-containing nano-carbon material were listed in Table 4.

Comparative Preparation Example 16

The heteroatom-containing nano-carbon material obtained in Comparative Preparation Example 9 was calcined at 410° C. in an air atmosphere for 5 hours. The composition and the properties of the prepared heteroatom-containing nano-carbon material were listed in Table 4.

Preparation Example 45

The heteroatom-containing nano-carbon material obtained in Preparation Example 30 was calcined at 370° C. in an air atmosphere for 8 hours. The composition and the properties of the prepared heteroatom-containing nano-carbon material were listed in Table 4.

Preparation Example 46

The heteroatom-containing nano-carbon material obtained in Preparation Example 33 was calcined at 410° C. in an air atmosphere for 5 hours. The composition and the properties of the prepared heteroatom-containing nano-carbon material were listed in Table 4.

Preparation Example 47

The heteroatom-containing nano-carbon material obtained in Preparation Example 35 was calcined at 370° C. in an air atmosphere for 8 hours. The composition and the properties of the prepared heteroatom-containing nano-carbon material were listed in Table 4.

TABLE 1

| No. | Composition | | | | | | | | | Specific surface area ($m^2/g$) | $w_{500}/w_{800}$ |
|---|---|---|---|---|---|---|---|---|---|---|---|
| | N (wt %) | O (wt %) | C (wt %) | $I_O^c/I_O^e$ | $I_N^c/I_N^t$ | $I_N^g/I_N^t$ | $I_C^c/I_C^e$ | $C^1$ (wt %) | $C^2$ (wt %) | | |
| Preparation Example 1 | /[3] | 5.3 | 94.7 | 0.61 | / | / | 0.56 | 82 | 18 | 132 | 0.13 |
| Comparative Preparation | / | 1.4 | 98.6 | 0.16 | / | / | 0.18 | 86 | 14 | 134 | 0.27 |

TABLE 1-continued

| No. | Composition | | | | | | | | | Specific surface area | |
|---|---|---|---|---|---|---|---|---|---|---|---|
| | N (wt %) | O (wt %) | C (wt %) | $I_O^c/I_O^e$ | $I_N^c/I_N^t$ | $I_N^g/I_N^t$ | $I_C^c/I_C^e$ | $C^1$ (wt %) | $C^2$ (wt %) | (m²/g) | $w_{500}/w_{800}$ |
| Example 1 Preparation Example 2 | / | 4.7 | 95.3 | 0.56 | / | / | 0.44 | 80 | 20 | 246 | 0.41 |
| Preparation Example 3 | / | 3.2 | 96.8 | 0.44 | / | / | 0.36 | 85 | 15 | 123 | 0.19 |
| Preparation Example 4 | / | 4.6 | 95.4 | 0.59 | / | / | 0.70 | 84 | 16 | 175 | 0.13 |
| Comparative Preparation Example 2 | / | 0.7 | 99.3 | 0.12 | / | / | 0.15 | 89 | 11 | 179 | 0.34 |
| Preparation Example 5 | / | 5.5 | 94.5 | 0.51 | / | / | 0.48 | 73 | 27 | 102 | 0.37 |
| Preparation Example 6 | / | 4.2 | 95.8 | 0.42 | / | / | 0.56 | 81 | 19 | 174 | 0.15 |

[1] Based on the total amount of the carbon element determined with the X-ray photoelectron spectroscopy, the content of the carbon element determined with the peak(s) in the range of 284.7-284.9 eV in the X-ray photoelectron spectroscopy;
[2] Based on the total amount of the carbon element determined with the X-ray photoelectron spectroscopy, the content of the carbon element determined with the peak(s) in the range of 286.0-288.8 eV in the X-ray photoelectron spectroscopy;
[3] Not detected.

TABLE 2

| No. | Composition | | | | | | | | | Specific surface area | |
|---|---|---|---|---|---|---|---|---|---|---|---|
| | N (wt %) | O (wt %) | C (wt %) | $I_N^c/I_N^t$ | $I_N^g/I_N^t$ | $I_O^c/I_O^e$ | $I_C^c/I_C^e$ | $C^1$ (wt %) | $C^2$ (wt %) | (m²/g) | $w_{500}/w_{800}$ |
| Preparation Example 7 | 1.1 | 5.4 | 93.5 | 0.82 | 0.18 | 0.76 | 0.59 | 79 | 21 | 139 | 0.11 |
| Comparative Preparation Example 3 | 0.3 | 1.3 | 98.4 | 0.68 | 0.32 | 0.23 | 0.12 | 88 | 12 | 121 | 0.26 |
| Comparative Preparation Example 4 | /[3] | 4.1 | 95.9 | / | / | 0.16 | 0.33 | 85 | 15 | 134 | 0.18 |
| Comparative Preparation Example 5 | 0.8 | 3.1 | 96.1 | 0.63 | 0.37 | 1.04 | 1.27 | 86 | 14 | 131 | 0.23 |
| Comparative Preparation Example 6 | 0.5 | 4.8 | 94.7 | 0.54 | 0.46 | 0.15 | 0.32 | 84 | 16 | 126 | 0.31 |
| Preparation Example 8 | 1.6 | 4.1 | 94.3 | 0.89 | 0.11 | 0.67 | 0.77 | 84 | 16 | 118 | 0.15 |
| Preparation Example 9 | 1.2 | 5.6 | 93.2 | 0.94 | 0.06 | 0.53 | 0.47 | 74 | 26 | 133 | 0.19 |
| Preparation Example 10 | 1.5 | 2.4 | 96.1 | 0.76 | 0.24 | 0.49 | 0.32 | 86 | 14 | 130 | 0.14 |
| Preparation Example 11 | 1.1 | 3.5 | 95.4 | 0.78 | 0.22 | 0.56 | 0.73 | 84 | 16 | 142 | 0.18 |
| Preparation Example 12 | 1.8 | 3.0 | 95.2 | 0.81 | 0.19 | 0.37 | 0.48 | 87 | 13 | 136 | 0.15 |
| Preparation Example 13 | 0.9 | 5.4 | 93.7 | 0.86 | 0.14 | 0.46 | 0.51 | 75 | 25 | 119 | 0.16 |
| Preparation Example 14 | 1.0 | 5.2 | 93.8 | 0.95 | 0.05 | 0.67 | 0.59 | 78 | 22 | 151 | 0.09 |
| Preparation Example 15 | 1.3 | 3.2 | 95.5 | 0.87 | 0.13 | 0.71 | 0.61 | 79 | 21 | 238 | 0.35 |
| Preparation Example 16 | 0.2 | 3.1 | 96.7 | 0.71 | 0.29 | 0.42 | 0.44 | 87 | 13 | 134 | 0.08 |
| Preparation Example 17 | 0.6 | 5.8 | 93.6 | 0.86 | 0.14 | 0.59 | 0.51 | 78 | 22 | 138 | 0.15 |
| Preparation Example 18 | 1.4 | 4.7 | 93.9 | 0.94 | 0.06 | 0.56 | 0.46 | 83 | 17 | 179 | 0.13 |
| Comparative Preparation Example 7 | 0.8 | 3.3 | 95.9 | 0.85 | 0.15 | 0.18 | 0.13 | 86 | 14 | 186 | 0.26 |
| Preparation Example 19 | 1.2 | 4.4 | 94.4 | 0.96 | 0.04 | 0.37 | 0.42 | 85 | 15 | 106 | 0.28 |

TABLE 2-continued

| No. | Composition | | | | | | | | | Specific surface area | |
|---|---|---|---|---|---|---|---|---|---|---|---|
| | N (wt %) | O (wt %) | C (wt %) | $I_N^c/I_N^t$ | $I_N^g/I_N^t$ | $I_O^c/I_O^e$ | $I_C^c/I_C^e$ | $C^1$ (wt %) | $C^2$ (wt %) | (m²/g) | $w_{500}/w_{800}$ |
| Preparation Example 20 | 1.6 | 5.3 | 93.1 | 0.72 | 0.28 | 0.72 | 0.79 | 72 | 28 | 174 | 0.13 |
| Preparation Example 21 | 1.3 | 4.7 | 94.0 | 0.83 | 0.17 | 0.77 | 0.87 | 75 | 25 | 165 | 0.11 |

[1] Based on the total amount of the carbon element determined with the X-ray photoelectron spectroscopy the content of the carbon element determined with the peak(s) in the range of 284.7-284.9 eV in the X-ray photoelectron spectroscopy;
[2] Based on the total amount of the carbon element determined with the X-ray photoelectron spectroscopy, the content of the carbon element determined with the peak(s) in the range of 286.0-288.8 eV in the X-ray photoelectron spectroscopy;
[3] Not detected.

TABLE 3

| No. | Composition | | | | | | | | | Specific surface area | |
|---|---|---|---|---|---|---|---|---|---|---|---|
| | N (wt %) | O (wt %) | C (wt %) | $I_O^c/I_O^e$ | $I_N^c/I_N^t$ | $I_N^g/I_N^t$ | $I_C^c/I_C^e$ | $C^1$ (wt %) | $C^2$ (wt %) | (m²/g) | $w_{500}/w_{800}$ |
| Preparation Example 22 | 0.8 | 3.6 | 95.6 | 0.75 | 0.89 | 0.11 | 0.57 | 76 | 24 | 138 | 0.13 |
| Comparative Preparation Example 8 | 0.6 | 1.7 | 97.7 | 0.27 | 0.73 | 0.27 | 0.18 | 89 | 11 | 135 | 0.25 |
| Preparation Example 23 | 1.2 | 4.6 | 94.2 | 0.45 | 0.88 | 0.12 | 0.48 | 74 | 26 | 175 | 0.15 |
| Preparation Example 24 | 0.5 | 2.7 | 96.8 | 0.35 | 0.79 | 0.21 | 0.65 | 85 | 15 | 129 | 0.19 |
| Preparation Example 25 | 1.7 | 5.2 | 93.1 | 0.37 | 0.82 | 0.18 | 0.71 | 72 | 28 | 226 | 0.34 |
| Preparation Example 26 | 0.4 | 5.3 | 94.3 | 0.51 | 0.81 | 0.19 | 0.73 | 75 | 25 | 137 | 0.18 |
| Preparation Example 27 | 0.9 | 3.1 | 96.0 | 0.69 | 0.74 | 0.26 | 0.68 | 84 | 16 | 131 | 0.15 |
| Preparation Example 28 | 1.2 | 5.4 | 93.4 | 0.41 | 0.89 | 0.11 | 0.51 | 76 | 24 | 179 | 0.26 |
| Preparation Example 29 | 1.8 | 4.6 | 93.6 | 0.63 | 0.83 | 0.17 | 0.89 | 74 | 26 | 135 | 0.09 |
| Comparative Preparation Example 9 | 0.5 | 3.7 | 95.8 | 0.28 | 0.45 | 0.55 | 0.17 | 84 | 16 | 113 | 0.23 |
| Preparation Example 30 | 1.8 | 5.1 | 93.1 | 0.67 | 0.81 | 0.19 | 0.94 | 77 | 23 | 189 | 0.08 |
| Preparation Example 31 | 1.5 | 5.7 | 92.8 | 0.44 | 0.82 | 0.18 | 0.74 | 75 | 25 | 294 | 0.35 |
| Preparation Example 32 | 1.9 | 5.3 | 92.8 | 0.52 | 0.78 | 0.22 | 0.63 | 78 | 22 | 127 | 0.23 |
| Preparation Example 33 | 0.6 | 4.8 | 94.6 | 0.56 | 0.73 | 0.27 | 0.88 | 80 | 20 | 110 | 0.16 |
| Preparation Example 34 | 1.3 | 4.4 | 94.3 | 0.45 | 0.79 | 0.21 | 0.42 | 77 | 23 | 111 | 0.15 |
| Preparation Example 35 | 0.7 | 5.3 | 94.0 | 0.47 | 0.75 | 0.25 | 0.49 | 73 | 27 | 179 | 0.16 |

[1] Based on the total amount of the carbon element determined with the X-ray photoelectron spectroscopy the content of the carbon element determined with the peak(s) in the range of 284.7-284.9 eV in the X-ray photoelectron spectroscopy;
[2] Based on the total amount of the carbon element determined with the X-ray photoelectron spectroscopy, the content of the carbon element determined with the peak(s) in the range of 286.0-288.8 eV in the X-ray photoelectron spectroscopy.

TABLE 4

| No. | Composition | | | | | | | | | Specific surface area | |
|---|---|---|---|---|---|---|---|---|---|---|---|
| | N (wt %) | O (wt %) | C (wt %) | $I_O^c/I_O^e$ | $I_N^c/I_N^t$ | $I_N^g/I_N^t$ | $I_C^c/I_C^e$ | $C^1$ (wt %) | $C^2$ (wt %) | (m²/g) | $w_{500}/w_{800}$ |
| Preparation Example 36 | /[3] | 5.1 | 94.9 | 0.63 | / | / | 0.64 | 82 | 18 | 131 | 0.10 |
| Comparative Preparation Example 10 | / | 1.3 | 98.7 | 0.17 | / | / | 0.22 | 85 | 15 | 121 | 0.21 |

TABLE 4-continued

| No. | Composition | | | | | | | | | Specific surface area | |
|---|---|---|---|---|---|---|---|---|---|---|---|
| | N (wt %) | O (wt %) | C (wt %) | $I_O^c/I_O^e$ | $I_N^c/I_N^t$ | $I_N^g/I_N^t$ | $I_C^c/I_C^e$ | $C^1$ (wt %) | $C^2$ (wt %) | (m$^2$/g) | $w_{500}/w_{800}$ |
| Preparation Example 37 | 1.5 | 4.5 | 94.0 | 0.76 | 0.89 | 0.11 | 0.60 | 83 | 17 | 141 | 0.09 |
| Comparative Preparation Example 11 | 0.9 | 1.9 | 97.2 | 0.28 | 0.88 | 0.12 | 0.15 | 86 | 14 | 113 | 0.18 |
| Comparative Preparation Example 12 | / | 4.7 | 95.3 | 0.17 | / | / | 0.39 | 85 | 15 | 115 | 0.14 |
| Comparative Preparation Example 13 | 1.4 | 4.5 | 94.1 | 1.26 | 0.79 | 0.21 | 1.22 | 84 | 16 | 117 | 0.20 |
| Comparative Preparation Example 14 | 0.7 | 4.0 | 95.3 | 0.16 | 0.76 | 0.24 | 0.38 | 86 | 14 | 113 | 0.23 |
| Preparation Example 38 | 1.1 | 4.5 | 94.4 | 0.75 | 0.85 | 0.15 | 0.56 | 85 | 15 | 176 | 0.09 |
| Preparation Example 39 | 2.0 | 5.3 | 92.7 | 0.51 | 0.79 | 0.21 | 0.58 | 76 | 24 | 114 | 0.23 |
| Preparation Example 40 | 1.2 | 4.5 | 94.3 | 0.46 | 0.85 | 0.15 | 0.49 | 84 | 16 | 136 | 0.11 |
| Comparative Preparation Example 15 | 0.4 | 2.3 | 97.3 | 0.23 | 0.77 | 0.23 | 0.14 | 88 | 12 | 112 | 0.21 |
| Preparation Example 41 | 1.3 | 4.8 | 93.9 | 0.48 | 0.86 | 0.14 | 0.51 | 74 | 26 | 170 | 0.10 |
| Preparation Example 42 | 1.2 | 6.0 | 92.8 | 0.41 | 0.93 | 0.07 | 0.64 | 75 | 25 | 127 | 0.15 |
| Preparation Example 43 | 1.6 | 5.5 | 92.9 | 0.44 | 0.72 | 0.28 | 0.61 | 81 | 19 | 174 | 0.19 |
| Preparation Example 44 | 1.8 | 5.4 | 92.8 | 0.66 | 0.82 | 0.18 | 0.85 | 80 | 20 | 131 | 0.08 |
| Comparative Preparation Example 16 | 0.7 | 5.1 | 94.2 | 0.18 | 0.86 | 0.14 | 0.16 | 83 | 17 | 124 | 0.14 |
| Preparation Example 45 | 1.5 | 5.5 | 93.0 | 0.60 | 0.85 | 0.15 | 0.85 | 79 | 21 | 179 | 0.04 |
| Preparation Example 46 | 1.1 | 4.6 | 94.3 | 0.67 | 0.75 | 0.25 | 0.78 | 84 | 16 | 117 | 0.07 |
| Preparation Example 47 | 0.9 | 5.8 | 93.3 | 0.54 | 0.87 | 0.13 | 0.62 | 78 | 22 | 173 | 0.12 |

[1] Based on the total amount of the carbon element determined with the X-ray photoelectron spectroscopy, the content of the carbon element determined with the peak(s) in the range of 284.7-284.9 eV in the X-ray photoelectron spectroscopy;
[2] Based on the total amount of the carbon element determined with the X-ray photoelectron spectroscopy, the content of the carbon element determined with the peak(s) in the range of 286.0-288.8 eV in the X-ray photoelectron spectroscopy;
[3] Not detected.

Examples 1-67 were provided for illustrating the processes of the present invention.

Examples 1-8

0.2 g (packing volume=1.5 mL) of heteroatom-containing nano-carbon materials, used as the catalyst, were respectively packed in a universal fixed-bed micro-quartz tube reactor. The micro-quartz tube reactor was blocked with quartz sand at both ends. A gaseous starting material containing hydrocarbons and oxygen was introduced to the reactor to conduct the reaction.

In the examples in which the heteroatom-containing nano-carbon material prepared in Preparation Examples 1-3, 7 and 36 were respectively used as catalyst: In the gaseous starting material, the concentration of n-butane was 1 vol %, the mole ratio of n-butane to oxygen was 0.5:1, and the balance was nitrogen as the carrier gas. The reaction was conducted under 0.1 MPa at 450° C. The total space velocity by volume of the gaseous starting material was 500 h$^{-1}$.

In the examples in which the heteroatom-containing nano-carbon material prepared in Preparation Examples 4-6 were respectively used as catalyst: In the gaseous starting material, the concentration of n-butane was 1.5 vol %, the mole ratio of n-butane to oxygen was 2:3, and the balance was nitrogen as the carrier gas. The reaction was conducted under 0 MPa at 420° C. The total space velocity by volume of the gaseous starting material was 100 h$^{-1}$.

The composition of the reaction mixture output from the reactor was continuously monitored, and the n-butane conversion, the total olefin selectivity and the 1-butylene selectivity were calculated. The results for after reacting for 3 hours and 24 hours were listed in Table 5.

Example 9 n-butane was oxidized in the same manner as Example 1 except that, the reaction was conducted under 0.5 MPa at 400° C. The experiment results were listed in Table 5.

Example 10 n-butane was oxidized in the same manner as Example 4 except that, the reaction was conducted under 0 MPa at 450° C. The experiment results were listed in Table 5.

Comparative Example 1 n-butane was oxidized in the same manner as Example 1 except that, the heteroatom-containing nano-carbon material prepared in Comparative Preparation Example 1 was used as the catalyst. The experiment results were listed in Table 5.

Comparative Example 2 n-butane was oxidized in the same manner as Example 4 except that, the heteroatom-containing nano-carbon material prepared in Comparative Preparation Example 2 was used as the catalyst. The experiment results were listed in Table 5.

Comparative Example 3 n-butane was oxidized in the same manner as Example 1 except that, the starting carbon material in Preparation Example 1 was used as the catalyst. The experiment results were listed in Table 5.

Comparative Example 4 n-butane was oxidized in the same manner as Example 4 except that, the starting carbon material in Preparation Example 4 was used as the catalyst. The experiment results were listed in Table 5.

Comparative Example 5 n-butane was oxidized in the same manner as Example 1 except that, the heteroatom-containing nano-carbon material prepared in Comparative Preparation Example 10 was used as the catalyst. The experiment results were listed in Table 5.

TABLE 5

| No. | Catalyst source | Reaction time (h) | n-butane conversion (wt %) | Total olefin selectivity (wt %) | 1-butylene selectivity (wt %) |
|---|---|---|---|---|---|
| Example 1 | Preparation Example 1 | 3 | 28.5 | 37.4 | 21.6 |
| | | 24 | 25.0 | 31.0 | 16.7 |
| Comparative Example 1 | Comparative Preparation Example 1 | 3 | 22.4 | 17.7 | 9.3 |
| | | 24 | 17.4 | 11.5 | 6.9 |
| Comparative Example 3 | Starting nano-carbon material | 3 | 15.6 | 18.7 | 9.6 |
| | | 24 | 14.2 | 17.0 | 8.8 |
| Example 2 | Preparation Example 2 | 3 | 25.7 | 33.7 | 20.8 |
| | | 24 | 20.1 | 24.4 | 14.7 |
| Example 3 | Preparation Example 3 | 3 | 25.0 | 32.1 | 18.7 |
| | | 24 | 20.0 | 24.9 | 14.3 |
| Example 4 | Preparation Example 4 | 3 | 26.1 | 40.1 | 25.7 |
| | | 24 | 22.4 | 35.5 | 19.4 |
| Comparative Example 2 | Comparative Preparation Example 2 | 3 | 19.6 | 23.1 | 13.1 |
| | | 24 | 13.9 | 17.6 | 7.1 |
| Comparative Example 4 | Starting nano-carbon material | 3 | 14.5 | 20.6 | 11.6 |
| | | 24 | 13.1 | 17.2 | 8.0 |
| Example 5 | Preparation Example 5 | 3 | 23.2 | 36.5 | 23.1 |
| | | 24 | 17.2 | 27.2 | 16.4 |
| Example 6 | Preparation Example 6 | 3 | 21.8 | 34.3 | 21.7 |
| | | 24 | 18.3 | 27.9 | 16.6 |
| Example 7 | Preparation Example 7 | 3 | 38.0 | 49.8 | 15.1 |
| | | 24 | 34.7 | 43.5 | 11.1 |
| Example 8 | Preparation Example 36 | 3 | 33.5 | 34.3 | 20.6 |
| | | 24 | 32.4 | 32.3 | 19.2 |
| Comparative Example 5 | Comparative Preparation Example 10 | 3 | 20.9 | 15.0 | 7.7 |
| | | 24 | 19.9 | 14.5 | 6.7 |
| Example 9 | Preparation Example 1 | 3 | 23.0 | 39.3 | 23.6 |
| | | 24 | 19.3 | 33.6 | 19.2 |

TABLE 5-continued

| No. | Catalyst source | Reaction time (h) | n-butane conversion (wt %) | Total olefin selectivity (wt %) | 1-butylene selectivity (wt %) |
|---|---|---|---|---|---|
| Example 10 | Preparation Example 4 | 3 | 31.6 | 34.0 | 20.1 |
|  |  | 24 | 27.4 | 25.6 | 14.7 |

Examples 11-30

0.2 g (packing volume=1.5 mL) of heteroatom-containing nano-carbon materials, used as the catalyst, were respectively packed in a universal fixed-bed micro-quartz tube reactor. The micro-quartz tube reactor was blocked with quartz sand at both ends. A gaseous starting material containing hydrocarbons and oxygen was introduced to the reactor to conduct the reaction.

In the examples in which the heteroatom-containing nano-carbon material prepared in Preparation Examples 1, 7-17, 36 and 37 were respectively used as catalyst: In the gaseous starting material, the concentration of n-butane was 2 vol %, the mole ratio of n-butane to oxygen was 1:3, and the balance was nitrogen as the carrier gas. The reaction was conducted under 0.1 MPa at 400° C. The total space velocity by volume of the gaseous starting material was 200 h$^{-1}$.

In the examples in which the heteroatom-containing nano-carbon material prepared in Preparation Examples 18-21, 38 and 39 were respectively used as catalyst: In the gaseous starting material, the concentration of n-butane was 1 vol %, the mole ratio of n-butane to oxygen was 1:1.5, and the balance was nitrogen as the carrier gas. The reaction was conducted under 0.5 MPa at 420° C. The total space velocity by volume of the gaseous starting material was 500 h$^{-1}$.

The composition of the reaction mixture output from the reactor was continuously monitored, and the n-butane conversion, the total olefin selectivity and the butadiene selectivity were calculated. The results for after reacting for 3 hours and 24 hours were listed in Table 6.

Comparative Examples 6-9 n-butane was oxidized in the same manner as Example 11 except that, the heteroatom-containing nano-carbon materials prepared in Comparative Preparation Examples 3-6 were respectively used as the catalysts. The experiment results were listed in Table 6.

Comparative Example 10 n-butane was oxidized in the same manner as Example 23 except that, the heteroatom-containing nano-carbon materials prepared in Comparative Preparation Example 7 was used as the catalyst. The experiment results were listed in Table 6.

Comparative Example 11 n-butane was oxidized in the same manner as Example 12 except that, the starting carbon material used in Preparation Example 7 was used as the catalyst. The experiment results were listed in Table 6.

Comparative Example 12 n-butane was oxidized in the same manner as Example 23 except that, the starting carbon material used in Preparation Example 18 was used as the catalyst. The experiment results were listed in Table 6.

Comparative Examples 13-16 n-butane was oxidized in the same manner as Example 28 except that, the heteroatom-containing nano-carbon materials prepared in Comparative Preparation Examples 11-14 were respectively used as the catalysts. The experiment results were listed in Table 6.

Examples 31-33 n-butane was oxidized in the same manner as Example 11 except that, the heteroatom-containing nano-carbon materials prepared in Preparation Examples 1, 7 and 8 were respectively used as the catalysts, and the reaction was conducted under 0.1 MPa at 450° C. The experiment results were listed in Table 6.

Examples 34-37 n-butane was oxidized in the same manner as Example 23 except that, the heteroatom-containing nano-carbon materials prepared in Preparation Examples 18-21 were respectively used as the catalysts, the reaction was conducted under 0.1 MPa at 400° C. The experiment results were listed in Table 6.

TABLE 6

| No. | Catalyst source | Reaction time (h) | n-butane conversion (wt %) | Total olefin selectivity (wt %) | Butadiene selectivity (wt %) |
|---|---|---|---|---|---|
| Example 11 | Preparation Example 1 | 3 | 28.3 | 42.9 | 8.3 |
|  |  | 24 | 24.3 | 35.9 | 4.8 |
| Example 12 | Preparation Example 7 | 3 | 41.8 | 52.5 | 30.0 |
|  |  | 24 | 37.1 | 45.2 | 26.2 |
| Comparative Example 6 | Comparative Preparation Example 3 | 3 | 26.4 | 21.9 | 10.3 |
|  |  | 24 | 15.3 | 15.8 | 7.9 |
| Comparative Example 7 | Comparative Preparation Example 4 | 3 | 24.0 | 20.5 | 9.4 |
|  |  | 24 | 13.3 | 10.2 | 5.8 |

TABLE 6-continued

| No. | Catalyst source | Reaction time (h) | n-butane conversion (wt %) | Total olefin selectivity (wt %) | Butadiene selectivity (wt %) |
|---|---|---|---|---|---|
| Comparative Example 8 | Comparative Preparation Example 5 | 3 | 22.4 | 19.1 | 9.1 |
| | | 24 | 14.0 | 11.4 | 7.6 |
| Comparative Example 9 | Comparative Preparation Example 6 | 3 | 20.1 | 20.4 | 12.6 |
| | | 24 | 14.4 | 16.5 | 9.0 |
| Comparative Example 11 | Starting nano-carbon material | 3 | 19.7 | 22.7 | 10.2 |
| | | 24 | 18.5 | 20.1 | 9.7 |
| Example 13 | Preparation Example 8 | 3 | 33.5 | 54.5 | 26.9 |
| | | 24 | 28.1 | 47.2 | 21.9 |
| Example 14 | Preparation Example 9 | 3 | 35.2 | 50.9 | 24.1 |
| | | 24 | 30.7 | 46.7 | 20.2 |
| Example 15 | Preparation Example 10 | 3 | 34.5 | 52.3 | 26.5 |
| | | 24 | 29.2 | 42.7 | 21.2 |
| Example 16 | Preparation Example 11 | 3 | 38.1 | 50.9 | 26.6 |
| | | 24 | 32.9 | 44.8 | 22.9 |
| Example 17 | Preparation Example 12 | 3 | 38.3 | 55.9 | 25.2 |
| | | 24 | 31.3 | 48.5 | 20.8 |
| Example 18 | Preparation Example 13 | 3 | 34.6 | 51.6 | 25.1 |
| | | 24 | 29.9 | 43.9 | 20.5 |
| Example 19 | Preparation Example 14 | 3 | 32.7 | 53.3 | 26.7 |
| | | 24 | 27.3 | 43.5 | 20.2 |
| Example 20 | Preparation Example 15 | 3 | 38.1 | 48.1 | 23.9 |
| | | 24 | 32.1 | 38.2 | 17.3 |
| Example 21 | Preparation Example 16 | 3 | 34.3 | 46.8 | 24.9 |
| | | 24 | 30.5 | 41.1 | 21.5 |
| Example 22 | Preparation Example 17 | 3 | 37.5 | 50.2 | 24.7 |
| | | 24 | 32.2 | 40.6 | 20.3 |
| Example 23 | Preparation Example 18 | 3 | 39.5 | 50.5 | 28.9 |
| | | 24 | 35.3 | 44.7 | 24.7 |
| Comparative Example 10 | Comparative Preparation Example 7 | 3 | 17.7 | 20.4 | 10.3 |
| | | 24 | 14.1 | 14.2 | 6.1 |
| Comparative Example 12 | Starting nano-carbon material | 3 | 21.2 | 18.2 | 9.7 |
| | | 24 | 19.5 | 16.2 | 7.0 |
| Example 24 | Preparation Example 19 | 3 | 35.0 | 48.7 | 25.1 |
| | | 24 | 28.1 | 40.1 | 19.4 |
| Example 25 | Preparation Example 20 | 3 | 35.5 | 46.9 | 26.2 |
| | | 24 | 30.2 | 41.5 | 21.5 |
| Example 26 | Preparation Example 21 | 3 | 35.8 | 43.6 | 26.2 |
| | | 24 | 30.6 | 38.9 | 20.3 |
| Example 27 | Preparation Example 36 | 3 | 26.9 | 43.1 | 12.8 |
| | | 24 | 25.6 | 40.9 | 11.5 |
| Example 28 | Preparation Example 37 | 3 | 43.3 | 50.2 | 29.4 |
| | | 24 | 41.1 | 48.7 | 27.7 |
| Comparative Example 13 | Comparative Preparation Example 11 | 3 | 25.8 | 25.4 | 10.4 |
| | | 24 | 21.8 | 24.3 | 9.3 |
| Comparative Example 14 | Comparative Preparation Example 12 | 3 | 20.5 | 24.7 | 10.5 |
| | | 24 | 18.6 | 23.3 | 8.7 |
| Comparative Example 15 | Comparative Preparation Example 13 | 3 | 23.0 | 18.3 | 9.8 |
| | | 24 | 19.4 | 17.1 | 7.8 |
| Comparative Example 16 | Comparative Preparation Example 14 | 3 | 19.8 | 19.7 | 10.2 |
| | | 24 | 18.0 | 17.5 | 8.9 |
| Example 29 | Preparation Example 38 | 3 | 40.4 | 47.1 | 22.2 |
| | | 24 | 38.9 | 45.2 | 21.8 |
| Example 30 | Preparation Example 39 | 3 | 33.2 | 44.2 | 20.6 |
| | | 24 | 30.6 | 42.2 | 18.1 |
| Example 31 | Preparation Example 1 | 3 | 33.7 | 36.9 | 6.2 |
| | | 24 | 29.9 | 33.1 | 3.9 |
| Example 32 | Preparation Example 7 | 3 | 44.3 | 49.6 | 27.7 |
| | | 24 | 40.4 | 42.6 | 23.6 |
| Example 33 | Preparation Example 8 | 3 | 35.2 | 50.6 | 24.3 |
| | | 24 | 32.6 | 44.4 | 20.6 |
| Example 34 | Preparation Example 18 | 3 | 37.5 | 55.5 | 30.5 |
| | | 24 | 32.7 | 49.1 | 26.8 |
| Example 35 | Preparation Example 19 | 3 | 34.1 | 53.5 | 28.5 |
| | | 24 | 29.4 | 45.5 | 23.7 |

TABLE 6-continued

| No. | Catalyst source | Reaction time (h) | n-butane conversion (wt %) | Total olefin selectivity (wt %) | Butadiene selectivity (wt %) |
|---|---|---|---|---|---|
| Example 36 | Preparation Example 20 | 3 | 32.7 | 48.6 | 25.9 |
|  |  | 24 | 28.2 | 41.9 | 22.5 |
| Example 37 | Preparation Example 21 | 3 | 33.9 | 47.1 | 25.7 |
|  |  | 24 | 29.5 | 40.5 | 22.1 |

Examples 38-48

0.2 g (packing volume=1.5 mL) of heteroatom-containing nano-carbon materials, used as the catalyst, were respectively packed in a universal fixed-bed micro-quartz tube reactor. The micro-quartz tube reactor was blocked with quartz sand at both ends. A gaseous starting material containing hydrocarbons and oxygen was introduced to the reactor to conduct the reaction.

In the examples in which the heteroatom-containing nano-carbon material prepared in Preparation Examples 22, 24-27, 40, 42 and 43 were respectively used as catalyst: In the gaseous starting material, the concentration of propane was 1 vol %, the mole ratio of propane to oxygen was 1:3, and the balance was nitrogen as the carrier gas. The reaction was conducted under 0.2 MPa at 480° C. The total space velocity by volume of the gaseous starting material was 150 $h^{-1}$.

In the examples in which the heteroatom-containing nano-carbon material prepared in Preparation Examples 23, 28 and 41 were respectively used as catalyst: In the gaseous starting material, the concentration of propane was 4 vol %, the mole ratio of propane to oxygen was 0.5:1, and the balance was nitrogen as the carrier gas. The reaction was conducted under 0.1 MPa at 420° C. The total space velocity by volume of the gaseous starting material was 20 $h^{-1}$.

The composition of the reaction mixture output from the reactor was continuously monitored, and the propane conversion and the $C_3$-alkene selectivity were calculated. The results for after reacting for 3 hours and 24 hours were listed in Table 7.

Comparative Example 17

Propane was oxidized in the same manner as Example 38 except that, the heteroatom-containing nano-carbon materials prepared in Comparative Preparation Example 8 was used as the catalyst. The experiment results were listed in Table 7.

Comparative Example 18

Propane was oxidized in the same manner as Example 38 except that, the starting carbon material used in Preparation Example 22 was used as the catalyst. The experiment results were listed in Table 7.

Comparative Example 19

Propane was oxidized in the same manner as Example 39 except that, the starting carbon material used in Preparation Example 23 was used as the catalyst. The experiment results were listed in Table 7.

Comparative Example 20

Propane was oxidized in the same manner as Example 45 except that, the heteroatom-containing nano-carbon materials prepared in Comparative Preparation Example 15 was used as the catalyst. The experiment results were listed in Table 7.

Examples 49-51

Propane was oxidized in the same manner as Example 38 except that, the heteroatom-containing nano-carbon materials prepared in Preparation Examples 22, 26 and 27 were respectively used as the catalyst, the reaction was conducted under 0 MPa at 440° C. The experiment results were listed in Table 7.

Example 52

Propane was oxidized in the same manner as Example 39 except that, the reaction was conducted under 1 MPa at 360° C. The experiment results were listed in Table 7.

TABLE 7

| No. | Catalyst source | Reaction time (h) | Propane conversion (wt %) | $C_3$-alkene selectivity (wt %) |
|---|---|---|---|---|
| Example 38 | Preparation Example 22 | 3 | 42.0 | 55.0 |
|  |  | 24 | 38.7 | 50.6 |
| Comparative Example 17 | Comparative Preparation Example 8 | 3 | 19.4 | 21.9 |
|  |  | 24 | 11.6 | 12.8 |
| Comparative Example 18 | Starting nano-carbon material | 3 | 16.7 | 19.2 |
|  |  | 24 | 15.0 | 17.6 |
| Example 39 | Preparation Example 23 | 3 | 38.1 | 59.8 |
|  |  | 24 | 35.8 | 55.6 |
| Comparative Example 19 | Starting nano-carbon material | 3 | 17.5 | 20.8 |
|  |  | 24 | 15.5 | 18.7 |
| Example 40 | Preparation Example 24 | 3 | 35.2 | 48.2 |
|  |  | 24 | 33.9 | 44.4 |
| Example 41 | Preparation Example 25 | 3 | 32.7 | 51.1 |
|  |  | 24 | 29.2 | 44.1 |
| Example 42 | Preparation Example 26 | 3 | 33.7 | 47.8 |
|  |  | 24 | 30.3 | 43.0 |
| Example 43 | Preparation Example 27 | 3 | 37.8 | 47.0 |
|  |  | 24 | 33.9 | 42.2 |
| Example 44 | Preparation Example 28 | 3 | 25.5 | 52.3 |
|  |  | 24 | 22.9 | 44.2 |
| Example 45 | Preparation Example 40 | 3 | 35.4 | 53.9 |
|  |  | 24 | 33.9 | 52.8 |
| Comparative Example 20 | Comparative Preparation Example 15 | 3 | 15.4 | 22.3 |
|  |  | 24 | 11.5 | 21.0 |
| Example 46 | Preparation Example 41 | 3 | 34.1 | 60.3 |
|  |  | 24 | 33.7 | 57.8 |
| Example 47 | Preparation Example 42 | 3 | 29.8 | 46.8 |
|  |  | 24 | 27.6 | 44.9 |
| Example 48 | Preparation Example 43 | 3 | 23.0 | 50.7 |
|  |  | 24 | 21.8 | 49.2 |
| Example 49 | Preparation Example 22 | 3 | 35.7 | 58.6 |
|  |  | 24 | 29.2 | 55.2 |
| Example 50 | Preparation Example 26 | 3 | 30.5 | 49.7 |
|  |  | 24 | 25.3 | 44.7 |

TABLE 7-continued

| No. | Catalyst source | Reaction time (h) | Propane conversion (wt %) | C$_3$-alkene selectivity (wt %) |
|---|---|---|---|---|
| Example 51 | Preparation Example 27 | 3 | 29.0 | 48.4 |
|  |  | 24 | 20.9 | 43.5 |
| Example 52 | Preparation Example 23 | 3 | 25.4 | 63.6 |
|  |  | 24 | 23.5 | 58.3 |

Examples 53-63

0.2 g (packing volume=1.5 mL) of heteroatom-containing nano-carbon materials, used as the catalyst, were respectively packed in a universal fixed-bed micro-quartz tube reactor. The micro-quartz tube reactor was blocked with quartz sand at both ends. A gaseous starting material containing phenylethane and oxygen was introduced to the reactor to conduct the reaction.

In the examples in which the heteroatom-containing nano-carbon material prepared in Preparation Examples 29, 31-34, 44 and 46 were respectively used as catalyst: In the gaseous starting material, the concentration of phenylethane was 2 vol %, the mole ratio of phenylethane to oxygen was 1:1, and the balance was nitrogen as the carrier gas. The reaction was conducted under 0.1 MPa at 400° C. The total space velocity by volume of the gaseous starting material was 250 h$^{-1}$.

In the examples in which the heteroatom-containing nano-carbon material prepared in Preparation Examples 30, 35, 45 and 47 were respectively used as catalyst: In the gaseous starting material, the concentration of phenylethane was 3 vol %, the mole ratio of phenylethane to oxygen was 2:1.5, and the balance was nitrogen as the carrier gas. The reaction was conducted under 0.5 MPa at 380° C. The total space velocity by volume of the gaseous starting material was 100 h$^{-1}$.

The composition of the reaction mixture output from the reactor was continuously monitored, and the phenylethane conversion and the phenylethene selectivity were calculated. The results for after reacting for 3 hours and 24 hours were listed in Table 8.

Comparative Example 21

Phenylethane was oxidized in the same manner as Example 53 except that, the heteroatom-containing nano-carbon materials prepared in Comparative Preparation Example 9 were used as the catalyst. The experiment results were listed in Table 8.

Comparative Example 22

Phenylethane was oxidized in the same manner as Example 53 except that, the starting nano-carbon material used in Preparation Example 29 was used as the catalyst. The experiment results were listed in Table 8.

Comparative Example 23

Phenylethane was oxidized in the same manner as Example 54 except that, the starting nano-carbon material used in Preparation Example 30 was used as the catalyst. The experiment results were listed in Table 8.

Comparative Example 24

Phenylethane was oxidized in the same manner as Example 60 except that, the heteroatom-containing nano-carbon material prepared in Comparative Preparation Example 16 was used as the catalyst. The experiment results were listed in Table 8.

Examples 64-66

Phenylethane was oxidized in the same manner as Example 53 except that, the heteroatom-containing nano-carbon materials prepared in Preparation Examples 29, 33 and 34 were respectively used as the catalysts, the reaction was conducted under 1 MPa at 450° C. The experiment results were listed in Table 8.

Example 67

Phenylethane was oxidized in the same manner as Example 54 except that, the reaction was conducted under 0 MPa at 300° C. The experiment results were listed in Table 8.

TABLE 8

| No. | catalyst source | Reaction time (h) | Phenylethane conversion (wt %) | Phenylethene selectivity (wt %) |
|---|---|---|---|---|
| Example 53 | Preparation Example 29 | 3 | 86.0 | 98.0 |
|  |  | 24 | 79.1 | 91.1 |
| Comparative Example 21 | Comparative Preparation Example 9 | 3 | 44.7 | 49.9 |
|  |  | 24 | 20.5 | 22.9 |
| Comparative Example 22 | Starting nano-carbon material | 3 | 30.1 | 35.2 |
|  |  | 24 | 27.0 | 30.6 |
| Example 54 | Preparation Example 30 | 3 | 84.2 | 98.9 |
|  |  | 24 | 78.3 | 93.0 |
| Comparative Example 23 | Starting nano-carbon material | 3 | 42.3 | 52.4 |
|  |  | 24 | 20.6 | 25.6 |
| Example 55 | Preparation Example 31 | 3 | 79.1 | 91.1 |
|  |  | 24 | 66.8 | 78.0 |
| Example 56 | Preparation Example 32 | 3 | 76.5 | 86.2 |
|  |  | 24 | 69.6 | 79.3 |
| Example 57 | Preparation Example 33 | 3 | 78.2 | 85.2 |
|  |  | 24 | 71.2 | 78.6 |
| Example 58 | Preparation Example 34 | 3 | 82.5 | 88.0 |
|  |  | 24 | 76.7 | 76.5 |
| Example 59 | Preparation Example 35 | 3 | 79.9 | 87.4 |
|  |  | 24 | 72.7 | 80.4 |
| Example 60 | Preparation Example 44 | 3 | 89.4 | 93.1 |
|  |  | 24 | 85.8 | 89.3 |
| Comparative Example 24 | Comparative Preparation Example 16 | 3 | 43.8 | 46.4 |
|  |  | 24 | 42.9 | 43.6 |
| Example 61 | Preparation Example 45 | 3 | 91.7 | 93.9 |
|  |  | 24 | 88.0 | 86.1 |
| Example 62 | Preparation Example 46 | 3 | 75.1 | 86.0 |
|  |  | 24 | 72.0 | 82.6 |
| Example 63 | Preparation Example 47 | 3 | 81.4 | 85.6 |
|  |  | 24 | 78.2 | 83.0 |
| Example 64 | Preparation Example 29 | 3 | 94.6 | 89.1 |
|  |  | 24 | 87.0 | 80.2 |
| Example 65 | Preparation Example 33 | 3 | 80.5 | 77.5 |
|  |  | 24 | 73.2 | 69.7 |
| Example 66 | Preparation Example 34 | 3 | 85.8 | 82.7 |
|  |  | 24 | 78.0 | 81.1 |
| Example 67 | Preparation Example 30 | 3 | 62.5 | 98.8 |
|  |  | 24 | 54.2 | 95.8 |

The present invention also provides the following Solutions: A1. A carbonaceous material, wherein based on the total weight of the carbonaceous material, the carbonaceous material contains 70-99.9 wt % of carbon, 0.05-10 wt % of nitrogen and 0.05-20 wt % of oxygen; wherein in the XPS spectrum of said carbonaceous material, the ratio of the signal value of the peak at 533.13-533.53 eV of the oxygen element to the signal value of the peak at 531.76-532.16 eV of the oxygen element is 0.2-5.

A2. The carbonaceous material according to Solution A1, wherein based on the total weight of the carbonaceous material, the carbonaceous material contains 80-97 wt % of carbon, 0.2-8 wt % of nitrogen and 0.5-15 wt % of oxygen.

A3. The carbonaceous material according to Solution A2, wherein the carbonaceous material contains 85-95 wt % of carbon, 0.5-5 wt % of nitrogen and 2-10 wt % of oxygen.

A4. The carbonaceous material according to any of Solutions A1-A3, wherein in the XPS spectrum of said carbonaceous material, the ratio of the signal value of the peak at 286.21-286.61 of the carbon element to the signal value of the peak at 288.59-288.99 eV of the carbon element is 0.5-2.

A5. The carbonaceous material according to Solution A4, wherein in the XPS spectrum of said carbonaceous material, the sum of the area under curve of the signal in the range of 286.21-286.61 eV of the carbon element and the area under curve of the signal in the range of 288.59-288.99 eV of the carbon element comprises 2-20% of the area under curve of the signal in the range of 280-294 eV of the carbon element.

A6. The carbonaceous material according to any of Solutions A1-A3, wherein the carbonaceous material comprises at least one structure selected from carbon nanotube, graphene, fullerene, nano-carbon particle, active carbon, nano-carbon fiber and nano-adamas.

A7. A process for preparing a carbonaceous material, wherein said process includes the following steps:
(1) mixing a solid carbon source, a precursor and an aqueous hydrogen peroxide solution to produce a mixture; wherein said precursor contains an organic base, said organic base comprises an organic amine and/or a quaternary ammonium base;
(2) Subjecting the mixture obtained in Step (1) to a hydrothermal treatment to produce a hydrothermally treated mixture; and separating a solid from the hydrothermally treated mixture;
(3) Calcining the resulting solid separated from the hydrothermally treated mixture in Step (2).

A8. The process according to Solution A7, wherein the mole ratio of said solid carbon source to the nitrogen element in said organic base is 1:(0.002-50); the mole ratio of said solid carbon source to hydrogen peroxide in said aqueous hydrogen peroxide solution is 1:(0.01-10).

A9. The process according to Solution A7 or A8, wherein the mole ratio of said solid carbon source to the nitrogen element in said organic base is 1:(0.01-10); the mole ratio of said solid carbon source to hydrogen peroxide in said aqueous hydrogen peroxide solution is 1:(0.1-2).

A10. The process according to Solution A9, wherein said aqueous hydrogen peroxide solution has a concentration of 0.5-80 wt %.

A11. The process according to Solution A10, wherein said aqueous hydrogen peroxide solution has a concentration of 1-30 wt %.

A12. The process according to Solution A7, wherein the hydrothermal treatment is conducted at 100-200° C. for 0.5-96 hours.

A13. The process according to Solution A7, wherein the calcination is conducted in an oxygen-containing gas, based on the total volume of the oxygen-containing gas, the oxygen-containing gas has an oxygen content of 2-25 vol %.

A14. The process according to Solution A7 or A13, wherein the calcination temperature is 200-500° C., the calcination time is 2-12 hours.

A15. The process according to Solution A7, wherein said carbon source is at least one selected from the group consisting of carbon nanotube, graphene, fullerene, nano-carbon particle, active carbon, nano-carbon fiber and nano-adamas.

A16. The process according to Solution A7, wherein said organic amine comprises at least one of an aliphatic amine, an alcoholic amine, an acid amide, an alicyclic amine and an aromatic amine; said aliphatic amine is at least one selected from the group consisting of ethylamine, n-propylamine, n-butylamine, di-n-propylamine, butylene diamine and hexylene diamine; said alcoholic amine is at least one selected from the group consisting of monoethanolamine, diethanolamine and triethanolamine; said quaternary ammonium base is at least one selected from the group consisting of tetramethylammonium hydroxide, tetraethylammonium hydroxide, tetrapropyl ammonium hydroxide and tetrabutylammonium hydroxide.

A17. The process according to Solution A7, wherein said aqueous hydrogen peroxide solution has a hydrogen peroxide content of 0.5-50 wt %.

A18. The carbonaceous material obtained with the process according to any of Solutions A7-A17.

A19. Use of said carbonaceous material according to any of Solutions A1-A6 and A18 in the catalytic oxidation of hydrocarbons A20. Use according to Solution A19, wherein said hydrocarbon has a carbon atom number of 2-12, said hydrocarbon comprises at least one of an alkane, an alkene and an aromatic hydrocarbon containing alkyl group(s).

A21. Use according to Solution A20, wherein said hydrocarbon comprises at least one of butane, 1-butene, ethylbenzene, propane, ethane and pentane.

B1. A carbonaceous material, wherein based on the total weight of the carbonaceous material, the carbonaceous material contains 70-99.75 wt % of a carbon element, 0.05-10 wt % of a nitrogen element and 0.2-20 wt % of an oxygen element; wherein in the X-ray photoelectron spectroscopy of the carbonaceous material, the ratio of the amount of the oxygen element as determined with the peak(s) in the range of 533.1-533.5 eV to the amount of the oxygen element as determined with the peak(s) in the range of 531.8-532.2 eV is 0.2-5.

B2. The carbonaceous material according to Solution B1, wherein based on the total weight of the carbonaceous material, the carbonaceous material contains 80-97 wt % of a carbon element, 0.2-8 wt % of a nitrogen element and 0.5-15 wt % of an oxygen element, in the X-ray photoelectron spectroscopy of the carbonaceous material, the ratio of the amount of the oxygen element as determined with the peak(s) in the range of 533.1-533.5 eV to the amount of the oxygen element as determined with the peak(s) in the range of 531.8-532.2 eV is 0.5-2.

B3. The carbonaceous material according to Solution B2, wherein based on the total weight of the carbonaceous material, the carbonaceous material contains 85-95 wt % of a carbon element, 0.5-5 wt % of a nitrogen element and 2-10 wt % of an oxygen element, in the X-ray photoelectron spectroscopy of the carbonaceous material, the ratio of the amount of the oxygen element as determined with the peak(s) in the range of 533.1-533.5 eV to the amount of the oxygen element as determined with the peak(s) in the range of 531.8-532.2 eV is 0.6-1.8.

B4. The carbonaceous material according to any of Solutions B1-B3, wherein in the X-ray photoelectron spectroscopy of the carbonaceous material, the ratio of the amount of the nitrogen element determined with the peak(s) in the range of 398.0-400.5 eV to the amount of the nitrogen element determined with the peak(s) in the range of 395.0-405.0 eV is 0.5-1;

the ratio of the amount of the nitrogen element determined with the peak(s) in the range of 400.6-401.5 eV to the amount of the nitrogen element determined with the peak(s) in the range of 395.0-405.0 eV is 0-0.5.

B5. The carbonaceous material according to any of Solutions B1-B3, wherein in the X-ray photoelectron spectroscopy of the carbonaceous material, the ratio of the amount of the carbon element as determined with the peak(s) in the range of 283.8-284.2 eV to the amount of the carbon element as determined with the peak(s) in the range of 280.0-294.0 eV is 0.6-1; the ratio of the sum of the amount of the carbon element as determined with the peak(s) in the range of 286.2-286.6 eV and the amount of the carbon element as determined with the peak(s) in the range of 288.6-289.0 eV to the amount of the carbon element as determined with the peak(s) in the range of 280.0-294.0 eV is 0.02-0.2;

the ratio of the amount of the carbon element as determined with the peak(s) in the range of 286.2-286.6 eV to the amount of the carbon element as determined with the peak(s) in the range of 288.6-289.0 eV is 0.3-2.

B7. The carbonaceous material according to any of Solutions B1-B3, wherein said carbonaceous material has a $w_{500}/w_{800}$ of 0.02-0.5; wherein $w_{800}$ represents the weight reduction rate of said carbonaceous material at 800° C. vs. at 400° C. in a condition of an air atmosphere, an initial temperature of 25° C. and a temperature rise rate of 10° C./min, $w_{500}$ represents the weight reduction rate of said carbonaceous material at 500° C. vs. at 400° C. in a condition of an air atmosphere, an initial temperature of 25° C. and a temperature rise rate of 10° C./min.

B8. The carbonaceous material according to any of Solutions B1-B3, wherein the structural form of said carbonaceous material comprises at least one structural form selected from carbon nanotube, graphene, fullerene, nano-carbon particle, active carbon, thin-layer graphite, nano-carbon fiber and nano-adamas.

B9. A process for preparing a carbonaceous material, wherein said process includes the following steps:

(1) mixing a solid carbon source, a precursor and an aqueous hydrogen peroxide solution to produce a mixture; wherein said precursor contains an organic base source, said organic base source comprises an organic amine and/or a quaternary ammonium base;

(2) Subjecting the mixture obtained in Step (1) to a hydrothermal treatment to produce a hydrothermally treated mixture; and separating a solid from the hydrothermally treated mixture;

(3) Calcining the resulting solid separated from the hydrothermally treated mixture in Step (2).

B10. The process according to Solution B9, wherein the mole ratio of the carbon element in said solid carbon source to the nitrogen element in said organic base source is 1:(0.002-50); the mole ratio of the carbon element in said solid carbon source to hydrogen peroxide in said aqueous hydrogen peroxide solution is 1:(0.01-10).

B11. The process according to Solution B9 or B10, wherein the mole ratio of the carbon element in said solid carbon source to the nitrogen element in said organic base source is 1:(0.01-10); the mole ratio of the carbon element in said solid carbon source to hydrogen peroxide in said aqueous hydrogen peroxide solution is 1:(0.1-2).

B12. The process according to Solution B9, wherein said aqueous hydrogen peroxide solution has a concentration of 0.5-80 wt %.

B13. The process according to Solution B9, wherein the hydrothermal treatment is conducted at 105-200° C.; the hydrothermal treatment is conducted for 0.5-96 hours; the calcination temperature is 200-500° C., the calcination time is 0.5-48 hours.

B14. The process according to Solution B13, wherein the hydrothermal treatment is conducted at 120-180° C.; the calcination temperature is 300-450° C.

B15. The process according to Solution B9, wherein the calcination is conducted in an oxygen-containing gas, based on the total volume of the oxygen-containing gas, the oxygen-containing gas has an oxygen content of 2-25 vol %.

B16. The process according to Solution B9, wherein said carbon source is at least one selected from the group consisting of carbon nanotube, graphene, fullerene, nano-carbon particle, thin-layer graphite, active carbon, nano-carbon fiber and nano-adamas.

B17. The process according to Solution B9, wherein said organic amine comprises at least one of an aliphatic amine, an alcoholic amine, an acid amide, an alicyclic amine and an aromatic amine; said aliphatic amine is at least one selected from the group consisting of ethylamine, n-propylamine, n-butylamine, di-n-propylamine, butylene diamine and hexylene diamine; said alcoholic amine is at least one selected from the group consisting of monoethanolamine, diethanolamine and triethanolamine; said quaternary ammonium base is at least one selected from the group consisting of tetramethylammonium hydroxide, tetraethylammonium hydroxide, tetrapropyl ammonium hydroxide and tetrabutylammonium hydroxide; said acid amide is at least one selected from the group consisting of methanamide, ethanamide, propanamide, butanamide, isobutanamide, acrylamide, polyacrylamide, caprolactam, dimethylmethanamide and dimethylethanamide; said alicyclic amine is at least one selected from the group consisting of triethylene diamine, diethylene triamine, hexamethylene tetraamine, hexamethyleneimine, triethylene diamine, ethyleneimine, morpholine, piperazine and cyclohexylamine; said aromatic amine is at least one selected from the group consisting of aniline, diphenylamine, benzidine, o-phenylene diamine, m-phenylene diamine, p-phenylene diamine, o-methylaniline, m-methylaniline, p-methylaniline, 2,3-dimethylaniline, 2,4-dimethylaniline, 2,5-dimethylaniline, 2,6-dimethylaniline, 3,4-dimethylaniline, 3,5-dimethylaniline, 2,4,6-trimethylaniline, o-ethylaniline, N-butylaniline and 2,6-diethylaniline.

B18. The carbonaceous material obtained with the process according to any of Solutions B9-B17.

B19. Use of said carbonaceous material according to any of Solutions B1-B8 and B18 in the catalytic oxidation of hydrocarbons.

B20. Use according to Solution 19, wherein said hydrocarbon has a carbon atom number of 2-15, said hydrocarbon comprises at least one of an alkane, an alkene and an aromatic hydrocarbon containing alkyl group(s); said alkyl contains at least two carbon atoms.

B21. Use according to Solution B20, wherein said hydrocarbon comprises at least one of butane, 1-butene, ethylbenzene, propane, ethane and pentane.

C1. A carbonaceous material, wherein based on the total weight of the carbonaceous material, the carbonaceous material contains 80-96 wt % of carbon, 0.5-5 wt % of nitrogen and 2-15 wt % of oxygen; wherein in the XPS spectrum of said carbonaceous material, the ratio of the signal value of the oxygen in the range of 533.16-533.56 eV to the signal value of the oxygen in the range of 531.85-532.25 eV is 0.2-5.

C2. The carbonaceous material according to Solution C1, wherein based on the total weight of the carbonaceous material, the carbonaceous material contains 90-95 wt % of carbon, 0.8-2 wt % of nitrogen and 4-10 wt % of oxygen.

C3. The carbonaceous material according to Solution C1 or C2, wherein in the XPS spectrum of said carbonaceous material, the ratio of the signal value of the carbon in the range of 286.21-286.61 eV to the signal value of the carbon in the range of 288.59-288.99 eV is 0.5-2.

C4. The carbonaceous material according to Solution C1 or C2, wherein said carbonaceous material comprises at least one structure selected from carbon nanotube, graphene, fullerene, nano-carbon particle, active carbon, nano-carbon fiber and nano-adamas.

C5. A process for preparing a carbonaceous material, wherein said process includes the following steps:

(1) Mixing a solid carbon source, a precursor and water to produce a mixture; wherein said precursor contains an organic base, said organic base comprises an organic amine and/or a quaternary ammonium base;

(2) Subjecting the mixture obtained in Step (1) to a hydrothermal treatment to produce a hydrothermally treated mixture; and separating a solid from the hydrothermally treated mixture;

(3) Calcining the resulting solid separated from the hydrothermally treated mixture in Step (2).

C6. The process according to Solution C5, wherein the weight ratio of the carbon element in said solid carbon source, the nitrogen element in said organic base, and water is 1:(0.001-0.5):(1-100).

C7. The process according to Solution C6, wherein the weight ratio of the carbon element in said solid carbon source, the nitrogen element in said organic base, and water is 1:(0.01-0.05):(5-20).

C8. The process according to any of Solutions C5-C7, wherein the hydrothermal treatment is conducted at 100-200° C. for 0.5-144 hours.

C9. The process according to any of Solutions C5-C7, wherein the calcination temperature is 200-500° C., the calcination time is 2-12 hours.

C10. The process according to Solution C9, wherein the calcination is conducted in an oxygen-containing gas, based on the total volume of the oxygen-containing gas, the oxygen-containing gas has an oxygen content of 2-25 vol %.

C11. The process according to any of Solutions C5-C7, wherein said carbon source is at least one selected from the group consisting of carbon nanotube, active carbon, graphene, fullerene, nano-carbon fiber, nano-carbon particle, and nano-adamas.

C12. The process according to any of Solutions C5-C7, wherein said organic amine comprises at least one of an aliphatic amine, an alcoholic amine, an acid amide, an alicyclic amine and an aromatic amine; said aliphatic amine is at least one selected from the group consisting of ethylamine, n-propylamine, n-butylamine, di-n-propylamine, butylene diamine and hexylene diamine; said organic alcoholic amine is at least one selected from the group consisting of monoethanolamine, diethanolamine and triethanolamine; said quaternary ammonium base is at least one selected from the group consisting of tetramethylammonium hydroxide, tetraethylammonium hydroxide, tetrapropyl ammonium hydroxide and tetrabutylammonium hydroxide.

C13. The carbonaceous material obtained with the process according to any of Solutions C5-C12.

C14. Use of the carbonaceous material according to any of Solutions C1-C4 and C13 in the catalytic oxidative dehydrogenation of hydrocarbons.

C15. A process for the oxidization of hydrocarbons, which process comprises: contacting a gas containing hydrocarbons and oxygen with a catalyst in a condition of the catalytic oxidative dehydrogenation of hydrocarbons; wherein said catalyst comprises the carbonaceous material according to any of Solutions C1-C4 and C13.

C16. The process according to Solution C15, wherein said hydrocarbon has a carbon atom number of 2-12, said hydrocarbon comprises at least one of an alkane, an alkene and an aromatic hydrocarbon containing alkyl group(s).

C17. The process according to Solution C16, wherein said hydrocarbon comprises at least one of butane, 1-butene, ethylbenzene, propane, ethane and pentane.

C18. The process according to Solution C15, wherein the mole ratio of hydrocarbon to oxygen is (0.1-10):1.

C19. The process according to Solution C15 or C18, wherein the gas containing hydrocarbons and oxygen further contains a carrier gas, said carrier gas comprises at least one of nitrogen, $CO_2$ and water vapor.

C20. The process according to Solution C19, wherein in the gas containing hydrocarbons and oxygen, the total concentration of hydrocarbons and oxygen is 1-50 vol %.

C21. The process according to Solution C15, wherein the condition of the catalytic oxidative dehydrogenation of hydrocarbons comprises: the contacting temperature is 300-600° C., the pressure is 0.1-60 MPa; based on the total volume of the gas containing hydrocarbons and oxygen, the volume space velocity for the gas passing through the catalyst is 1-6000 $h^{-1}$.

D1. A carbonaceous material, wherein based on the total weight of the carbonaceous material, the carbonaceous material contains 80-98.9 wt % of a carbon element, 0.1-7 wt % of a nitrogen element and 1-15 wt % of an oxygen element; wherein in the X-ray photoelectron spectroscopy of the carbonaceous material, the ratio of the amount of the oxygen element as determined with the peak(s) in the range of 533.1-533.5 eV to the amount of the oxygen element as determined with the peak(s) in the range of 531.8-532.2 eV is 0.2-5.

D2. The carbonaceous material according to Solution D1, wherein based on the total weight of the carbonaceous material, the carbonaceous material contains 85-97 wt % of a carbon element, 0.2-5 wt % of a nitrogen element and 2-10 wt % of an oxygen element, in the X-ray photoelectron spectroscopy of the carbonaceous material, the ratio of the amount of the oxygen element as determined with the peak(s) in the range of 533.1-533.5 eV to the amount of the oxygen element as determined with the peak(s) in the range of 531.8-532.2 eV is 0.5-2.

D3. The carbonaceous material according to Solution D2, wherein based on the total weight of the carbonaceous material, the carbonaceous material contains 90-95 wt % of a carbon element, 0.5-4 wt % of a nitrogen element and 4-8 wt % of an oxygen element, in the X-ray photoelectron spectroscopy of the carbonaceous material, the ratio of the amount of the oxygen element as determined with the peak(s) in the range of 533.1-533.5 eV to the amount of the oxygen element as determined with the peak(s) in the range of 531.8-532.2 eV is 0.6-1.8.

D4. The carbonaceous material according to any of Solutions D1-D3, wherein in the X-ray photoelectron spectroscopy of the carbonaceous material, the ratio of the amount of the nitrogen element determined with the peak(s) in the range of 398.0-400.5 eV to the amount of the nitrogen element determined with the peak(s) in the range of 395.0-405.0 eV is 0.5-1;

the ratio of the amount of the nitrogen element determined with the peak(s) in the range of 400.6-401.5 eV to the amount of the nitrogen element determined with the peak(s) in the range of 395.0-405.0 eV is 0-0.5.

D5. The carbonaceous material according to any of Solutions D1-D3, wherein in the X-ray photoelectron spectroscopy of the carbonaceous material, the ratio of the amount of the carbon element as determined with the peak(s) in the range of 283.8-284.2 eV to the amount of the carbon element as determined with the peak(s) in the range of 280.0-294.0 eV is 0.6-1; the ratio of the sum of the amount of the carbon element as determined with the peak(s) in the range of 286.2-286.6 eV and the amount of the carbon element as determined with the peak(s) in the range of 288.6-289.0 eV to the amount of the carbon element as determined with the peak(s) in the range of 280.0-294.0 eV is 0.01-0.2;

the ratio of the amount of the carbon element as determined with the peak(s) in the range of 286.2-286.6 eV to the amount of the carbon element as determined with the peak(s) in the range of 288.6-289.0 eV is 0.2-2.

D7. The carbonaceous material according to any of Solutions D1-D3, wherein said carbonaceous material has a $w_{500}/w_{800}$ of 0.02-0.5; wherein $w_{800}$ represents the weight reduction rate of said carbonaceous material at 800° C. vs. at 400° C. in a condition of an air atmosphere, an initial temperature of 25° C. and a temperature rise rate of 10° C./min, $w_{500}$ represents the weight reduction rate of said carbonaceous material at 500° C. vs. at 400° C. in a condition of an air atmosphere, an initial temperature of 25° C. and a temperature rise rate of 10° C./min.

D8. The carbonaceous material according to any of Solutions D1-D3, wherein the structural form of said carbonaceous material comprises at least one structural form selected from carbon nanotube, graphene, fullerene, nanocarbon particle, active carbon, thin-layer graphite, nanocarbon fiber and nano-adamas.

D9. A process for preparing a carbonaceous material, wherein said process includes the following steps:

(1) Mixing a solid carbon source, a precursor and water to produce a mixture; wherein said precursor contains an organic base, said organic base comprises an organic amine and/or a quaternary ammonium base;

(2) Subjecting the mixture obtained in Step (1) to a hydrothermal treatment to produce a hydrothermally treated mixture; and separating a solid from the hydrothermally treated mixture;

(3) Calcining the resulting solid separated from the hydrothermally treated mixture in Step (2). D10. The process according to Solution D9, wherein the mole ratio of the carbon element in said solid carbon source to the nitrogen element in said organic base is 1:(0.001-0.5); the weight ratio of the carbon element in said solid carbon source to water is 1:(1-100).

D11. The process according to Solution D10, wherein the mole ratio of the carbon element in said solid carbon source to the nitrogen element in said organic base is 1:(0.01-0.05); the weight ratio of the carbon element in said solid carbon source to water is 1:(5-20).

D12. The process according to Solution D9, wherein the hydrothermal treatment is conducted at 105-200° C. for 0.5-96 hours; the calcination temperature is 200-500° C., the calcination time is 0.5-48 hours.

D13. The process according to Solution D12, wherein the hydrothermal treatment is conducted at 120-180° C.; the calcination temperature is 300-450° C.

D14. The process according to Solution D9, wherein the calcination is conducted in an oxygen-containing gas, based on the total volume of the oxygen-containing gas, the oxygen-containing gas has an oxygen content of 2-25 vol %.

D15. The process according to Solution D9, wherein said carbon source is at least one selected from the group consisting of carbon nanotube, graphene, fullerene, nanocarbon particle, thin-layer graphite, active carbon, nanocarbon fiber and nano-adamas.

D16. The process according to Solution D9, wherein said organic amine comprises at least one of an aliphatic amine, an alcoholic amine, an acid amide, an alicyclic amine and an aromatic amine; said aliphatic amine is at least one selected from the group consisting of ethylamine, n-propylamine, n-butylamine, di-n-propylamine, butylene diamine and hexylene diamine; said alcoholic amine is at least one selected from the group consisting of monoethanolamine, diethanolamine and triethanolamine; said quaternary ammonium base is at least one selected from the group consisting of tetramethylammonium hydroxide, tetraethylammonium hydroxide, tetrapropyl ammonium hydroxide and tetrabutylammonium hydroxide; said acid amide is at least one selected from the group consisting of methanamide, ethanamide, propanamide, butanamide, isobutanamide, acrylamide, polyacrylamide, caprolactam, dimethylmethanamide and dimethylethanamide; said alicyclic amine is at least one selected from the group consisting of triethylene diamine, diethylene triamine, hexamethylene tetramine, hexamethyleneimine, triethylene diamine, ethyleneimine, morpholine, piperazine and cyclohexylamine; said aromatic amine is at least one selected from the group consisting of aniline, diphenylamine, benzidine, o-phenylene diamine, m-phenylene diamine, p-phenylene diamine, o-methylaniline, m-methylaniline, p-methylaniline, 2,3-dimethylaniline, 2,4-dimethylaniline, 2,5-dimethylaniline, 2,6-dimethylaniline, 3,4-dimethylaniline, 3,5-dimethylaniline, 2,4,6-trimethylaniline, o-ethylaniline, N-butylaniline and 2,6-diethylaniline.

D17. The carbonaceous material obtained with the process according to any of Solutions D9-D16.

D18. Use of said carbonaceous material according to any of solutions D1-D8 and D17 in catalytic oxidation of hydrocarbons.

D19. A process for the oxidization of hydrocarbons, which process comprises contacting a gas containing hydrocarbons and oxygen with a catalyst in a condition of the catalytic oxidation of hydrocarbons; wherein said catalyst comprises the carbonaceous material according to any of Solutions D1-D8 and D17.

D20. The process according to Solution D19, wherein said hydrocarbon has a carbon atom number of 2-15, said hydrocarbon comprises at least one of an alkane, an alkene and an aromatic hydrocarbon containing alkyl group(s); said alkyl contains at least two carbon atoms.

D21. The process according to Solution D20, wherein said hydrocarbon comprises at least one of butane, 1-butene, ethylbenzene, propane, ethane and pentane.

D22. The process according to Solution D19, wherein the mole ratio of hydrocarbon to oxygen is (0.1-10):1.

D23. The process according to Solution D19, wherein the condition of the catalytic oxidation of hydrocarbons comprises: the contacting temperature is 300-600° C., the contacting pressure is 0.1-40 MPa; based on the total volume of the gas containing hydrocarbons and oxygen, the volume space velocity for the gas passing through the catalyst is 1-6000 $h^{-1}$.

E1. A process for catalytic dehydrogenation of hydrocarbons, which process comprises contacting a gas containing hydrocarbons with a catalyst in a condition of catalytic dehydrogenation of hydrocarbons; wherein said catalyst contains a carbonaceous material; based on the total weight of the carbonaceous material, said carbonaceous material contains 70-99.9 wt % of carbon, 0.05-10 wt % of nitrogen and 0.05-20 wt % of oxygen; wherein in the XPS spectrum of said carbonaceous material, the ratio of the signal value of the peak at 533.13-533.53 eV of the oxygen element to the signal value of the peak at 531.76-532.16 eV of the oxygen element is 0.2-5.

E2. The process according to Solution E1, wherein based on the total weight of the carbonaceous material, the carbonaceous material contains 80-97 wt % of carbon, 0.2-8 wt % of nitrogen and 0.5-15 wt % of oxygen.

E3. The process according to Solution E2, wherein said carbonaceous material contains 85-95 wt % of carbon, 0.5-5 wt % of nitrogen and 2-10 wt % of oxygen.

E4. The process according to any of Solution E1-E3, wherein in the XPS spectrum of said carbonaceous material, the ratio of the signal value of the peak at 286.21-286.61 of the carbon element to the signal value of the peak at 288.59-288.99 eV of the carbon element is 0.5-2.

E5. The process according to Solution E4, wherein in the XPS spectrum of said carbonaceous material, the sum of the area under curve of the signal in the range of 286.21-286.61 eV of the carbon element and the area under curve of the signal in the range of 288.59-288.99 eV of the carbon element comprises 2-20% of the area under curve of the signal in the range of 280-294 eV of the carbon element.

E6. The process according to any of Solution E1-E3, wherein in the XPS of said carbonaceous material, a peak signal of the carbon element appears at 283.96-284.36 eV.

E7. The process according to any of Solution E1-E3, wherein said carbonaceous material comprises at least one structure selected from carbon nanotube, graphene, fullerene, nano-carbon particle, active carbon, nano-carbon fiber and nano-adamas.

E8. The process according to Solution E1, wherein said hydrocarbon has a carbon atom number of 2-12, said hydrocarbon comprises at least one of an alkane, an alkene and an aromatic hydrocarbon containing alkyl group(s).

E9. The process according to Solution E8, wherein said hydrocarbon comprises at least one of butane, 1-butene, ethylbenzene, propane, ethane and pentane.

E10. The process according to Solution E1, wherein said gas containing hydrocarbons further contains oxygen, and the mole ratio of hydrocarbon to oxygen is (0.1-10):1.

E11. The process according to Solution E10, wherein said gas containing hydrocarbons further contains a carrier gas, said carrier gas comprises at least one of nitrogen, $CO_2$ and water vapor.

E12. The process according to Solution E11, wherein in said gas containing hydrocarbons, the total concentration of hydrocarbons and oxygen is 1-50 vol %.

E13. The process according to Solution E1, wherein the condition of catalytic dehydrogenation of hydrocarbons comprises: the contacting temperature is 300-600° C., the pressure is 0.1-60 MPa; based on the total volume of the gas containing hydrocarbons, the volume space velocity for the gas passing through the catalyst is 1-6000 $h^{-1}$.

E14. The process according to Solution E1, wherein said hydrocarbon comprises butane; based on the total weight of the carbonaceous material, said carbonaceous material contains 85-95 wt % of carbon, 0.5-5 wt % of nitrogen and 2-10 wt % of oxygen; said carbonaceous material comprises a structure of carbon nanotube; said gas containing hydrocarbons further contains oxygen, the mole ratio of said hydrocarbon to oxygen is (0.1-10):1; in said gas containing hydrocarbons, the total concentration of said hydrocarbon and oxygen is 1-50 vol %; the condition of catalytic dehydrogenation of hydrocarbons comprises: the contacting temperature is 400-500° C., the pressure is 0.1-60 MPa; based on the total volume of the gas containing hydrocarbons, the volume space velocity for the gas passing through the catalyst is 10-4000 $h^{-1}$.

E15. The process according to Solution E1, wherein said hydrocarbon comprises propane; based on the total weight of the carbonaceous material, said carbonaceous material contains 85-95 wt % of carbon, 0.5-2.5 wt % of nitrogen and 2-10 wt % of oxygen; said carbonaceous material comprises a structure of carbon nanotube; said gas containing hydrocarbons further contains oxygen, the mole ratio of said hydrocarbon to oxygen is (0.05-2):1; in said gas containing hydrocarbons, the total concentration of said hydrocarbon and oxygen is 10-30 vol %; the condition of catalytic dehydrogenation of hydrocarbons comprises: the contacting temperature is 300-400° C., the pressure is 0.1-60 MPa; based on the total volume of the gas containing hydrocarbons, the volume space velocity for the gas passing through the catalyst is 100-2000 $h^{-1}$.

E16. The process according to Solution E1, wherein said hydrocarbon comprises ethylbenzene; based on the total weight of the carbonaceous material, said carbonaceous material contains 85-95 wt % of carbon, 2.5-5 wt % of nitrogen and 2-10 wt % of oxygen; said carbonaceous material comprises a structure of carbon nanotube; the condition of catalytic dehydrogenation of hydrocarbons comprises: the contacting temperature is 400-500° C., the pressure is 0.1-60 MPa; based on the total volume of the gas containing hydrocarbons, the volume space velocity for the gas passing through the catalyst is 10-4000 $h^{-1}$.

F1. A process for catalytic dehydrogenation of hydrocarbons, which process comprises contacting a gas containing hydrocarbons with a catalyst in a condition of catalytic dehydrogenation of hydrocarbons; wherein said catalyst contains a carbonaceous material; based on the total weight of the carbonaceous material, said carbonaceous material contains 70-99.75 wt % of a carbon element, 0.05-10 wt % of a nitrogen element and 0.2-20 wt % of an oxygen element; wherein in the X-ray photoelectron spectroscopy of the carbonaceous material, the ratio of the amount of the oxygen element as determined with the peak(s) in the range of 533.1-533.5 eV to the amount of the oxygen element as determined with the peak(s) in the range of 531.8-532.2 eV is 0.2-5.

F2. The process according to Solution F1, wherein based on the total weight of the carbonaceous material, the carbonaceous material contains 80-97 wt % of a carbon element, 0.2-8 wt % of a nitrogen element and 0.5-15 wt % of an oxygen element, in the X-ray photoelectron spectroscopy of the carbonaceous material, the ratio of the amount of the oxygen element as determined with the peak(s) in the range of 533.1-533.5 eV to the amount of the oxygen element as determined with the peak(s) in the range of 531.8-532.2 eV is 0.5-2.

F3. The process according to Solution F2, wherein based on the total weight of the carbonaceous material, the carbonaceous material contains 85-95 wt % of a carbon element, 0.5-5 wt % of a nitrogen element and 2-10 wt % of an oxygen element, in the X-ray photoelectron spectroscopy of the carbonaceous material, the ratio of the amount of the oxygen element as determined with the peak(s) in the range of 533.1-533.5 eV to the amount of the oxygen element as determined with the peak(s) in the range of 531.8-532.2 eV is 0.6-1.8.

F4. The process according to any of Solutions F1-F3, wherein in the X-ray photoelectron spectroscopy of the carbonaceous material, the ratio of the amount of the nitrogen element determined with the peak(s) in the range of 398.0-400.5 eV to the amount of the nitrogen element determined with the peak(s) in the range of 395.0-405.0 eV is 0.5-1;

the ratio of the amount of the nitrogen element determined with the peak(s) in the range of 400.6-401.5 eV to the amount of the nitrogen element determined with the peak(s) in the range of 395.0-405.0 eV is 0-0.5.

F5. The process according to any of Solutions F1-F3, wherein in the X-ray photoelectron spectroscopy of the carbonaceous material, the ratio of the amount of the carbon element as determined with the peak(s) in the range of 283.8-284.2 eV to the amount of the carbon element as determined with the peak(s) in the range of 280.0-294.0 eV is 0.6-1;

in the X-ray photoelectron spectroscopy, the ratio of the sum of the amount of the carbon element as determined with the peak(s) in the range of 286.2-286.6 eV and the amount of the carbon element as determined with the peak(s) in the range of 288.6-289.0 eV to the amount of the carbon element as determined with the peak(s) in the range of 280.0-294.0 eV is 0.02-0.2;

the ratio of the amount of the carbon element as determined with the peak(s) in the range of 286.2-286.6 eV to the amount of the carbon element as determined with the peak(s) in the range of 288.6-289.0 eV is 0.3-2.

F6. The process according to any of Solutions F1-F3, wherein in the different X-ray micro zones having the same area in the surface of the carbonaceous material, the variation coefficients for the contents of the nitrogen element and the oxygen element are 20% or lower respectively.

F7. The process according to any of Solutions F1-F3, wherein said carbonaceous material has a $w_{500}/w_{800}$ of 0.02-0.5; wherein $w_{800}$ represents the weight reduction rate of said carbonaceous material at 800° C. vs. at 400° C. in a condition of an air atmosphere, an initial temperature of 25° C. and a temperature rise rate of 10° C./min, $w_{500}$ represents the weight reduction rate of said carbonaceous material at 500° C. vs. at 400° C. in a condition of an air atmosphere, an initial temperature of 25° C. and a temperature rise rate of 10° C./min.

F8. The process according to any of Solutions F1-F3, wherein the structural form of said carbonaceous material comprises at least one structural form selected from carbon nanotube, graphene, fullerene, nano-carbon particle, active carbon, thin-layer graphite, nano-carbon fiber and nano-adamas.

F9. The process according to Solution F1, wherein said hydrocarbon has a carbon atom number of 2-15, said hydrocarbon comprises at least one of an alkane, an alkene and an aromatic hydrocarbon containing alkyl group(s); said alkyl contains at least two carbon atoms.

F10. The process according to Solution F8, wherein said hydrocarbon comprises at least one of butane, 1-butene, ethylbenzene, propane, ethane and pentane.

F11. The process according to Solution F1, wherein said gas containing hydrocarbons further contains oxygen, and the mole ratio of hydrocarbon to oxygen is (0.1-10):1.

F12. The process according to Solution F11, wherein said gas containing hydrocarbons further contains a carrier gas, said carrier gas comprises at least one of nitrogen, $CO_2$ and water vapor.

F13. The process according to Solution F12, wherein in said gas containing hydrocarbons, the total concentration of hydrocarbons and oxygen is 1-50 vol %.

F14. The process according to Solution F1, wherein the condition of catalytic dehydrogenation of hydrocarbons comprises: the contacting temperature is 300-600° C., the pressure is 0.1-60 MPa; based on the total volume of the gas containing hydrocarbons, the volume space velocity for the gas passing through the catalyst is 1-6000 $h^{-1}$.

F15. The process according to Solution F1, wherein said hydrocarbon comprises butane; based on the total weight of the carbonaceous material, said carbonaceous material contains 85-95 wt % of a carbon element, 0.5-5 wt % of a nitrogen element and 2-10 wt % of an oxygen element; said carbonaceous material comprises a structure of carbon nanotube; said gas containing hydrocarbons further contains oxygen, the mole ratio of said hydrocarbon to oxygen is (0.1-10):1; in said gas containing hydrocarbons, the total concentration of said hydrocarbon and oxygen is 1-50 vol %; the condition of catalytic dehydrogenation of hydrocarbons comprises: the contacting temperature is 350-500° C., the pressure is 0.1-5 MPa; based on the total volume of the gas containing hydrocarbons, the volume space velocity for the gas passing through the catalyst is 10-2000 $h^{-1}$.

F16. The process according to Solution F1, wherein said hydrocarbon comprises propane; based on the total weight of the carbonaceous material, said carbonaceous material contains 85-95 wt % of a carbon element, 0.5-5 wt % of a nitrogen element and 2-10 wt % of an oxygen element; said carbonaceous material comprises a structure of carbon nanotube; said gas containing hydrocarbons further contains oxygen, the mole ratio of said hydrocarbon to oxygen is (0.05-2):1; in said gas containing hydrocarbons, the total concentration of said hydrocarbon and oxygen is 10-30 vol %; the condition of catalytic dehydrogenation of hydrocarbons comprises: the contacting temperature is 400-550° C., the pressure is 0.1-5 MPa; based on the total volume of the gas containing hydrocarbons, the volume space velocity for the gas passing through the catalyst is 5-1000 $h^{-1}$.

F17. The process according to Solution F1, wherein said hydrocarbon comprises ethylbenzene; based on the total weight of the carbonaceous material, said carbonaceous material contains 85-95 wt % of a carbon element, 0.5-5 wt % of a nitrogen element and 2-10 wt % of an oxygen element; said carbonaceous material comprises a structure of carbon nanotube; the condition of catalytic dehydrogenation of hydrocarbons comprises: the contacting temperature is 300-500° C., the pressure is 0.1-5 MPa; based on the total volume of the gas containing hydrocarbons, the volume space velocity for the gas passing through the catalyst is 10-4000 $h^{-1}$.

G1. A heteroatom-containing nano-carbon material, said heteroatom-containing nano-carbon material contains a carbon element, an oxygen element and a nitrogen element, the content of the oxygen element is 1-6 wt %, the content of the nitrogen element is 0.5-5 wt %, the content of the carbon element is 80-96 wt %, the element contents of said heteroatom-containing nano-carbon material are determined with the XPS method as described herein;

In said heteroatom-containing nano-carbon material, the amount of the oxygen element determined with the peak(s) in the range of 531.85-532.25 eV in the X-ray photoelectron spectroscopy is $I_O^c$, the amount of the oxygen element determined with the peak(s) in the range of 533.16-533.56 eV in the X-ray photoelectron spectroscopy is $I_O^e$, $I_O^c/I_O^e$ is 1:(0.2-5) and/or the content of the carbon element determined with the peak(s) in the range of 288.59-288.99 eV in the X-ray photoelectron spectroscopy is $I_C^c$, the content of the carbon element determined with the peak(s) in the range of 286.21-286.61 eV in the X-ray photoelectron spectroscopy is $I_C^e$, $I_C^c/I_C^e$ is 1:(0.5-2).

G2. The carbonaceous material according to Solution G1, wherein the content of the oxygen element is 2-6 wt %, the content of the nitrogen element is 0.5-2 wt %, the content of the carbon element is 92-96 wt %.

G3. The carbonaceous material according to Solution G1, wherein the content of the oxygen element is 4-10 wt %, the content of the nitrogen element is 0.8-2 wt %, the content of the carbon element is 90-95 wt %.

G4. The carbonaceous material according to any of Solutions G1-G3, wherein said carbonaceous material contains at least one structure selected from carbon nanotube, graphene, fullerene, nano-carbon particle, active carbon, nano-carbon fiber and nano-adamas.

G5. A process for preparing a carbonaceous material, wherein said process includes the following steps:

(1) Mixing a solid carbon source, a precursor and water to produce a mixture; wherein said precursor contains an organic base, said organic base comprises an organic amine and/or a quaternary ammonium base;

(2) Subjecting the mixture obtained in Step (1) to a hydrothermal treatment to produce a hydrothermally treated mixture; and separating a solid from the hydrothermally treated mixture;

(3) Drying and calcining the resulting solid separated from the hydrothermally treated mixture in Step (2).

G6. The process according to Solution G5, wherein the weight ratio of the carbon element in said solid carbon source to the nitrogen element in said organic base is 1:(0.001-0.5), 1:(0.01-0.05), 1:0.03, 1:0.01, 1:0.05, 1:0.001 or 1:0.45.

G7. The process according to any of Solutions G5-G6, wherein the weight ratio of the carbon element in said solid carbon source to water is 1:(1-100), 1:(5-20), 1:1, 1:5, 1:10, 1:20, or 1:100.

G8. The process according to any of Solutions G5-G7, wherein the hydrothermal treatment is conducted at 100-200° C.; more preferably 110-180° C. for 0.5-144 hours, 0.5-96 hours, preferably 2-72 hours.

G9. The process according to any of Solutions G5-G8, wherein the hydrothermal treatment is conducted under an autogenous pressure.

G10. The process according to any of Solutions G5-G9, wherein the drying temperature is 80-180° C., the time is 0.5-24 hours, the pressure is a normal pressure or a reduced pressure G11. The process according to any of Solutions G5-G10, wherein the calcination temperature is 200-500° C., e.g. 300-450° C.; the calcination time is 2-12 hours.

G12. The process according to any of Solutions G5-G11, wherein the calcination is conducted in an oxygen-containing gas, based on the total volume of the oxygen-containing gas, the oxygen-containing gas has an oxygen content of 2-25 vol %.

G13. The process according to any of Solutions G5-G12, wherein said carbon source is at least one selected from the group consisting of carbon nanotube, active carbon, graphene, fullerene, nano-carbon fiber, nano-carbon particle, and nano-adamas.

G14. The process according to any of Solutions G5-G13, wherein said organic amine comprises at least one of an aliphatic amine, an alcoholic amine, an acid amide, an alicyclic amine and an aromatic amine; said aliphatic amine is at least one selected from the group consisting of ethyl- amine, n-propylamine, n-butylamine, di-n-propylamine, butylene diamine and hexylene diamine; said organic alcoholic amine is at least one selected from the group consisting of monoethanolamine, diethanolamine and triethanolamine; said quaternary ammonium base is at least one selected from the group consisting of tetramethylammonium hydroxide, tetraethylammonium hydroxide, tetrapropyl ammonium hydroxide and tetrabutylammonium hydroxide.

H1. A heteroatom-containing nano-carbon material, said heteroatom-containing nano-carbon material contains a carbon element, an oxygen element, and an optional nitrogen element, wherein the content of the oxygen element is 1-6 wt %, the content of the nitrogen element is 0-2 wt %, the content of the carbon element is 92-99 wt %, the element contents of said heteroatom-containing nano-carbon material are determined with the XPS method as described herein.

H2. The heteroatom-containing nano-carbon material according to Solution H1, wherein in said heteroatom-containing nano-carbon material, the content of the nitrogen element is 0.1 wt % or higher, the total content of the nitrogen element of said heteroatom-containing nano-carbon material as determined with the X-ray photoelectron spectroscopy is $I_N^t$, the content of the nitrogen element as determined with the peak(s) in the range of 398.5-400.1 eV in the X-ray photoelectron spectroscopy is $I_N^c$, $I_N^c/I_N^t$ is 0.7-1.

H3. The heteroatom-containing nano-carbon material according to Solution H1 or H2, wherein in said heteroatom-containing nano-carbon material, the amount of the oxygen element as determined with the peak(s) in the range of 531.0-532.5 eV in the X-ray photoelectron spectroscopy is $I_O^c$, the amount of the oxygen element as determined with the peak(s) in the range of 532.6-533.5 eV in the X-ray photoelectron spectroscopy is $I_O^e$, $I_O^c/I_O^e$ is 0.2-0.8; and/or the content of the carbon element as determined with the peak(s) in the range of 288.6-288.8 eV in the X-ray photoelectron spectroscopy is $I_C^c$, the content of the carbon element as determined with the peak(s) in the range of 286.0-286.2 eV in the X-ray photoelectron spectroscopy is $I_C^e$, $I_C^c/I_C^e$ is 0.2-1.

H4. The heteroatom-containing nano-carbon material according to any of Solutions H1 and H3, wherein in said heteroatom-containing nano-carbon material, the content of the nitrogen element is lower than 0.1 wt %, based on the total weight of said heteroatom-containing nano-carbon material and calculated as the elements, the oxygen content is 2.5-5.8 wt %, preferably 3-5.6 wt %, more preferably 4.5-5.5 wt %; the content of the carbon element is 94.2-97.5 wt %, preferably 94.4-97 wt %, more preferably 94.5-95.5 wt %.

H5. The heteroatom-containing nano-carbon material according to any of Solutions H1 and H3-H4, wherein in said heteroatom-containing nano-carbon material, the content of the nitrogen element is lower than 0.1 wt %, $I_O^c/I_O^e$ is 0.4-0.7, preferably 0.55-0.65; $I_C^c/I_C^e$ is preferably 0.3-0.9, more preferably 0.35-0.8, further preferably 0.5-0.7.

H6. The heteroatom-containing nano-carbon material according to any of Solutions H1-H5, wherein based on the total weight of said heteroatom-containing nano-carbon material and calculated as the elements, the content of the oxygen element is 2-6 wt %, preferably 3.5-5.5 wt %; the content of the nitrogen element is 0.2-1.8 wt %, preferably 0.5-1.8 wt %; the content of the carbon element is 92.2-97.8 wt %, preferably 92.7-96 wt %.

H7. The heteroatom-containing nano-carbon material according to any of Solutions H1-H6, wherein in said heteroatom-containing nano-carbon material, the content of the nitrogen element is 0.1 wt % or higher, $I_O^c/I_O^e$ is 0.35-0.85, preferably 0.45-0.8; $I_C^c/I_C^e$ is 0.3-0.98, preferably 0.45-0.95.

H8. The heteroatom-containing nano-carbon material according to any of Solutions H1-H7, wherein $I_N^c/I_N^t$ is 0.8-0.95.

H9. The heteroatom-containing nano-carbon material according to any of Solutions H1-H8, wherein in said heteroatom-containing nano-carbon material, based on the total amount of the carbon element determined with the X-ray photoelectron spectroscopy, the content of the carbon element determined with the peak(s) in the range of 284.7-284.9 eV in the X-ray photoelectron spectroscopy is 20 wt % or higher, preferably 40 wt % or higher, more preferably 50 wt % or higher, further preferably 70 wt % or higher; and the content of the carbon element determined with the peak(s) in the range of 284.7-284.9 eV in the X-ray photoelectron spectroscopy is 95 wt % or lower, preferably 90 wt % or lower.

H10. The heteroatom-containing nano-carbon material according to any of Solutions H1-H9, wherein said heteroatom-containing nano-carbon material is a heteroatom-containing carbon nanotube, preferably a heteroatom-containing multi-walled carbon nanotube.

H11. The heteroatom-containing nano-carbon material according to any of Solutions H1-H10, wherein said heteroatom-containing multi-walled carbon nanotube has a specific surface area of 50-500 m²/g, preferably 80-300 m²/g, more preferably 100-200 m²/g.

H12. The heteroatom-containing nano-carbon material according to any of Solutions H1-H11, wherein said heteroatom-containing multi-walled carbon nanotube has a weight loss difference $w_{800}$ in a temperature range of 400-800° C. and a weight loss difference $w_{500}$ in a temperature range of 400-500° C., $w_{500}/w_{800}$ is 0.01-0.5, preferably 0.02-0.2, said weight loss differences are measured in an air atmosphere.

H13. The heteroatom-containing nano-carbon material according to any of Solutions H1-H12, wherein based on the total weight of said heteroatom-containing nano-carbon material, the content of the oxygen element is 2-6 wt %, preferably 4-5.8 wt %, more preferably 4.5-5.5 wt %; the content of the nitrogen element is 0.2-1.8 wt %, preferably 0.8-1.6 wt %, more preferably 1-1.5 wt %; the content of the carbon element is 92.2-97.8 wt %, preferably 92.6-95.2 wt %, more preferably 93-94.5 wt %;

$I_O^c/I_O^e$ is preferably 0.3-0.8, more preferably 0.35-0.8, further preferably 0.55-0.78;

The content of the carbon element determined with the peak(s) in the range of 284.7-284.9 eV in the X-ray photoelectron spectroscopy is preferably 70-90 wt %, more preferably 75-85 wt %;

$I_C^c/I_C^e$ is preferably 0.3-0.9, more preferably 0.4-0.7, further preferably 0.45-0.6;

$I_N^c/I_N^t$ is preferably 0.7-0.98, more preferably 0.75-0.96, further preferably 0.8-0.95.

H14. The heteroatom-containing nano-carbon material according to any of Solutions H1-H13, wherein based on the total weight of said heteroatom-containing nano-carbon material, the content of the oxygen element is 2-6 wt %, preferably 3-5.5 wt %, more preferably 3.5-5 wt %; the content of the nitrogen element is 0.3-2 wt %, preferably 0.4-1.8 wt %, more preferably 0.5-1.5 wt %; the content of the carbon element is 92-97.7 wt %, preferably 92.7-96.6 wt %, more preferably 93.5-96 wt %;

$I_O^c/I_O^e$ is preferably 0.3-0.8, more preferably 0.4-0.78, further preferably 0.45-0.75; The content of the carbon element determined with the peak(s) in the range of 284.7-284.9 eV in the X-ray photoelectron spectroscopy is preferably 70-90 wt %, more preferably 70-85 wt %; $I_C^c/I_C^e$ is preferably 0.3-0.9, more preferably 0.4-0.8, further preferably 0.45-0.6; $I_N^c/I_N^t$ is preferably 0.7-0.95, more preferably 0.7-0.9, further preferably 0.8-0.9.

H15. The heteroatom-containing nano-carbon material according to any of Solutions H1-H14, wherein based on the total weight of said heteroatom-containing nano-carbon material, the content of the oxygen element is 3-6 wt %, preferably 4-5.8 wt %, more preferably 4.5-5.5 wt %; the content of the nitrogen element is 0.5-2 wt %, preferably 1-2 wt %, more preferably 1.2-1.8 wt %; the content of the carbon element is 92-96.5 wt %, preferably 92.2-95 wt %, more preferably 92.7-94.3 wt %;

$I_O^c/I_O^e$ is preferably 0.3-0.8, more preferably 0.4-0.75, further preferably 0.6-0.7;

The content of the carbon element determined with the peak(s) in the range of 284.7-284.9 eV in the X-ray photoelectron spectroscopy is preferably 70-80 wt %, more preferably 75-80 wt %;

$I_C^c/I_C^e$ is preferably 0.4-0.98, more preferably 0.7-0.98, further preferably 0.85-0.95;

$I_N^c/I_N^t$ is preferably 0.7-0.95, more preferably 0.75-0.9, further preferably 0.8-0.85.

H16. A process for preparing a heteroatom-containing nano-carbon material, which process comprises placing a starting nano-carbon material dispersed in an aqueous dispersion in a close vessel to conduct a reaction, said aqueous dispersion optionally contains an organic base, said organic base is an amine and/or a quaternary ammonium base, said aqueous dispersion is kept at a temperature in a range of 80-220° C. in the reaction.

H17. The process according to Solution H16, wherein the weight ratio of the starting nano-carbon material to water is 1:2-200, preferably 1:5-100, more preferably 1:10-50.

H18. The process according to any of Solutions H16-17, wherein said aqueous dispersion contains at least one organic base, the weight ratio of the starting nano-carbon material to the organic base is 1:0.05-20, preferably 1:0.1-10, more preferably 0.5-5.

H19. The process according to any of Solutions H16-18, wherein said organic base is selected from the group consisting of a compound represented by formula I, a compound represented by formula II, a compound represented by formula III and a substance represented by general formula $R_{12}(NH_2)_2$, $R_{12}$ is $C_1$-$C_6$alkylene or $C_6$-$C_{12}$arylene,

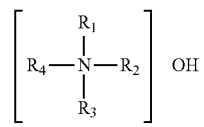

(Formula I)

In formula I, $R_1$, $R_2$, $R_3$ and $R_4$ are each $C_1$-$C_{20}$alkyl or $C_6$-$C_{12}$aryl;

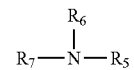

(Formula II)

In the formula II, $R_5$, $R_6$ and $R_7$ are each H, $C_1$-$C_6$alkyl or $C_6$-$C_{12}$aryl, and $R_5$, $R_6$ and $R_7$ are not H at the same time;

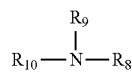
(Formula III)

In the formula III, $R_8$, $R_9$ and $R_{10}$ are each —$R_{11}$OH, hydrogen or $C_1$-$C_6$alkyl, and at least one of $R_8$, $R_9$ and $R_{10}$ is —$R_{11}$OH, $R_{11}$ is $C_1$-$C_4$alkylene.

H20. The process according to any of Solutions H16-19, wherein said aqueous dispersion is kept at a temperature in a range of 120-180° C. in the reaction.

H21. The process according to any of Solutions H16-20, wherein said reaction is maintained for a period of 0.5-96 hours, preferably 2-72 hours, more preferably 20-50 hours.

H22. The process according to any of Solutions H16-21, wherein in said starting nano-carbon material, the content of the oxygen element is lower than 1.2 wt %, preferably lower than 0.5 wt %; the content of the nitrogen element is lower than 0.1 wt %, preferably lower than 0.08 wt %, more preferably lower than 0.05 wt %.

H23. The process according to any of Solutions H16-22, wherein said starting nano-carbon material is a carbon nanotube, preferably a multi-walled carbon nanotube.

H24. The process according to any of Solutions H16-23, wherein said multi-walled carbon nanotube has a specific surface area of 20-500 m²/g, preferably 50-400 m²/g, more preferably 90-300 m²/g, further preferably 100-200 m²/g.

H25. The process according to any of Solutions H16-24, wherein said multi-walled carbon nanotube has a weight loss difference $w_{800}$ in a temperature range of 400-800° C. and a weight loss difference $w_{500}$ in a temperature range of 400-500° C., $w_{500}/w_{800}$ is 0.01-0.5, preferably 0.02-0.2, said weight loss differences are measured in an air atmosphere.

H26. The process according to any of Solutions H16-25, wherein the process further comprises separating a solid substance from the mixture obtained from the reaction, and drying and optionally calcining the separated solid substance.

H27. The process according to any of Solutions H16-26, wherein said drying is conducted at 50-200° C., preferably 80-180° C., more preferably 100-150° C., said drying is maintained for a period of 0.5-48 hours, preferably 3-24 hours, more preferably 5-12 hours.

H28. The process according to any of Solutions H16-27, wherein said organic base is a compound represented by formula I, preferably one or more of tetramethylammonium hydroxide, tetraethylammonium hydroxide, tetrapropyl ammonium hydroxide, tetrabutylammonium hydroxide and tetrapentylammonium hydroxide,

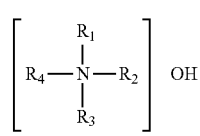
(Formula I)

In formula I, $R_1$, $R_2$, $R_3$ and $R_4$ are each $C_1$-$C_{20}$alkyl or $C_6$-$C_{12}$aryl;

the weight ratio of the starting nano-carbon material to the organic base is 1:0.1-10, preferably 0.5-5, the temperature of the aqueous dispersion is maintained at 90-210° C., preferably 140-180° C. in the reaction.

H29. The process according to any of Solutions H16-28, wherein said organic base is a compound represented by formula III, preferably one or more of monoethanolamine, diethanolamine and triethanolamine,

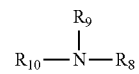
(Formula III)

In the formula III, $R_8$, $R_9$ and $R_{10}$ are each —$R_{11}$OH, hydrogen or $C_1$-$C_6$alkyl, and at least one of $R_8$, $R_9$ and $R_{10}$ is —$R_{11}$OH, $R_{11}$ is $C_1$-$C_4$alkylene;

the weight ratio of the starting nano-carbon material to the organic base is 1:0.2-10, preferably 1:1-5; the temperature of the aqueous dispersion is maintained at 90-160° C., preferably 120-150° C. in the reaction.

H30. The process according to any of Solutions H16-29, wherein said organic base is a substance represented by general formula $R_{12}(NH_2)_2$, $R_{12}$ is $C_1$-$C_6$alkylene or $C_6$-$C_{12}$arylene, preferably one or more of ethylene diamine, propylene diamine, butylene diamine, pentylene diamine and hexylene diamine;

the weight ratio of the starting nano-carbon material to the organic base is 1:0.2-10, preferably 1:1-5; the temperature of the aqueous dispersion is maintained at 100-200° C., preferably 120-150° C. in the reaction.

H31. The process according to any of Solutions H16-30, wherein the separated solid substance is dried and calcined; wherein the calcination temperature is 250-500° C., 300-480° C., 350-450° C.; the calcination time is 1-24 hours, 2-12 hours, 2-8 hours.

H32. A heteroatom-containing nano-carbon material prepared with the process according to any of Solutions H16-31.

H33. A heteroatom-containing nano-carbon material, said heteroatom-containing nano-carbon material is prepared by calcining the heteroatom-containing nano-carbon material according to any of Solutions H1-H15 or the heteroatom-containing nano-carbon material according to Solution H30.

H34. The heteroatom-containing nano-carbon material according to Solution H33, wherein said calcination is preferably conducted at 250-500° C., preferably at 300-480° C., more preferably 350-450° C.; said calcination is maintained for a period of 1-24 hours, preferably 2-12 hours, more preferably 2-8 hours.

H35. Use of the heteroatom-containing nano-carbon material according to any of Solutions H1-H15 and H32, or the heteroatom-containing nano-carbon material according to any of Solutions H33-H34 as the catalyst in the dehydrogenation of hydrocarbons.

H36. Use according to Solution H35, wherein said dehydrogenation is conducted in the presence of oxygen gas.

H37. Use according to Solution H35 or H36, wherein said hydrocarbon is an alkane, preferably $C_2$-$C_{12}$alkane, more preferably one or more of propane, n-butane, iso-butane and phenylethane.

H38. A process for dehydrogenation of hydrocarbons, which process comprises contacting hydrocarbons with the heteroatom-containing nano-carbon material according to any of Solutions H1-H15 and H32 or the heteroatom-containing nano-carbon material according to any of Solutions H33-H34 in presence or absence of oxygen in the condition for dehydrogenation of hydrocarbons.

H39. The process according to Solution H38, wherein said hydrocarbon is an alkane, preferably $C_2$-$C_{12}$alkane, more preferably one or more of propane, n-butane, iso-butane and phenylethane.

H40. The process according to any of Solutions H38-H39, wherein the mole ratio of hydrocarbon to oxygen is 0.01-100:1, preferably 0.1-10:1, further preferably 0.2-5:1, most preferably 0.3-2:1.

H41. The process according to any of Solutions H38-H40, wherein said contacting is conducted at 200-650° C., preferably at 300-600° C., more preferably at 350-500° C.; under a gauge pressure of 0-10 MPa, preferably 0.01-6 MPa, more preferably 0.02-3 MPa, further preferably 0.05-1.5 MPa; the gas hourly space velocity by volume of the starting material is 0.1-10000 $h^{-1}$, preferably 1-6000 $h^{-1}$, more preferably 5-4000 $h^{-1}$, further preferably 10-1000 $h^{-1}$, e.g. 100-500 $h^{-1}$. The present invention is described in details with the above preferable embodiments. However, it should be understood that the present invention is not limited by the minutiae in the above embodiments. Within the technical concepts of the present invention, the various simple modifications can be made to the technical solutions of the present invention, and these simple modifications are within the scope of the present invention. It should be also understood that various specific technical features described in the above specific embodiments can be combined in any suitable manner without being incompatible with each other. In order to avoid any unnecessary verbosity, all possible combinations are not described herein. It should be further understood that various embodiments can be combined to form new embodiments in any manner without deviation from the spirits of the present invention, and these new embodiments are considered as being specifically disclosed in the present invention.

The invention claimed is:

1. A heteroatom-containing nano-carbon material, comprising: 92.2-97.8 wt % of carbon, 2-6 wt % oxygen, and 0.2-1.8 wt % nitrogen, wherein each of the weight percentages is of a weight of the corresponding element in a total weight of said heteroatom-containing nano-carbon material, wherein, in said heteroatom-containing nano-carbon material, the content of the oxygen element as determined with the peak(s) in the range of 531.0-532.5 eV in an X-ray photoelectron spectrum is $I_O^c$, the content of the oxygen element as determined with the peak(s) in the range of 532.6-533.5 eV in the X-ray photoelectron spectrum is $I_O^e$, and $I_O^c/I_O^e$ is 0.2-0.8;
the content of the carbon element as determined with the peak(s) in the range of 288.6-288.8 eV in the X-ray photoelectron spectrum is $I_C^c$, the content of the carbon element as determined with the peak(s) in the range of 286.0-286.2 eV in the X-ray photoelectron spectrum is $I_C^e$, and $I_C^c/I_C^e$ is 0.2-1; and
the total content of the nitrogen element as determined with the X-ray photoelectron spectroscopy is $I_N^t$, the content of the nitrogen element as determined with the peak(s) in the range of 398.5-400.1 eV in the X-ray photoelectron spectrum is $I_N^c$, and $I_N^c/I_N^t$ is 0.7-1.

2. The heteroatom-containing nano-carbon material according to claim 1, wherein $I_O^c/I_O^e$ is 0.35-0.85, and $I_C^c/I_C^e$ is 0.3-0.98.

3. The heteroatom-containing nano-carbon material according to claim 1, wherein $I_N^c/I_N^t$ is 0.8-0.95.

4. The heteroatom-containing nano-carbon material according to claim 1, wherein the content of the carbon element determined with the peak(s) in the range of 284.7-284.9 eV in the X-ray photoelectron spectrum is 20 wt % or higher; and the content of the carbon element determined with the peak(s) in the range of 284.7-284.9 eV in the X-ray photoelectron spectrum is 95 wt % or lower.

5. The heteroatom-containing nano-carbon material according to claim 1, wherein said heteroatom-containing nano-carbon material is a heteroatom-containing carbon nanotube.

6. The heteroatom-containing nano-carbon material according to claim 5, wherein said heteroatom-containing multi-walled carbon nanotube has a specific surface area of 50-500 $m^2/g$.

7. The heteroatom-containing nano-carbon material according to claim 5, wherein said heteroatom-containing multi-walled carbon nanotube has a weight loss difference $w_{800}$ in a temperature range of 400-800° C. and a weight loss difference $w_{500}$ in a temperature range of 400-500° C., $w_{500}/w_{800}$ is 0.01-0.5, and said weight loss differences are measured in an air atmosphere.

8. The heteroatom-containing nano-carbon material according to claim 1, wherein $I_O^c/I_O^e$ is 0.3-0.8, the content of the carbon element determined with the peak(s) in the range of 284.7-284.9 eV in the X-ray photoelectron spectrum is 70-90 wt %, $I_C^c/I_C^e$ is 0.3-0.9, and $I_N^c/I_N^t$ is 0.7-0.98.

9. The heteroatom-containing nano-carbon material according to claim 1, wherein $I_O^c/I_O^e$ is 0.3-0.8, the content of the carbon element determined with the peak(s) in the range of 284.7-284.9 eV in the X-ray photoelectron spectrum is 70-90 wt %, $I_C^c/I_C^e$ is 0.3-0.9, and $I_N^c/I_N^t$ is 0.7-0.95.

10. The heteroatom-containing nano-carbon material according to claim 1, wherein $I_O^c/I_O^e$ is 0.3-0.8, the content of the carbon element determined with the peak(s) in the range of 284.7-284.9 eV in the X-ray photoelectron spectrum is 70-80 wt %, $I_C^c/I_C^e$ is 0.4-0.98, and $I_N^c/I_N^t$ is 0.7-0.95.

11. A process for preparing a heteroatom-containing nano-carbon material of claim 1, comprising: placing a starting nano-carbon material dispersed in an aqueous dispersion in a close vessel to conduct a reaction, said aqueous dispersion contains an organic base, said organic base is an amine and/or a quaternary ammonium base, said aqueous dispersion is kept at a temperature in a range of 80-220° C. in the reaction.

12. The process of claim 11, wherein the weight ratio of the starting nano-carbon material to water is 1:2-200.

13. The process according to claim 11, wherein said aqueous dispersion contains at least one organic base, the weight ratio of the starting nano-carbon material to the organic base is 1:0.05-20.

14. The process according to claim 11, wherein said organic base is selected from the group consisting of a compound represented by formula I, a compound represented by formula II, a compound represented by formula III and a substance represented by general formula $R_{12}(NH_2)_2$, $R_{12}$ is $C_1$-$C_6$alkylene or $C_6$-$C_{12}$ arylene,

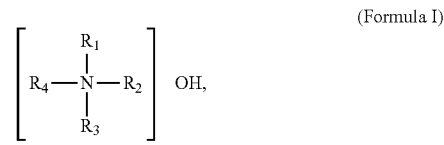

(Formula I)

in formula I, $R_1$, $R_2$, $R_3$ and $R_4$ are each $C_1$-$C_{20}$alkyl or $C_6$-$C_{12}$aryl;

in the formula II, $R_5$, $R_6$ and $R_7$ are each H, $C_1$-$C_6$ alkyl or $C_6$-$C_{12}$ aryl, and $R_5$, $R_6$ and $R_7$ are not H at the same time; and

in the formula III, $R_8$, $R_9$ and $R_{10}$ are each —$R_{11}$OH, hydrogen or $C_1$-$C_6$ alkyl, and at least one of $R_8$, $R_9$ and $R_{10}$ is —$R_{11}$OH, $R_{11}$ is $C_1$-$C_4$ alkylene.

15. The process according to claim 11, wherein said aqueous dispersion is kept at a temperature in a range of 120-180° C. in the reaction.

16. The process according to claim 11, wherein said reaction is maintained for a period of 0.5-96 hours.

17. The process according to claim 11, wherein in said starting nano-carbon material, the content of the oxygen element is lower than 1.2 wt %, the content of the nitrogen element is lower than 0.1 wt %.

18. The process according to claim 11, wherein said starting nano-carbon material is a multi-walled carbon nanotube.

19. The process according to claim 18, wherein said multi-walled carbon nanotube has a specific surface area of 20-500 m²/g.

20. The process according to claim 18, wherein said multi-walled carbon nanotube has a weight loss difference $w_{800}$ in a temperature range of 400-800° C. and a weight loss difference $w_{500}$ in a temperature range of 400-500° C., $w_{500}/w_{800}$ is 0.01-0.5, said weight loss differences are measured in an air atmosphere.

21. The process according to claim 11, wherein the process further comprises separating a solid substance from the mixture obtained from the reaction, and drying and optionally calcining the separated solid substance.

22. The process according to claim 21, wherein said drying is conducted at 50-200° C., said drying is maintained for a period of 0.5-48 hours.

23. The process according to claim 21, wherein the separated solid substance is dried and calcined; wherein the calcination temperature is 250-500° C., and the calcination time is 1-24 hours.

24. The process according to claim 11, wherein said organic base is a compound represented by formula I,

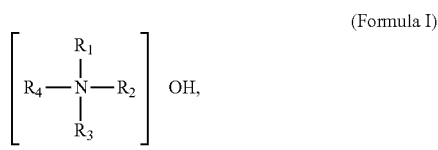

in formula I, $R_1$, $R_2$, $R_3$ and $R_4$ are each $C_1$-$C_{20}$ alkyl or $C_6$-$C_{12}$ aryl; and the weight ratio of the starting nano-carbon material to the organic base is 1:0.1-10, the temperature of the aqueous dispersion is maintained at 90-210° C. in the reaction.

25. The process according to claim 24, wherein said organic base is selected from the group consisting of tetramethylammonium hydroxide, tetraethylammonium hydroxide, tetrapropyl ammonium hydroxide, tetrabutylammonium hydroxide, tetrapentylammonium hydroxide, and mixtures thereof.

26. The process according to claim 11, wherein said organic base is a compound represented by formula III,

in the formula III, $R_8$, $R_9$ and $R_{10}$ are each —$R_{11}$OH, hydrogen or $C_1$-$C_6$ alkyl, and at least one of $R_8$, $R_9$ and $R_{10}$ is —$R_{11}$OH, $R_{11}$ is $C_1$-$C_4$ alkylene; the weight ratio of the starting nano-carbon material to the organic base is 1:0.2-10; and the temperature of the aqueous dispersion is maintained at 90-160° C. in the reaction.

27. The process according to claim 26, wherein said organic base is selected from the group consisting of monoethanolamine, diethanolamine, triethanolamine, and mixtures thereof.

28. The process according to claim 11, wherein said organic base is a substance represented by general formula $R_{12}(NH_2)_2$, $R_{12}$ is $C_1$-$C_6$ alkylene or $C_6$-$C_{12}$ arylene; the weight ratio of the starting nano-carbon material to the organic base is 1:0.2-10; and the temperature of the aqueous dispersion is maintained at 100-200° C. in the reaction.

29. The process according to claim 28, wherein said organic base is selected from the group consisting of ethylene diamine, propylene diamine, butylene diamine, pentylene diamine, hexylene diamine, and mixtures thereof.

30. A heteroatom-containing nano-carbon material, said heteroatom-containing nano-carbon material is prepared by calcining the heteroatom-containing nano-carbon material according to claim 1.

31. The heteroatom-containing nano-carbon material according to claim 30, wherein said calcination is conducted at 250-500° C., said calcination is maintained for a period of 1-24 hours.

32. A process for dehydrogenation of hydrocarbon, comprising: contacting said hydrocarbon with the heteroatom-containing nano-carbon material according to claim 1 in the presence of gaseous oxygen to generate a dehydrogenated hydrocarbon product.

33. The process according to claim 32, wherein said hydrocarbon is an alkane or a mixture of alkanes.

34. The process according to claim 32, wherein a mole ratio of hydrocarbon to the gaseous oxygen is 0.01-100:1.

35. The process according to claim 32, wherein the dehydrogenation is conducted at 200-650° C. under a gauge pressure of 0-10 MPa at a gas hourly space velocity by volume of 0.1-10000 h⁻¹.

* * * * *